(12) United States Patent
Low et al.

(10) Patent No.: US 10,960,054 B2
(45) Date of Patent: *Mar. 30, 2021

(54) FRACTURE TARGETED BONE REGENERATION THROUGH PARATHYROID HORMONE RECEPTOR STIMULATION

(71) Applicant: Purdue Research Foundation, West Lafayette, IN (US)

(72) Inventors: Philip S. Low, West Lafayette, IN (US); Stewart A. Low, West Lafayette, IN (US); Jeffery Jay Howard Nielsen, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/836,366

(22) Filed: Mar. 31, 2020

(65) Prior Publication Data

US 2020/0316174 A1 Oct. 8, 2020

Related U.S. Application Data

(63) Continuation of application No. 16/464,164, filed as application No. PCT/US2017/064081 on Nov. 30, 2017.

(60) Provisional application No. 62/553,313, filed on Sep. 1, 2017, provisional application No. 62/428,492, filed on Nov. 30, 2016.

(51) Int. Cl.
| | |
|---|---|
| *A61K 38/29* | (2006.01) |
| *A61P 19/08* | (2006.01) |
| *A61K 9/00* | (2006.01) |
| *A61P 19/10* | (2006.01) |
| *C07K 14/635* | (2006.01) |
| *A61K 38/00* | (2006.01) |

(52) U.S. Cl.
CPC ............ *A61K 38/29* (2013.01); *A61K 9/0014* (2013.01); *A61K 9/0031* (2013.01); *A61K 9/0053* (2013.01); *A61P 19/08* (2018.01); *A61P 19/10* (2018.01); *C07K 14/635* (2013.01); *A61K 38/00* (2013.01)

(58) Field of Classification Search
CPC .... A61K 38/29; A61K 9/0031; A61K 9/0014; A61K 9/0053; A61P 19/08
See application file for complete search history.

(56) References Cited

U.S. PATENT DOCUMENTS

| | | | | |
|---|---|---|---|---|
| 7,803,770 | B2 * | 9/2010 | Dey | .......................... A61K 9/08 514/16.9 |
| 8,748,382 | B2 * | 6/2014 | Dey | ...................... A61K 9/0019 514/16.7 |
| 2006/0199765 | A1 | 9/2006 | Gardella et al. | |
| 2011/0046059 | A1 | 2/2011 | Merutka et al. | |
| 2013/0157955 | A1 * | 6/2013 | Dey | ........................ A61K 38/29 514/11.8 |
| 2015/0246957 | A1 | 9/2015 | Doschak et al. | |
| 2017/0065682 | A1 * | 3/2017 | Hattersley | ............... A61P 19/02 |
| 2020/0317745 | A1 * | 10/2020 | Low | ..................... A61K 47/645 |

FOREIGN PATENT DOCUMENTS

WO WO2018102616 * 6/2018 ............. A61K 31/00

OTHER PUBLICATIONS

International Search Report and Written Opinion issued by the ISA/US Commissioner for Patents, dated Apr. 12, 2018, for International Application No. PCT/US2017/064081.

Arrighi et al., "Bone healing induced by local delivery of an engineered parathyroid hormone prodrug", Biomaterials, vol. 30, No. 9, Mar. 1, 2009, pp. 1763-1771.

International Preliminary Report on Patentability received for PCT Patent Application No. PCT/US2017/064081, dated Jun. 13, 2019, 7 pages.

* cited by examiner

*Primary Examiner* — Marcela M Cordero Garcia

(74) *Attorney, Agent, or Firm* — Faegre Drinker Biddle & Reath LLP

(57) ABSTRACT

Disclosed herein includes a drug delivery system comprising at least one peptide and a targeting ligand for bone fracture and/or for bone healing. Some embodiments include a peptide delivery system comprising at least an acidic, basic, hydrophilic, hydrophobic or neutral peptide linked to an acidic peptide or nonpeptidic polyanion for use in targeting the aforementioned attached peptide to a bone fracture surface. In some embodiments, a conjugated peptide expresses an anabolic function that acts through PTH receptor 1, and various formats of targeting ligands guide the drug to raw hydroxyapatite. This system offsets some side effects caused by free anabolic drug, such as high blood calcium concentration

20 Claims, 27 Drawing Sheets

Specification includes a Sequence Listing.

A.

Bisphosphonates

B.

C.

Polyphosphate

A.

B.

A.

B.

A.

B.

C.

A.

B.

A.

B.

A.

B.

A.

B.

C.

A.

B.

FRACTURE TARGETED BONE REGENERATION THROUGH PARATHYROID HORMONE RECEPTOR STIMULATION

CROSS-REFERENCE TO RELATED APPLICATIONS

This application is a Continuation of U.S. application Ser. No. 16/464,164, filed on May 24, 2019, which is a U.S. national stage under 35 U.S.C. § 371 of International Application No. PCT/US2017/064081, filed on Nov. 30, 2017, which claims the benefit of and priority to U.S. Provisional Application No. 62/428,492, filed Nov. 30, 2016, and U.S. Provisional Application No. 62/553,313, filed on Sep. 1, 2017, the entire disclosures of which are expressly incorporated herein by reference in their entireties.

REFERENCE TO SEQUENCE LISTING

This application contains a Sequence Listing submitted via EFS-web which is hereby incorporated by reference in its entirety for all purposes. The ASCII copy, created on Mar. 31, 2020, is named PRF_67711_15_ST25.txt and is 33 KB in size.

FIELD OF INVENTION

Various aspects and embodiments disclosed herein relate generally to the modelling, treatment, reducing resistance to the treatment, prevention, and diagnosis of diseases/symptoms induced by bone-related diseases. Embodiments include methods of treating a bone related disease, comprising the steps of: providing to a subject at least one therapeutically effective dose of a compound disclosed herein.

BACKGROUND

This section introduces aspects that may help facilitate a better understanding of the disclosure. These statements are to be read in this light and are not to be understood as admissions about what is or what is not prior art.

Healthy bone is a mix of 50-70% mineral, 20-40% organic matrix, 5-10% water, and 1-5% lipids and is constantly being recycled into new bone in order to help healthy bone to maintain its rigidity and flexibility. At the beginning of this recycling process, monocytes receive several signals pushing them to differentiate into osteoclasts. Osteoblasts then express Receptor Activator of Nuclear Factor κ B Ligand (RANKL) to the Receptor Activator of Nuclear Factor κ B (RANK) surface receptor in monocytes, initiating the TRAF6 cascade, committing the monocytes to osteoclastogenesis. Mature osteoclasts then initiate healthy catabolic bone resorption. Anabolic processes begin as mesenchymal stem cells (MSCs) are stimulated to become osteoblasts by the BMP-2/Runx2 and Wnt/β-catenin pathways. Next, matured osteoblasts deposit osteoid, a component of the bone matrix primarily composed of type I collagen, which mineralizes and becomes new bone.

The annual frequency of bone fractures is approximately 6.3 Million in the United States. This alone is a major burden to our health care system. This problem is compounded by the maturing baby boomer generation and a general aging population in much of the developed world. With baby boomers increasing the frequency of osteoporosis, the frequency of complicated and life-threatening fractures will dramatically increase. Hip fractures alone are expected to increase 160% to 500.000/year by 2040. Even now in the $21^{st}$ century. approximately a quarter of those 65 and older with hip fractures will die due to complications associated with immobility within a year after the injury. This raises a key public health concern.

Current clinical treatment of fractures generally does not include the use site-specific anabolic drugs. In fact, the only drugs approved for clinical use on such fractures are BMP-2 (approved for use only in tibial trauma) and BMP-7 (discontinued), which are applied locally and used in the treatment of open long bone fractures and spinal fusions. The need for broader application of anabolic drugs to treat bone maladies such as osteoporotic fractures is evident when one considers that 85% of the use of anabolics are off-label. (Ong, K. L. et al., Spine 35 (2010) 1794-1800). Still, the FDA judiciously continues to limit approved use of locally administered drugs to fractures that are already open and at risk of infection.

This limitation necessitates a clinically relevant approach to treating these types of fractures. Therefore it would be desirable to have a fracture treatment drug that is administered systemically yet targets the fracture site.

SUMMARY OF THE INVENTION

A first embodiment includes at least one compound of the formula X-Y-Z, or a pharmaceutically acceptable salt thereof, or a metabolite thereof, wherein X is at least one agent that modulates the activity of at least one of parathyroid hormone receptors; Z is at least one bone-targeting molecule; and Y is a linker that joins and/or links X and Z. In some embodiments, X is at least one agent that enhances the activity of at least one of parathyroid hormone receptors. Consistent with these embodiments, Z is at least one negatively charged oligopeptide or an equivalent thereof that binds to hydroxyapatite and/or raw bone.

A second embodiment includes the compound according to the first embodiment, wherein X is at least one polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to a full length parathyroid hormone related peptide (SEQ ID NO: 12), at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to a full length parathyroid hormone (SEQ ID NO: 13), and/or at least about 80%, 81%, 82%, 83%, 84%, 85%, 86%, 87%, 88%, 89%, 90%, 91%, 92%, 93%, 94%, 95%, 96%, 97%, 98%, 99%, and/or 100% identity to a full length abaloparatide or analogs thereof;

Y is at least one polypeptide comprising at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to amino acid residues 35-40, 35-41, 35-42, 35-43, 35-44, 35-45, 35-46, 35-47, 35-48, 35-49, 35-50, 35-51, 35-52, 35-55, 35-84, 41-44, 41-45, 41-46, 41-47, 41-48, 41-49, 41-50, and/or 41-84 of a full length parathyroid hormone related peptide or parathyroid hormone, and/or at least one Cathepsin K sensitive polypeptide; and Z is at least one polypeptide comprising about 4 or more, from about 4 to about 100, from about 4 to about 50, from 4 to about 20, from about 4 to about 15, from about 4 to about 10 acidic amino acid residues, polyphosphate, 2-aminohexanedioic (aminoadipic) acid or derivatives thereof, and/or alendronate or derivatives thereof. In some embodiments, Z is at least one polypeptide comprising about 4, 5, 6, 7, 8, 9, 10, 11, 12, 13, 14, 15, 16, 17, 18, 19, 20, 21, 22, 23, 24, 25, 26, 27, 28, 29, and/or 30 acidic amino acid residues, polyphosphate, 2-aminohexanedioic acid or derivatives thereof, and/or alendronate or derivatives thereof. In other embodiments, Z is at least one negatively charged oligopeptide or an equivalent thereof that binds to hydroxyapatite and/or raw bone.

In some embodiments, X is at least one polypeptide that includes a polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to a full length parathyroid hormone related peptide (SEQ ID NO: 12), at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to a full length parathyroid hormone (SEQ ID NO: 13), and/or at least about 80%, 81%, 82%, 83%, 84%, 85%, 86%, 87%, 88%, 89%, 90%, 91%, 92%, 93%, 94%, 95%, 96%, 97%, 98%, 99%, and/or 100% identity to a full length abaloparatide or analogs thereof; Y is at least one polypeptide that includes a polypeptide comprising at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to amino acid residues 35-40, 35-41, 35-42, 35-43, 35-44, 35-45, 35-46, 35-47, 35-48, 35-49, 35-50, 35-51, 35-52, 35-55, 35-84, 41-44, 41-45, 41-46, 41-47, 41-48, 41-49, 41-50, and/or 41-84 of a full length parathyroid hormone related peptide or parathyroid hormone, and/or at least one Cathepsin K sensitive polypeptide; and Z is at least one polypeptide that includes a polypeptide comprising about 4 or more, from about 4 to about 100, from about 4 to about 50, from 4 to about 20, from about 4 to about 15, from about 4 to about 10 acidic amino acid residues, polyphosphate, aminohexanedioic acid or derivatives thereof, and/or alendronate or derivatives thereof. In some embodiments, Z is at least one polypeptide that includes a polypeptide comprising about 4, 5, 6, 7, 8, 9, 10, 11, 12, 13, 14, 15, 16, 17, 18, 19, 20, 21, 22, 23, 24, 25, 26, 27, 28, 29, and/or 30 acidic amino acid residues, polyphosphate, aminohexanedioic acid or derivatives thereof, and/or alendronate or derivatives thereof.

A third embodiment includes the compound according to any one the preceding embodiments, X is at least one polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to any one of SEQ ID NOs: 1, 2, 3, 4, 5, 6, 7, 8, and/or 9; Y is at least one polypeptide comprising at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to amino acid residues 35-46 and/or 41-46 of a full length parathyroid hormone related peptide; and Z is at least one polypeptide comprising about 4 or more acidic amino acid residues, polyphosphate, and/or alendronate or derivatives thereof. In some embodiments, Z is at least one polypeptide comprising from about 4 to about 100, from about 4 to about 50, from 4 to about 20, from about 4 to about 15, from about 4 to about 10 acidic amino acid residues, polyphosphate, aminohexanedioic acid or derivatives thereof, and/or alendronate or derivatives thereof. In other embodiments, Z is at least one polypeptide comprising about 4, 5, 6, 7, 8, 9, 10, 11, 12, 13, 14, 15, 16, 17, 18, 19, 20, 21, 22, 23, 24, 25, 26, 27, 28, 29, and/or 30 acidic amino acid residues, polyphosphate, aminohexanedioic acid or derivatives thereof, and/or alendronate or derivatives thereof.

A fourth embodiment includes the compound according to any one of the first to the third embodiments, wherein X is at least one polypeptide having about 80%, 81%, 82%, 83%, 84%, 85%, 86%, 87%, 88%, 89%, 90%, 91%, 92%, 93%, 94%, 95%, 96%, 97%, 98%, 99%, and/or 100% identity to a full length abaloparatide or analogs thereof; Y is at least one polypeptide comprising at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence identity to amino acid residues 35-46 of a full length parathyroid hormone related peptide; and Z is at least one polypeptide comprising about 4 or more, from about 4 to about 100, from about 4 to about 50, from 4 to about 20, from about 4 to about 15, from about 4 to about 10 acidic amino acid residues, polyphosphate, 2-aminohexanedioic acid or derivatives thereof, and/or alendronate or derivatives thereof. In some embodiments, Z is at least one polypeptide comprising about 4, 5, 6, 7, 8, 9, 10, 11, 12, 13, 14, 15, 16, 17, 18, 19, 20, 21, 22, 23, 24, 25, 26, 27, 28, 29, and/or 30 acidic amino acid residues, polyphosphate, 2-aminohexanedioic acid or derivatives thereof, and/or alendronate or derivatives thereof.

A fifth embodiment includes the compound according to any one of the first to the fourth embodiments, wherein Z is at least one polypeptide comprising about 6, 7, 8, 9, and/or 10 acidic amino acid residues.

A sixth embodiment includes the compound according to any one of the first to the fifth embodiments, wherein the acidic amino acid residues comprise L- or D-aspartic acid, L- or D-glutamic acid, or a combination thereof.

A seventh embodiment includes the compound according to any one of the first to the sixth embodiments, wherein the acidic amino acid residues further comprises branched amino acid, and/or branched chains of amino acids.

An eighth embodiment includes the compound according to any one of the first to the seventh embodiments, wherein Y is at least one polypeptide comprising the formula of Gly-Gly-Pro-Nle, wherein Nle comprises norleucine, leucine, isoleucine, and/or an equivalent thereof (SEQ ID NO: 82).

A ninth embodiment includes the compound according to any one of the first to the eighth embodiments, wherein the compound of the formula X-Y-Z is at least one polypeptide having at least about 80%, 81%, 82%, 83%, 84%, 85%, 86%, 87%, 88%, 89%, 90%, 91%, 92%, 93%, 94%, 95%, 96%, 97%, 98%, and/or 99% sequence identity to any one of SEQ ID NO: 10 and/or SEQ ID NO:11. In some embodiments, the compound of the formula X-Y-Z is at least one polypeptide that includes a polypeptide having at least about 80%, 81%, 82%, 83%, 84%, 85%, 86%, 87%, 88%, 89%, 90%, 91%, 92%, 93%, 94%, 95%, 96%, 97%, 98%, and/or 99% sequence identity to any one of SEQ ID NO: 10 and/or SEQ ID NO:11.

A tenth embodiment includes the compound according to any one of the first to the ninth embodiments, wherein the compound of the formula X-Y-Z is at least one polypeptide having SEQ ID NO: 10 and/or SEQ ID NO: 11. In some embodiments, the compound of the formula X—Y—Z is at least one polypeptide that includes a polypeptide having SEQ ID NO: 10 and/or SEQ ID NO: 11.

An eleventh embodiment includes the compound according to any one of the first to the tenth embodiments, wherein X is at least one agonist of parathyroid hormone receptor 1.

A twelfth embodiment includes the compound according to any one of the first to the eleventh embodiments, wherein X is at least one polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence homology to the first 13 amino acid residues of the full length parathyroid hormone related peptide (SEQ ID NO: 12), at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence homology to the first 13 amino acid residues of the full length parathyroid hormone (SEQ ID NO: 13), and/or at least about 80%, 81%, 82%, 83%, 84%, 85%, 86%, 87%, 88%, 89%, 90%, 91%, 92%, 93%, 94%, 95%, 96%, 97%, 98%, 99%, and/or 100% homology to the first 13 amino acid residues of SEQ ID NO:3.

In some embodiments, X is at least one polypeptide having at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence homology to the amino acid residues 2, 3, 4, 6, 7, 9, 12 and/or 13 of the full length parathyroid hormone related peptide (SEQ ID NO: 12), at least about 80%, 81%, 82%, 83%, 84%, 85%, 86%, 87%, 88%, 89%, 90%, 91%, 92%, 93%, 94%, 95%, 96%, 97%, 98%, 99%, and/or 100% sequence homology to the amino acid residues 2, 3, 4, 6, 7, 9, 12 and/or 13 of the full length parathyroid hormone (SEQ ID NO: 13), and/or at least about 80%, 81%, 82%, 83%, 84%, 85%, 86%, 87%, 88%, 89%, 90%, 91%, 92%, 93%, 94%, 95%, 96%, 97%, 98%, 99%, and/or 100% homology to the amino acid residues 2, 3, 4, 6, 7, 9, 12 and/or 13 of SEQ ID NO:3.

A thirteenth embodiment includes a method of treating a bone-related disease, the method comprising the steps of: providing a subject at least one therapeutically effective dose of the compound of any one of the first to the twelfth embodiments, or a pharmaceutically acceptable salt or metabolite thereof.

A fourteenth embodiment includes the method according to the thirteenth embodiment, wherein the subject comprises a human, an animal, a cell, and/or a tissue.

A fifteenth embodiment includes the method according to the thirteenth and/or fourteenth embodiments, wherein the bone-related disease comprises osteopenia, osteoporosis, rheumatoid arthritis, hematologic, autoimmunity, transplant rejection, osteomyelitis, and/or bone fracture.

A sixteenth embodiment includes the method according to the thirteenth to the fifteenth embodiments, the effective dose of the compound according to any one of the first to the twelfth embodiments comprises from about 0.0001 nmol/kg/day to about 1000 nmol/kg/day, about 0.001 nmol/kg/day to about 1000 nmol/kg/day, from about 0.01 nmol/kg/day to about 1000 nmol/kg/day, from about 0.1 nmol/kg/day to about 1000 nmol/kg/day, from about 0.0001 nmol/kg/day to about 500 nmol/kg/day, about 0.001 nmol/kg/day to about 500 nmol/kg/day, from about 0.01 nmol/kg/day to about 500 nmol/kg/day, from about 1 nmol/kg/day to about 500 nmol/kg/day, from about 0.0001 nmol/kg/day to about 250 nmol/kg/day, from about 0.001 nmol/kg/day to about 250 nmol/kg/day, from about 0.01 nmol/kg/day to about 250 nmol/kg/day, from about 1 nmol/kg/day to 250 nmol/kg/day, from about 0.0001 nmol/kg/day to about 100 nmol/kg/day, about 0.001 nmol/kg/day to about 100 nmol/kg/day, from about 0.01 nmol/kg/day to about 100 nmol/kg/day, from about 1 nmol/kg/day to about 75 nmol/kg/day, from about 1 nmol/kg/day to about 100 nmol/kg/day, from about 1 nmol/kg/day to about 250 nmol/kg/day, from about 1 nmol/kg/day to about 500 nmol/kg/day, from about 10 nmol/kg/day to about 75 nmol/kg/day, from about 10 nmol/kg/day to about 100 nmol/kg/day, from about 10 nmol/kg/day to about 250 nmol/kg/day, from about 10 nmol/kg/day to about 500 nmol/kg/day, from about 20 nmol/kg/day to about 50 nmol/kg/day, from about 20 nmol/kg/day to about 75 nmol/kg/day, from about 20 nmol/kg/day to about 100 nmol/kg/day, from about 20 nmol/kg/day to about 250 nmol/kg/day, from about 20 nmol/kg/day to about 500 nmol/kg/day, and/or about 0.074 nmol/kg/day.

In some embodiments, the effective dose of the compound according to any one of the first to the twelfth embodiments comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 60, 70, 80, 90, 100, 110, 120, 130, 140, 150, 160, 170, 180, 190, and/or 200 nmol/kg/day. In other embodiments, the effective dose of the compound according to any one of the first to the twelfth embodiments comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 60, 70, 80, 90, 100, 110, 120, 130, 140, 150, 160, 170, 180, 190, and/or 200 pmol/kg/day.

A seventeenth embodiment includes the method according to the thirteenth to the fifteenth embodiments, wherein the compound of any one of the first to the twelfth embodiments is administered orally, parenterally, rectally, transdermally, sublingually, and/or intranasally.

An eighteenth embodiment includes a compound comprising: a compound of the formula X-Z; wherein: X is at least one peptide; and Z is at least one bone-targeting molecule; or a pharmaceutically acceptable salt thereof, or a metabolite thereof.

A nineteenth embodiment includes the compound according to the eighteenth embodiment, wherein Z is at least one molecule that preferentially and/or selectively targets fractured bone.

A twentieth embodiment includes the compound according to any one of eighteenth and nineteenth embodiments, wherein X is at least one peptide having fewer than 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, and/or 10 amino acid residues.

A twenty first embodiment includes the compound according to any one of eighteenth to twentieth embodiments, wherein X is at least one peptide having more than 1, 2, 3, 4, 5, 6, 7, 8, 9, and/or 10 amino acid residues.

A twenty second embodiment includes the compound according to any one of eighteenth to twenty first embodiments, wherein X is at least one peptide comprising a hydrophilic peptide, a hydrophobic peptide, a neutral peptide, a cationic peptide, and/or an anionic peptide, and/or any combination thereof.

A twenty third embodiment includes the compound according to any one of eighteenth to twenty second embodiments, wherein: X is at least one polypeptide comprising a sequence having at least 60%, 70%, 80%, 81%, 82%, 83%, 84%, 85%, 86%, 87%, 88%, 89%, and/or 90% sequence identity to any one of SEQ ID NO: 14, SEQ ID NO: 15, SEQ ID NO: 16, SEQ ID NO: 17, SEQ ID NO: 18, SEQ ID NO: 19, or analogs or metabolites thereof; and Z is at least one polypeptide comprising 4 or more acidic amino acid residues, polyphosphate, aminohexanedioic acid or derivatives thereof, alendronate or derivatives thereof, and/or bisphosphonate or derivatives thereof.

A twenty fourth embodiment includes the compound according to any one of eighteenth to twenty third embodiments, wherein: X is at least one polypeptide comprising a sequence having at least 90%, 91%, 92%, 93%, 94%, 95%, 96%, 97%, 98%, and/or 99% sequence identity to any one of SEQ ID NO: 14, SEQ ID NO: 15, SEQ ID NO: 16, SEQ ID NO: 17, SEQ ID NO: 18, SEQ ID NO: 19, or analogs or metabolites thereof; and Z is at least one polypeptide comprising 4 or more acidic amino acid residues, polyphosphate, and/or bisphosphonate or derivatives thereof.

A twenty fifth embodiment includes the compound according to any one of eighteenth to twenty fourth embodiments, wherein X is at least one polypeptide comprising a sequence having at least 95%, 96%, 97%, 98%, and/or 99% sequence identity to any one of SEQ ID NO: 14, SEQ ID NO: 15, SEQ ID NO: 16, SEQ ID NO: 17, SEQ ID NO: 18, and/or SEQ ID NO: 19.

A twenty sixth embodiment includes the compound according to any one of eighteenth to twenty fifth embodiments, wherein X is at least one polypeptide comprising a sequence having at least 100% sequence identity to any one of SEQ ID NO: 14, SEQ ID NO: 15, SEQ ID NO: 16, SEQ ID NO: 17, SEQ ID NO: 18, and/or SEQ ID NO: 19.

A twenty seventh embodiment includes the compound according to any one of eighteenth to twenty sixth embodiments, wherein Z is at least one polypeptide comprising negatively charged amino acid residues.

A twenty eighth embodiment includes the compound according to any one of eighteenth to twenty seventh embodiments, wherein Z is at least one polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, and/or 100 negatively charged amino acid residues.

A twenty ninth embodiment includes the compound according to any one of eighteenth to twenty eighth embodiments, wherein Z is at least one mono-, bi-, tri-, tetra-, penta-, hexa-bisphosphonate, and/or multiple-bisphosphonate.

A thirtieth embodiment includes the compound according to any one of eighteenth to twenty ninth embodiments, wherein Z is at least one acidic amino acid residues comprising L- or D-aspartic acid, L- or D-glutamic acid, or a combination thereof.

A thirty first embodiment includes the compound according to any one of eighteenth to thirtieth embodiments, wherein Z is at least one acidic amino acid residues comprising branched amino acid and/or branched chains of amino acids, or a combination thereof.

A thirty second embodiment includes the compound according to any one of eighteenth to thirty first embodiments, wherein Z is at least one acidic amino acid residues comprising branched amino acid and/or branched chains of amino acids, or a combination thereof.

A thirty third embodiment includes the compound according to any one of eighteenth to thirty second embodiments, where the compound of the formula X—Z comprises a sequence having at least 60%, 70%, 80%, 81%, 82%, 83%, 84%, 85%, 86%, 87%, 88%, 89%, and/or 90% sequence identity to any one of SEQ ID NOs: 23-81, or analogs or metabolites thereof.

A thirty fourth embodiment includes the compound according to any one of eighteenth to thirty third embodiments, where the compound of the formula X—Z comprises a sequence having 90%, 91%, 92%, 93%, 94%, 95%, 96%, 97%, 98%, and/or 99% sequence identity to any one of SEQ ID NOs: 23-81, or analogs or metabolites thereof.

A thirty fifth embodiment includes the compound according to any one of eighteenth to thirty fourth embodiments, where the compound of the formula X—Z comprises a sequence having 100% sequence identity to any one of SEQ ID NOs: 23-81, or analogs or metabolites thereof.

A thirty sixth embodiment includes the compound according to any one of eighteenth to thirty fifth embodiments, further comprising a linking moiety Y, wherein Y is a linker that joins and/or links both X and Z.

The present disclosure includes a compound for the targeted treatment bone fractures, the compound comprising a formula of X-Y-Z, wherein X is an active anabolic peptide or the effective fragment thereof that is an agonist of parathyroid hormone receptor 1 (PTHR1); Y is a linker; and Z is a negatively charged oligopeptide or an equivalent thereof that binds to hydroxyapatite and/or raw bone. Conceivably many variants of PTH and PTHrP could have agonistic activity of PTHR1 and be used in place of PTH or PTHrP as long as their affinity to PTHR1 is within the range of therapeutic value.

Present disclosure also provides a peptide of SEQ ID NO: 3 with 2-methylalanyl at residue 29 and aminated at residue 34 to treat bone fracture.

In one embodiment, the aforementioned active anabolic peptide or the effective fragment thereof is selected from the group consisting of parathyroid hormone related peptide (PTHrP), parathyroid hormone (PTH), Abaloparatide and agonists thereof.

In some embodiment, the active anabolic peptide or the effective fragment thereof has SEQ ID NOS: 1-9, with SEQ ID NO: 3 having 2-methylalanyl at residue 29 and aminated at residue 34.

In one embodiment, the aforementioned compound has the sequence of SEQ ID NO: 10.

In some embodiment, the active anabolic peptide or the effective fragment thereof is an variant of SEQ ID NOS: 1-3, wherein at least residues of 2, 3, 4, 6, 7, 9, 12, 13 of SEQ ID NOS: 1-3 are conserved.

In some embodiment, the active anabolic peptide or the effective fragment thereof is n variant of SEQ ID NOS: 1-3, wherein 1, 5, 10, 11, or 14-34 may be substituted with conservative amino acid.

In some embodiment, the aforementioned active anabolic peptide or the effective fragment thereof that is an agonist of PTHR1 has a therapeutic affinity range to PTHR1 between about $IC_{50}$ 0.46 nM and about $IC_{50}$ 135 nM.

In some embodiment, the aforementioned linker Y is at least some extension of any active anabolic peptide or the effective fragment thereof. For example, the linker Y may be at least one non-releasable fragment selected from various lengths of native PTHrP residues 35-173, or the combination thereof.

Alternatively, the linker Y may be at least one non-releasable fragment selected from various lengths of native PTH residues 35-84, or the combination thereof.

In some embodiment, the aforementioned linker Y is selected from the group consisting of various lengths of native PTHrP residues 35-173, or the combination thereof, and various lengths of native PTH residues 35-84, or the combination thereof.

In some embodiment, the aforementioned linker Y is a hydrolysable substrate sensitive to at least one abundant moiety produced in an osteoclast during bone remodeling. For example, the abundant moiety may be Cathepsin K.

In some embodiment, the aforementioned linker Y is a hydrolysable substrate comprising a sequence of Gly-Gly-Pro-Nle, wherein Nle is norleucine, leucine, isoleucine or any equivalent hydrophobic modification thereof (SEQ ID NO: 82).

In some embodiment, the aforementioned hydrolysable substrate comprises disulfide bonds that are sensitive to Glutathione.

In some embodiment, the aforementioned linker Y is a releasable ester.

In some embodiment, the aforementioned compound further comprises at least one spacer comprising polyethylene glycol (PEG).

In some embodiment, the aforementioned negatively charged oligopeptide comprising at least 4 acidic amino acid residues and no more than 20 acidic amino acid residues.

In some embodiment, the aforementioned negatively charged oligopeptide comprising acidic amino acid residues selected from the group consisting of aspartic acid, glutamic acid, D-aspartic, D-glutamic acid, and the combination thereof.

In some embodiment, the negatively charged oligopeptide is a linear acidic amino acid chain.

In some embodiment, the negatively charged oligopeptide comprises least two branched acidic amino acid chains, wherein the branched acidic amino acid chains are connected by at least one Lysine.

In some embodiment Z is at least one bisphosphonate. In other embodiment, Z is polyphosphate.

In some embodiment Z is a collagen mimetic peptide that intercalates imperfect collagen fibrils at bone fracture site. For example, collagen mimetic peptide may have a structure of [Gly-Pro-Hyp]$_9$-OH (SEQ ID NO:82).

In some embodiment Z is aminohexanedioic acid (alpha-aminoadipic acid) or its derivatives with more than one carbon between the backbone and the acid. For example, Z may be 2-aminomalonic acid.

This disclosure further provides a method of treating bone fracture by administering a therapeutic amount of any aforementioned compound to a patient suffering from the bone fracture.

These and other features, aspects and advantages of the present invention will become better understood with reference to the following figures, associated descriptions and claims.

BRIEF DESCRIPTION OF THE DRAWINGS

FIG. 6A. Graph of Gene Expression Ratio 1 pM PTHrP D10. Activity markers include alkaline phosphatase (ALP), Collagen I-alpha (Col1-alpha), osteocalcin (OC), osteoprotegerin (OPG), osteopontin (OPN, and Osterix (OSX). The gene expression ratio is calculated by (Treated gene expression/Vehicle control gene expression).

FIG. 6B. Graph of Gene Expression Ratio 1 pM PTHrP. Activity markers include alkaline phosphatase (ALP), Collagen I-alpha (Col1-alpha), osteocalcin (OC), osteoprotegerin (OPG), osteopontin (OPN, and Osterix (OSX). The gene expression ratio is calculated by (Treated gene expression/Vehicle control gene expression).

FIG. 6C. Graph of Gene Expression Ratio 100 pM PTHrP D10. Activity markers include alkaline phosphatase (ALP), Collagen I-alpha (Col1-alpha), osteocalcin (OC), osteoprotegerin (OPG), osteopontin (OPN, and Osterix (OSX). The gene expression ratio is calculated by (Treated gene expression/Vehicle control gene expression).

FIG. 6D. Graph of Gene Expression Ratio 100 pM PTHrP. Activity markers include alkaline phosphatase (ALP), Collagen I-alpha (Col1-alpha), osteocalcin (OC), osteoprotegerin (OPG), osteopontin (OPN, and Osterix (OSX). The gene expression ratio is calculated by (Treated gene expression/Vehicle control gene expression).

FIG. 13A and FIG. 13B represent bisphosphonates.

FIG. 13C represents the polyphosphate targeting ligand.

Figure 1:
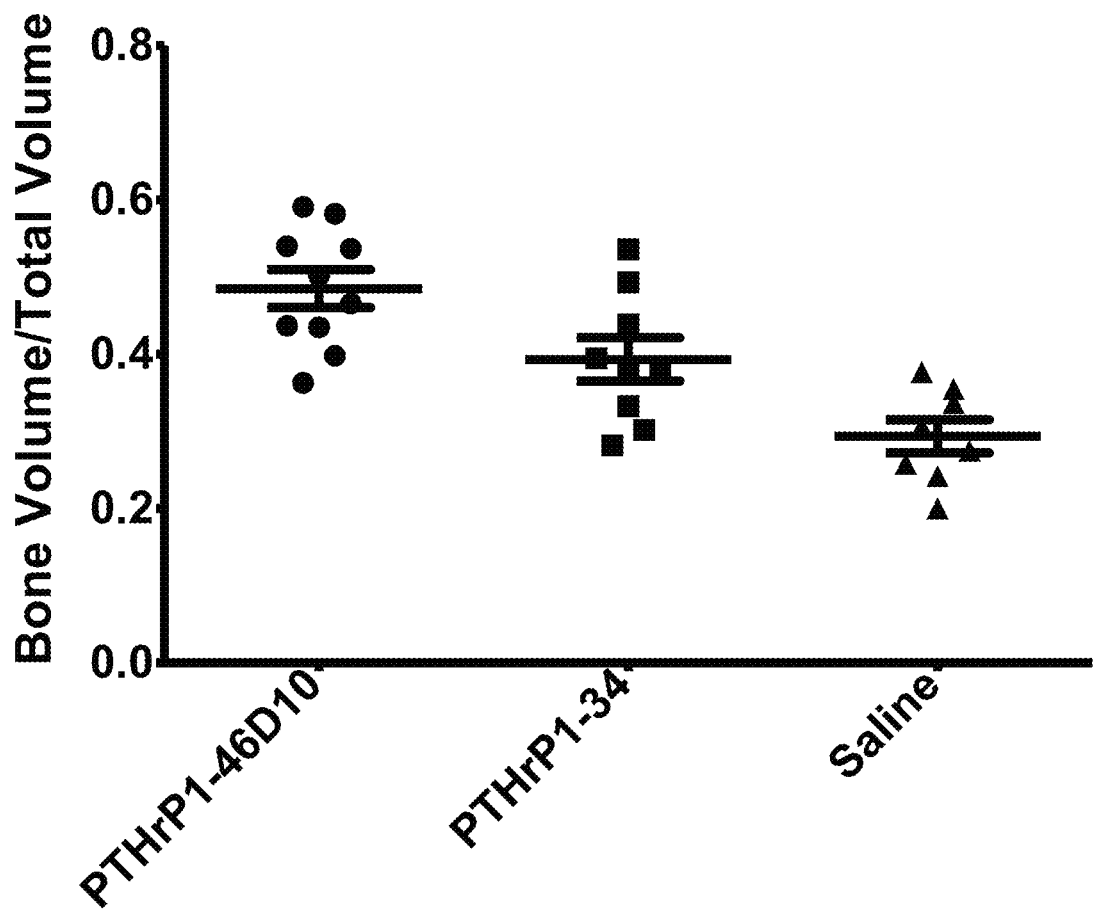
FIG. 1. Graph illustrating bone density data collected from microCT. A selection of 100 CT frames (slices) from each fracture callus were analyzed. The stack of frames were chosen from the area of the fracture where the callus was the largest.

BRIEF DESCRIPTION OF SEQUENCE LISTING
PTHrP 1-34

SEQ ID NO: 1

(AVSEHQLLHDKGKSIQDLRRRFFLHHLIAEIHTA).

PTH 1-34

SEQ ID NO: 2

(SVSEIQLMHNLGKHLNSMERVEWLRKKLQDVHNF).

Abaloparatide 1-34 with 2-methylalanyl at residue 29 and aminated at residue 34

SEQ ID NO: 3

(AVSEHQLLHDKGKSIQDLRRRELLEKLLAKLHTA).

PTHrP 1-35

SEQ ID NO: 4

(AVSEHQLLHDKGKSIQDLRRRFFLHHLIAEIHTAG).

PTHrP 1-36
SEQ ID NO: 5
(AVSEHQLLHDKGKSIQDLRRRFFLHHLIAEIHTAGI).

PTHrP 1-37
SEQ ID NO: 6
(AVSEHQLLHDKGKSIQDLRRRFFLHHLIAEIHTAGIR).

PTHrP 1-38
SEQ ID NO: 7
(AVSEHQLLHDKGKSIQDLRRRFFLHHLIAEIHTAGIRA).

PTHrP 1-39
SEQ ID NO: 8
(AVSEHQLLHDKGKSIQDLRRRFFLHHLIAEIHTAGIRAT).

PTHrP 1-40
SEQ ID NO: 9
(AVSEHQLLHDKGKSIQDLRRRFFLHHLIAEIHTAGIRATS).

PTHrP1-46D10
SEQ ID NO: 10
(VSEHQLLHDKGKSIQDLRRRFFLHHLIAEIHTAGIRATSEVSPNSDDDDDDDDDD).

PTH 1-46D10
SEQ ID NO: 11
(SVSEIQLMHNLGKHLNSMERVEWLRKKLQDVHNFVALGAPLAPRDADDDDDDDDDD).

PTHrP
SEQ ID NO: 12
(AVSEHQLLHDKGKSIQDLRRRFFLHHLIAEIHTAEIRATSEVSPNSKPSPNTKNHPVRFGSDDEGRYLTQETNKVETYKEQPLKTPGKKKKGKPGKRKEQEKKKRRTRSAWLDSGVTGSGLEGDHLSDTSTTSLELDSRRH).

PTH
SEQ ID NO: 13
(SVSEIQLMHNLGKHLNSMERVEWLRKKLQDVHNFVALGAPLAPRDAGSQRPRKKEDNVLVESHEKSLGEADKADVNVLTKAKSQ).

Heparin-binding domain of FGF2 ("F109C")
SEQ ID NO: 14
(YKRSRYTC).

Pituitary adenylate cyclase-activating polypeptide ("PACAPC")
SEQ ID NO: 15
(HSDGIFTDSYSRYRKQMAVKKYLAAVLGKRYKQRVKNKC).

Chemotactic cryptic peptide derived from the CTX region of collagen type III ("CTCC")
SEQ ID NO: 16
(YIAGVGGEKSGGFYC).

Casein kinase 2 beta chain ("Ck2.3C")
SEQ ID NO: 17
(RQIKIWFQNRRMKWKKIPVGESLKDLIDQC).

Osteopontin-derived peptide ("ODPC")
SEQ ID NO: 18
(DVDVPDGRGDSLAYGC).

P4-BMP2 ("P4C")
SEQ ID NO: 19
(KIPKASSVPTELSAISTLYLC).

PreptinD10
SEQ ID NO: 20
(DVSTSQAVLPDDFPRYDDDDDDDDDD).

SEQ ID NO: 21
SDSDD.

SEQ ID NO: 22
DSSDSSDSSDSSDSSDSS.

PTH1-34E10
SEQ ID NO: 23
(SVSEIQLMHNLGKHLNSMERVEWLRKKLQDVHNFEEEEEEEEEE).

PTHrP1-36E10
SEQ ID NO: 24
(AVSEHQLLHDKGKSIQDLRRRFFLHHLIAEIHTAGIEEEEEEEEEE).

PTHrP1-39E20
SEQ ID NO: 25
(AVSEHQLLHDKGKSIQDLRRRFFLHHLIAEIHTAGIRATCMalEEEEEEEEEEEEEEEEEEEE).
wherein Mal is maleimide in all sequences presented herein.

F109C conjugated with D10
SEQ ID NO: 26
(YKRSRYTCMalDDDDDDDDDD).

F109C conjugated with D20
SEQ ID NO: 27
(YKRSRYTCMalDDDDDDDDDDDDDDDDDDDD).

F109C conjugated with E10
SEQ ID NO: 28
(YKRSRYTCMalEEEEEEEEEE).

F109C conjugated with E20
SEQ ID NO: 29
(YKRSRYTCMalEEEEEEEEEEEEEEEEEEEE).

F109C conjugated with AAD10
SEQ ID NO: 30
(YKRSRYTCMalXXXXXXXXXX, wherein X is adipic acid).

F109C conjugated with SDSDD
SEQ ID NO: 31
(YKRSRYTCMalSDSDD).

F109C conjugated with (DSS)6
SEQ ID NO: 32
(YKRSRYTCMalDSSDSSDSSDSSDSSDSS).

PACAPC conjugated with D10
SEQ ID NO: 33
(HSDGIFTDSYSRYRKQMAVKKYLAAVLGKRYKQRVKNKCMalDDDDDDDDDD).

PACAPC conjugated with D20
SEQ ID NO: 34
(HSDGIFTDSYSRYRKQMAVKKYLAAVLGKRYKQRVKNKCMalDDDDDDDDDDDDDDDDDDDD).

PACAPC conjugated with E10
SEQ ID NO: 35
(HSDGIFTDSYSRYRKQMAVKKYLAAVLGKRYKQRVKNKCMalEEEEEEEEEE).

PACAPC conjugated with E20
SEQ ID NO: 36
(HSDGIFTDSYSRYRKQMAVKKYLAAVLGKRYKQRVKNKCMalEEEEEEEEEEEEEEEEEEEE).

PACAPC conjugated with AAD10
SEQ ID NO: 37
(HSDGIFTDSYSRYRKQMAVKKYLAAVLGKRYKQRVKNKCMalXXXXXXXXXX, wherein X is adipic acid).

PACAPC conjugated with SDSDD
SEQ ID NO: 38
(HSDGIFTDSYSRYRKQMAVKKYLAAVLGKRYKQRVKNKCMalSDSDD).

PACAPC conjugated with (DSS)$_6$
SEQ ID NO: 39
(HSDGIFTDSYSRYRKQMAVKKYLAAVLGKRYKQRVKNKCMalDSSDS
SDSSDSSDSSDSS).

CTCC conjugated with D10
SEQ ID NO: 40
(YIAGVGGEKSGGFYCMalDDDDDDDDDD).

CTCC conjugated with D20
SEQ ID NO: 41
(YIAGVGGEKSGGFYCMalDDDDDDDDDDDDDDDDDDDD).

CTCC conjugated with E10
SEQ ID NO: 42
(YIAGVGGEKSGGFYCMalEEEEEEEEEE).

CTCC conjugated with E20
SEQ ID NO: 43
(YIAGVGGEKSGGFYCMalEEEEEEEEEEEEEEEEEEEE).

CTCC conjugated with AAD10
SEQ ID NO: 44
(YIAGVGGEKSGGFYCMalXXXXXXXXXX,
wherein X is adipic acid).

CTCC conjugated with SDSDD
SEQ ID NO: 45
(YIAGVGGEKSGGFYCMalSDSDD).

CTCC conjugated with (DSS)$_6$
SEQ ID NO: 46
(YIAGVGGEKSGGFYCMalDSSDSSDSSDSSDSSDSS).

Ck2.3C conjugated with D10
SEQ ID NO: 47
(RQIKIWFQNRRMKWKKIPVGESLKDLIDQCMalDDDDDDDDDD).

Ck2.3C conjugated with D20
SEQ ID NO: 48
(RQIKIWFQNRRMKWKKIPVGESLKDLIDQCMalDDDDDDDDDDDD
DDDDDDDD).

Ck2.3C conjugated with E10
SEQ ID NO: 49
(RQIKIWFQNRRMKWKKIPVGESLKDLIDQCMalEEEEEEEEEE).

Ck2.3C conjugated with E20
SEQ ID NO: 50
(RQIKIWFQNRRMKWKKIPVGESLKDLIDQCMalEEEEEEEEEEEE
EEEEEEEE).

Ck2.3C conjugated with AAD10
SEQ ID NO: 51
(RQIKIWFQNRRMKWKKIPVGESLKDLIDQCMalXXXXXXXXXX,
wherein X is adipic acid).

Ck2.3C conjugated with SDSDD
SEQ ID NO: 52
(RQIKIWFQNRRMKWKKIPVGESLKDLIDQCMalSDSDD).

Ck2.3C conjugated with (DSS)$_6$
SEQ ID NO: 53
(RQIKIWFQNRRMKWKKIPVGESLKDLIDQCMalDSSDSSDSSDSS
DSSDSS).

ODPC conjugated with D10
SEQ ID NO: 54
(DVDVPDGRGDSLAYGCMalDDDDDDDDDD).

ODPC conjugated with D20
SEQ ID NO: 55
(DVDVPDGRGDSLAYGCMalDDDDDDDDDDDDDDDDDDDD).

ODPC conjugated with E10
SEQ ID NO: 56
(DVDVPDGRGDSLAYGCMalEEEEEEEEEE).

ODPC conjugated with E20
SEQ ID NO: 57
(DVDVPDGRGDSLAYGCMalEEEEEEEEEEEEEEEEEEEE).

ODPC conjugated with AAD10
SEQ ID NO: 58
(DVDVPDGRGDSLAYGCMalXXXXXXXXXX,
wherein X is adipic acid).

ODPC conjugated with SDSDD
SEQ ID NO: 59
(DVDVPDGRGDSLAYGCMalSDSDD).

ODPC conjugated with (DSS)$_6$
SEQ ID NO: 60
(DVDVPDGRGDSLAYGCMalDSSDSSDSSDSSDSSDSS).

P4C conjugated with D10
SEQ ID NO: 61
(KIPKASSVPTELSAISTLYLCMalDDDDDDDDDD).

P4C conjugated with D20
SEQ ID NO: 62
(KIPKASSVPTELSAISTLYLCMalDDDDDDDDDDDDDDDDDDDD).

P4C conjugated with E10
SEQ ID NO: 63
(KIPKASSVPTELSAISTLYLCMalEEEEEEEEEE).

P4C conjugated with E20
SEQ ID NO: 64
(KIPKASSVPTELSAISTLYLCMalEEEEEEEEEEEEEEEEEEEE)

P4C conjugated with AAD10
SEQ ID NO: 65
(KIPKASSVPTELSAISTLYLCMalXXXXXXXXXX,
wherein X is adipic acid).

P4C conjugated with SDSDD
SEQ ID NO: 66
(KIPKASSVPTELSAISTLYLCMalSDSDD).

P4C conjugated with (DSS)$_6$
SEQ ID NO: 67
(KIPKASSVPTELSAISTLYLCMalDSSDSSDSSDSSDSSDSS).

Branched D4 Y
SEQ ID NO: 68
(YPegKDDDDDDDD,
wherein Peg is polyethylene glycol).

Branched D8 Y
SEQ ID NO: 69
(YPegKDDDDDDDDDDDDDDDD,
wherein Peg is polyethylene glycol)

F109C conjugated with branched D10
SEQ ID NO: 70
(YKRSRYTCMalK(DDDDDDDDDD)2.

PACAPC conjugated with branched D10
SEQ ID NO: 71
(HSDGIFTDSYSRYRKQMAVKKYLAAVLGKRYKQRVKNKCMalK
(DDDDDDDDDD)2.

CTCC conjugated with branched D10
SEQ ID NO: 72
(YIAGVGGEKSGGFYCMalK(DDDDDDDDDD)2.

Ck2.3C conjugated with branched D10
SEQ ID NO: 73
(RQIKIWFQNRRMKWKKIPVGESLKDLIDQCMalK(DDDDDDDDDD)2.

-continued

ODPC conjugated with branched D10
SEQ ID NO: 74
(DVDVPDGRGDSLAYGCMalK(DDDDDDDDDD)2.

P4C conjugated with branched D10
SEQ ID NO: 75
(KIPKASSVPTELSAISTLYLCMalK(DDDDDDDDDD)2.

F109C conjugated with branched E10
SEQ ID NO: 76
(YKRSRYTCMalK(EEEEEEEEEE)2.

PACAPC conjugated with branched E10
SEQ ID NO: 77
(HSDGIFTDSYSRYRKQMAVKKYLAAVLGKRYKQRVKNKCMalK (EEEEEEEEEE)2.

CTCC conjugated with branched E10
SEQ ID NO: 78
(YIAGVGGEKSGGFYCMalK(EEEEEEEEEE)2.

Ck2.3C conjugated with branched E10
SEQ ID NO: 79
(RQIKIWFQNRRMKWKKIPVGESLKDLIDQCMalK (EEEEEEEEEE)2.

ODPC conjugated with branched E10
SEQ ID NO: 80
(DVDVPDGRGDSLAYGCMalK(EEEEEEEEEE)2.

P4C conjugated with branched E10
SEQ ID NO: 81
(KIPKASSVPTELSAISTLYLCMalK(EEEEEEEEEE)2.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

As used herein, unless explicitly stated otherwise or clearly implied otherwise the term 'about' refers to a range of values plus or minus 10 percent, e.g. about 1.0 encompasses values from 0.9 to 1.1.

The term, "treating" as used herein unless stated or implied otherwise, includes administering to a human or an animal patient at least one dose of a compound, treating includes preventing or lessening the likelihood and/or severity of at least one disease as well as limiting the length of an illness or the severity of an illness, treating may or may not result in a cure of the disease.

As used herein, unless explicitly stated otherwise or clearly implied otherwise the terms 'therapeutically effective dose,' 'therapeutically effective amounts,' and the like, refer to a portion of a compound that has a net positive effect on health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments. A "therapeutically effective amount" in general means the amount that, when administered to a subject or animal for treating a disease, is sufficient to affect the desired degree of treatment for the disease.

As used herein, "inhibition" or "inhibitory activity" each encompass whole or partial reduction of activity or effect of an enzyme or all and/or part of a pathway that includes an enzyme that is effected either directly or indirectly by the inhibitor or a pathway that is effected either directly or indirectly by the activity of the enzyme which is effected either directly or indirectly by the inhibitor.

As used herein, the term "pharmaceutically acceptable salt" is defined as a salt wherein the desired biological activity of the inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., remington: The Science and practice of pharmacy, (A. Gennaro, et al., eds., 19$^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation may also be a bolus, electuary or paste.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in a single unit-dose or multi-dose containers, and may be stored in a lyophilized condition requiring the addition of a sterile liquid carrier prior to use.

Pharmaceutically acceptable carrier: Pharmaceutically acceptable carrier, unless stated or implied otherwise, is used herein to describe any ingredient other than the active component(s) that maybe included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

As used herein, "bone related diseases" include, but are not limited to, osteopenia, osteoporosis, rheumatoid arthritis, hematologic, autoimmunity, transplant rejection, bone cancer, and/or bone fracture.

As described herein, a "therapeutic affinity index" is an affinity range of a therapeutic ligand, usually expressed by IC50 of the therapeutic ligand or agonists thereof to engage a receptor mediated signaling cascade (event) to achieve the desired therapeutic effect.

For example, if a ligand has a IC50 of 4 nM-15 nM to trigger a G-protein coupled receptor mediated response that achieve the ligand's therapeutic effect, then the ligand has a therapeutic affinity index of IC50 about 4 nM to about 15 nM. Therapeutic affinity index may be complicated when the therapeutic ligand has different modes of actions to achieve its different therapeutic effects. For example, if the receptor for the therapeutic ligand has two different conformations, each conformation may have a distinct therapeutic affinity index.

As used herein, unless explicitly stated otherwise or clearly implied otherwise the terms "PTHrP1-46D10," "PTHrP D10," and "targeted PTHrP" can be used interchangeably to define the same compound.

As used herein, unless explicitly stated otherwise or clearly implied otherwise the terms "PTHrP1-34," "PTHrP," "free PTHrP," and "non-targeted PTHrP" can be used interchangeably to define the same compound.

Osteoporosis is defined as low bone mineral density and/or poor bone microarchitecture associated with increased risk of fractures. This chronic disease mainly affects postmenopausal women, but it may also older men. This disease is increasingly being considered an age-related morbidity. The skeletal alterations observed in patient with in osteoporosis are a consequence of a relative deficit of bone formation relative to bone resorption. Osteoporosis therapies have mostly relied on antiresorptive drugs. One current, an alternative therapeutic approach for treating osteoporosis, is based on the intermittent administration of parathyroid hormone (PTH). PTH is secreted by the chiefly by cells of the parathyroid glands as a prohormone polypeptide that include 84 amino acids. An effective hormone-receptor interaction only requires the 34-N-terminal amino acids. PTH acts to increase the concentration of ionic calcium ($Ca^{2+}$) in the blood. PTH essentially acts to increase the concentration of calcium in the blood by acting upon the parathyroid hormone 1 receptor, which is present at high levels in bone and kidney. The protein hPTH-(1-34) crystallizes as a slightly bent, long helical dimer. Analysis reveals that the extended helical conformation of hPTH-(1-34) is the likely bioactive conformation. The N-terminal fragment (1-34 of parathyroid hormone (PTH) has been crystallized and the structure has been refined to 0.9 Å resolution.

Bone anabolism caused by PTH therapy is mainly accounted for by the ability of PTH to increase osteoblastogenesis and osteoblast survival. PTH and PTH-related protein (PTHrP)-an abundant local factor in bone-interact with the common PTH type 1 receptor with similar affinities in osteoblasts. Studies mainly in osteoporosis rodent models and limited data in postmenopausal women suggest that N-terminal PTHrP peptides might be considered a promising bone anabolic therapy.

Parathyroid hormone/parathyroid hormone-related peptide receptor also known as parathyroid hormone receptor 1 (PTHR1) is a protein that in humans is encoded by the PTHR1 gene. PTHR1 functions as a receptor for parathyroid hormone (PTH) and for parathyroid hormone-related protein (PTHrP).

PTHR1 belongs to family B G-protein-coupled receptor (GPCR) that is expressed primarily in bone, kidney and cartilage but also in other tissues including the vasculature and certain developing organs.

N-terminal fragments consisting of the first 34 residues of PTH and PTHrP are generally thought to contain the key functional determinants of receptor interaction present in the corresponding full-length, mature polypeptide chains, which also includes 84 and 141 amino acid residues, respectively. PTH and PTHrP are distinct among the family B peptide ligands in that they include extended C-terminal segments. The biological roles of these segments remains obscure, although some functional responses have been identified, such as a capacity of fragments corresponding to the C-terminal portion of PTH to induce pro-apoptotic effects in osteocytes17 and of fragments encompassing the mid-region of PTHrP.

Membrane binding assays developed to evaluate the affinity of ligands for PTHR1 in conformations formed upon coupling to a heterotrimeric G protein ($R^G$ conformation) or when PTHR1 is not coupled to a G protein (R conformation) provided the initial clues that structurally distinct PTH and PTHrP analogues can bind with altered affinities to the different receptor conformational states. Direct comparative studies of PTH(1-34) and PTHrP(1-36) demonstrated that although these two peptides maintain similar affinity for the $R^G$ state, they do not have the same affinity for the $R^0$ state, with PTH(1-34) displaying a much higher affinity for $R^0$ than PTHrP(1-36).

Abaloparatide, PTHrP, and PTH share high homology in the first 13 amino acids of each protein. As long as each active anabolic drug comprises a peptide that triggers signaling by the parathyroid hormone and includes or contains a minimum homology at residues of 2, 3, 4, 6, 7, 9, 12 and 13, anabolic peptide variants can be combined with various linkers, optionally spacers and targeting ligands described in this disclosure to effect targeted delivery of bone fracture healing agent.

The functional consequences of this altered selectivity were typically revealed in cAMP assays. PTH(1-34) and PTHrP(1-36) had similar potencies in conventional cAMP dose-response assays (in accordance with their similar affinities for the $R^G$ state and a GaS-mediated mechanism of intracellular cAMP production). However, the duration of the responses induced by the two ligands (assessed using a time-course washout assay) was different, with PTH(1-34) showing a more prolonged response than PTHrP(1-36). In general, the duration of the cAMP responses observed in the cell-based studies correlate with the different affinities that PTH(1-34) and PTHrP(1-36) exhibit for the $R^0$ state, rather than with their affinities for the $R^G$ state, as assessed in membrane assays. As the $R^0$ state is not coupled to a G protein and, hence, is inactive with regard to cAMP signaling, it may be that although $R^0$ complexes are fairly stable over time they can isomerizes to a functional G-protein-coupled state.

One key structural determinant of $R^0$ versus $R^G$ affinity that differs between PTH and PTHrP ligands can be traced to the identity of the residue at position 5; thus, replacing His5 in PTHrP(1-36) with the corresponding isoleucine of PTH markedly enhances affinity for $R^0$ and extends the duration of the cAMP signaling response induced in target cells.

Currently, PTH, PTHrP or their agonists are tested for either local or systematic administration to provide anabolic agent to heal any bone fracture. However these tests have revealed that there are side effects to the use of those proteins. For example, local application of PTH or PTHrP requires exposing the bone and resulted in with increased healing time, pain and discomfort, and even the possibility of infection. Alternatively, systematic application of PTH and PTHrP tend to have off target effects, including an increase in blood calcium levels. Therefore, the development of a bone anabolic agent delivery system that and may mitigate the above referenced side effects is desirous.

A drug delivery system comprising a drug, a linker and a targeting ligand is disclosed herein. Some aspects of the present disclosure provide compounds for targeting and healing of bone fractures. These compounds may comprise at least three distinct structural/functional regions: an effective anabolic peptide or any agonist that engages parathyroid hormone receptor 1 (PTHR1) and subsequent signaling cascade that leads to the healing; a linker with or without a spacer to provide a flexible arm length for the anabolic peptide to reach the bone fracture site; and a targeting ligand which typically comprises a negatively charged oligopeptide or its equivalent to guide the compound to the fracture site and specifically bind to hydroxyapatite and/or raw bone. In one particular aspect, the drug may be the first 34 amino acids in parathyroid hormone related peptide (PTHrP). The linker can include amino acid 35-46 of PTHrP, which spaces the drug from the targeting ligand and also gives leeway to the length of the drug, as some believe that amino acid 35-40 may increase receptor binding. Finally, the targeting ligand can include aspartic acid decapeptide, although other polymers functionalized by carboxylic acid are likely to bind in a similar manner (e.g. D or L glutamic acid, D or Laspartic acid and Aminohexanedioic acid in various combinations and arrangements).

A peptide comprising SEQ ID NO:3 (Abaloparatide 1-34) with residue 29 methyl Ala, and residue 34 aminated can serve as a potent active anabolic agent without further linker or targeting ligand to treat bone fracture.

It is conceivable that PTH and PTHrP may have variants possessing agonistic activity of PTHR1 and be used in place of PTH or PTHrP to engage and achieve a therapeutic effect of bone fracture healing. As long as each active anabolic drug comprises a peptide that triggers signaling by the parathyroid hormone and includes or contains a minimum homology at residues of 2, 3, 4, 6, 7, 9, 12 and 13, the proposed anabolic peptide variants may be combined with various linkers, optionally spacers and targeting ligands described in this disclosure to effect targeted delivery of bone fracture healing agent. For example, conservative substitutions or modifications at residues 1, 5, 10, 11, or 14-34 for PTH or PTHrP along with any combinations of herein described linker sequence and targeting ligand are contemplated for the protection in this disclosure.

In one aspect of the present disclosure, the targeting ligand comprises an acidic oligopeptide comprising a plurality of aspartic acid residues. The number of D or L aspartic acid residues may be from about 4 to about 10, or from about 10 to about 20 residues. The oligopeptide may be linear or it may be branched. In one illustrative embodiment, a lysine residue is used as the branch point. In another aspect of the present invention, the aspartic acid may be either L-aspartic acid, D-aspartic acid or a mixture of either enantiomer. An advantage of including the D-aspartic acid in the oligopeptide is that it may be less susceptible to proteolytic degradation as compared to an oligopeptide comprising only the naturally-occurring L-aspartic acid.

In other aspect of the present disclosure, the acidic oligopeptide may be no more than 20 L or D-glutamic acid. In yet another aspect of the present disclosure, the acidic oligopeptide may be the combination of no more than 20 L or D-aspartic acid, or L or D-glutamic acid.

In some aspect of the present disclosure, the targeting ligand may be polyphosphate or at least one bisphosphate. In yet other aspect of the present disclosure, the targeting ligand may be a collagen mimetic peptide. Such collagen mimetic peptide intercalates imperfect collagen fibrils at bone fracture site. In one aspect of the present disclosure, the collagen mimetic peptide may have the structure of [Gly-Pro-Hyp]9-OH (SEQ ID NO: 83).

In some aspect of the present disclosure, the targeting ligand may be aminohexanedioic acid (alpha-aminodadipic acid) or its derivatives with more than one carbon between the backbone and the acid. For example, the targeting ligand may be 2-aminomalonic acid.

In some aspect of the present disclosure, the targeted delivery compound further comprises at least one spacer comprising PEG (polyethylene glycol).

Between the active anabolic compound such as PTH or PTHrP or their respective agonists and the targeting ligand, there can be a flexible length of linker sequence. In some aspect of the disclosure, the linker may be any portion of the extension of PTH or PTHrP's active fragment, namely from residues 35-84 of PTH or 35-173 of PTHrP. Such extension of the active fragment is usually non-releasable and the linker sequence can be any portion of the extension or the combinations of different portions of the extension.

In some other aspect of the disclosure, the linker can be a hydrolysable substrate sensitive to at least one abundant moiety produced in an osteoclast during bone remodeling. For example, Cathespin K is a moiety that is produced in an osteoclast during bone remodeling. A linker sequence comprising Gly-Gly-Pro-Nle (where Nle is norleucine, Leucine, isoleucine or any other equivalent with hydrophobic modification may serve as the substrate of Cathespin K) (SEQ ID NO: 82). Once the targeted compound is delivered at osteoclast site, Cathespin K may hydrolyze the linker and release the active anabolic compound to work on the bone healing.

Yet another hydrolysable linker may comprise disulfide bonds, and it may be released by glutathione at the osteoclast.

Yet another hydrolysable linker may be a releasable ester.

These features of the current disclosure are further demonstrated by following Examples.

Material and Methods

Synthesis

Peptides were synthesized by either solid-phase peptide synthesis or by recombinant expression.

Solid Phase Peptide Synthesis

Briefly, in a solid phase peptide synthesis vial capable of bubbling nitrogen, 2-chlorotrityl resin (1.11 mmol/g) was loaded at 0.4 mmol/g with the first amino acid overnight in DCM and DIPEA. The resin was then capped with four 5 mL washes of DCM/MeOH/DIPEA (17:2:1), followed by three washes of DCM and DMF, respectively. Following each amino acid coupling reaction, Fmoc-groups were removed by three 10 min incubations with 20% (v/v) piperidine in DMF. The resin was then washed 3× with DMF prior to the next amino acid being added. Each amino acid was added in a 5-fold excess with HBTU/DIPEA. Upon completion of the synthesis, peptide were cleaved using 95:2.5:2.5 trifluoroacetic acid:water:triisopropylsilane. Cysteine containing peptides were cleaved using 95:2.5:2.5 and 10 fold excess TCEP trifluoroacetic acid:triisopropylsilane: water:TCEP (tris(2-carboxyethyl)phosphine).

Recombinant Protein Expression

Ampicillian resistant plasmids were generated containing a T7 promoter, thioredoxin coding sequence, HisTag sequence, tryptophan residue, and peptide coding sequence. Competent cells were transformed with the plasmids and plated on ampicillin containing auger plates. Single colonies were selected and expanded overnight in ampicillin (100 ug/ml) LB media at 37 C. The Competent cells were then expanded further in 1l of ampicillin (100 ug/ml) LB media for 15 hours. At 15 hour IPTG was added to reach a final concentration of 1 mM and the media was agitated at 180 rpm at 37 C for 5 hours. Cells were then pelleted and lysed by sonication in 20 mM Tris-HCL at pH8 containing 6M Guanidine HCl. Fusion protein was then isolated by elution on from a HisTag using imidazole. Fusion protein containing fractions were dialyzed and lyophilized. Proteolytic cleavage was performed using the iodosobenzoic acid method. Final peptide was purified using an anion exchange column, dialyzed, and lyophilized for further used Characterization Peptide molecular weights were confirmed using HPLC/MS.

Murine Fracture Induction.

All animal studies were done in accordance to Purdue's animal care and use committee protocol and were done performed as described in the literature. CD4 Swiss mice (30-35 g) acquired from Harlan laboratories were used for these experiments. A stabilized femoral fracture was performed under aseptic conditions with isoflurane anesthesia. Skin around the knee was shaved and cleaned with an alcohol pad first, then with Betadine solution. The skin incision was made medial parapetellar. The patella was then dislocated and an incision was made under the patella. A 25 gauge needle was used to ream the intramedullary canal. A 22 gauge locking nail (where both ends are flattened to produce rotational stability), was then inserted. The wound was sutured and the bone was then fractured using a three point bending device that has a built-in stop to prevent excess injury. Subcutaneous Buprenorphine (0.05-0.1 mg/kg) was administered at the time of surgery, followed by a dose every 12 h for 3-7 days post operation.

Dosing:

Mice were dosed subcutaneously, daily with 31 nmol/kg peptide or saline control. The first dose was administered 6 hours following fracture and continued on throughout the study, the last dose being administered the day before euthanasia.

Bone Density Analysis

Scanco μCT 40 was used to collect CT images and data of bone. The bones were scanned while immersed in PBS to prevent dehydration. ImageJ software was used to analyze the images for bone density, total volume (TV), relative bone volume (BV/TV), trabecular thickness (Tb.Th), and trabecular spacing (Tb.Sp). Volumes of interest included the fracture callus, and both cortical and trabecular bone between the points on the cortical bone at the fracture site.

Statistical analyses were calculated using Prism GraphPad software. Data are presented in results as mean t standard error of the mean (SEM). An unpaired student's t-test was used to determine statistical significance, with P-values less than 0.05 being considered statistically significant.

Example 1. A PTHrP Delivery System for Targeted Bone Fracture Healing

In this Example a fracture targeted pharmaceutical comprising a drug, a linker and a targeting ligand were synthesized.

The sequence of the pharmaceutical is listed in SEQ ID NO:10, which comprises amino acid residues 1-46 of PTHrP followed by 10-Aspartic acids. As described above, residues 1-34 are the active portion of PTHrP, residues 35-46 are the linker portion of the proposed pharmaceutical for healing bone fracture, and the 10-Aspartic acids are the targeting ligand.

The closed femoral fractures were produced in three groups of mice. Mice were dosed daily for 4 weeks with either targeted PTHrP (31 nmol/kg/day). PTHrP 1-34 (31 nmol/kg/day) or saline. At the end of the study, mice were euthanized by CO2, femurs were harvested, and bone densities were determined by MicroCT.

As shown in FIG. 1, the targeted version of PTHrP increased bone densities around fractures significantly higher than that of free PTHrP and Saline. This indicates that the strategy of using an effective anabolic agent linked to a targeting ligand sequence may work for bone fracture healing.

Figure 2:
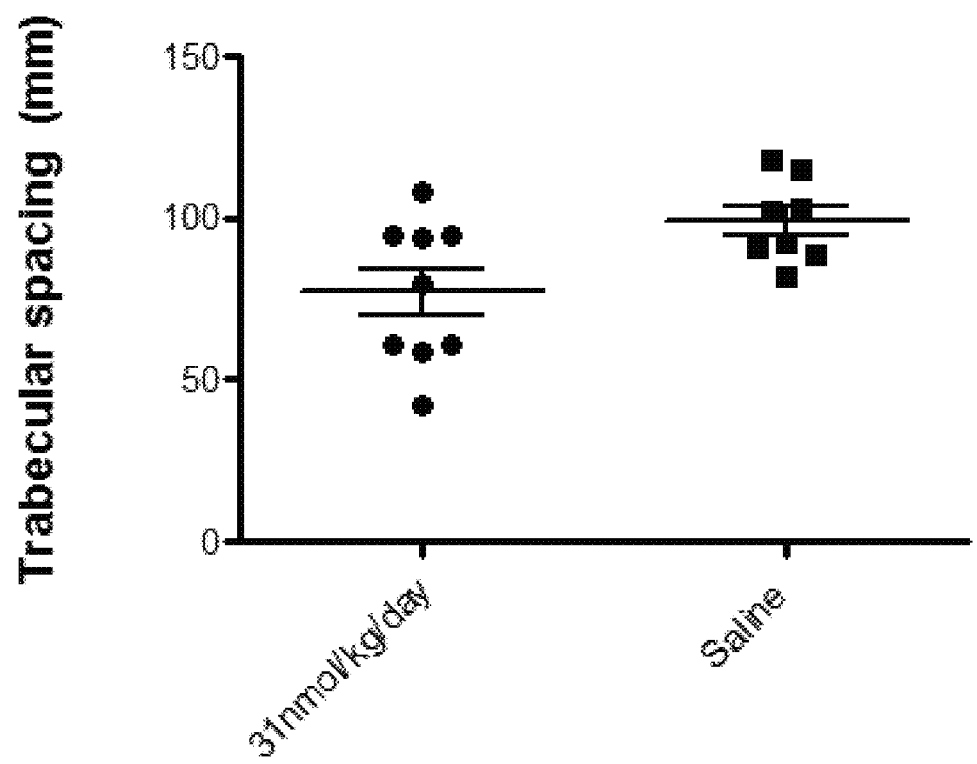
FIG. 2. Graph illustrating trabecular spacing data collected from microCT. Narrower spacing is associated higher density bone and can be indicative of progressed healing. A selection of 100 CT frames (slices) from each fracture callus were analyzed.

Another way of indicating the progress of bone healing is to measure trabecular spacing data collected from microCT. As shown in FIG. 2, a selection of 100 CT frames (slices) from each fracture callus were analyzed. The stack of frames were chosen from the area of the fracture where the callus was the largest. From left to right the targeted PTHrP (PTHrP 1-46 followed by 10 aspartic acids) and saline control. Targeted PTHrP has statistically tighter spacing than does the saline control.

Comparing to the traditional single anabolic agent administration, which typically causes high calcium concentrations in blood, the instant application provides an alternative and it is superior to the need of locally applying the bone fracture healing agent. This mitigates the risk of high blood calcium level or bone exposure associated infections etc.

It is contemplated that various conservative substitutions to the first 34 amino acids will lead to the same or better bone density recovering in the fractured mice.

It is also contemplated that using other portions of PTHrP extension sequences beyond 1-34 may provide similar or better connection to the targeting ligand of 10 Aspartic acids.

It is further contemplated that using any linker and targeting ligand described in the instant disclosure. For example, the linker can be variations of the native peptide of PTH sequence, or any Cathepsin K sensitive linker such as Gly-Gly-Pro-Nle where Nle is a norleucine or another hydrophobic amino acid such as leucine or isoleucine (SEQ ID NO: 82). The linker may be a disulfide linker that can be released in a reductive environment. Glutathione is usually released in certain types of injury and may reduce disulfide bonds. It is contemplated a disulfide linker may increase the potency of the anabolic agent. The linker may also be an ester that is hydrolyzed and released to increase the healing efficiency. The targeting ligands are usually acidic oligopeptide chains containing 4 or more acidic amino acid residues and they bind to hydroxyapatite and/or raw bone. These acidic amino acid residues can be any of aspartic or glutamic acid or the combination thereof. In some occasions, acidic oligopeptide may be branched with at least one Lysine to increase the drug accumulation in the fracture site. The branched chains can be multiple branches, such as 2, 3, or 4 etc.

Another choice of targeting ligand is one or more bisphosphate, i.e. poly bisphosphate. A collagen mimetic peptide with the sequence of [Gly-Pro-Hyp]$_9$-OH (SEQ ID NO: 83).

Yet another choice of targeting ligand is aminohxanedioic acid (alpha-aminodadipic acid) or its derivatives with more than one carbon between the backbone and the acid. For example, 2-aminomalonic acid may be used as the targeting ligand for PTHrP or its variants.

A spacer such as PEG (polyethylene glycol) can be added into the synthesized targeted drug delivery system to reduce the probability of the targeting ligand interfering with the anabolic efficiency.

For various different combinations of PTHrP variant-linker-targeting ligand choices, the testing of bone density recovery can be performed similarly like described in this Example. Specifically, the synthesized drug-linker-targeting ligand is compared to the PTHrP variant itself and saline for their effect on bone densities around fractures. The targeted version of PTHrP variants is expected to increase bone densities around fracture significantly higher than that of free PTHrP variant and Saline.

Figure 3:
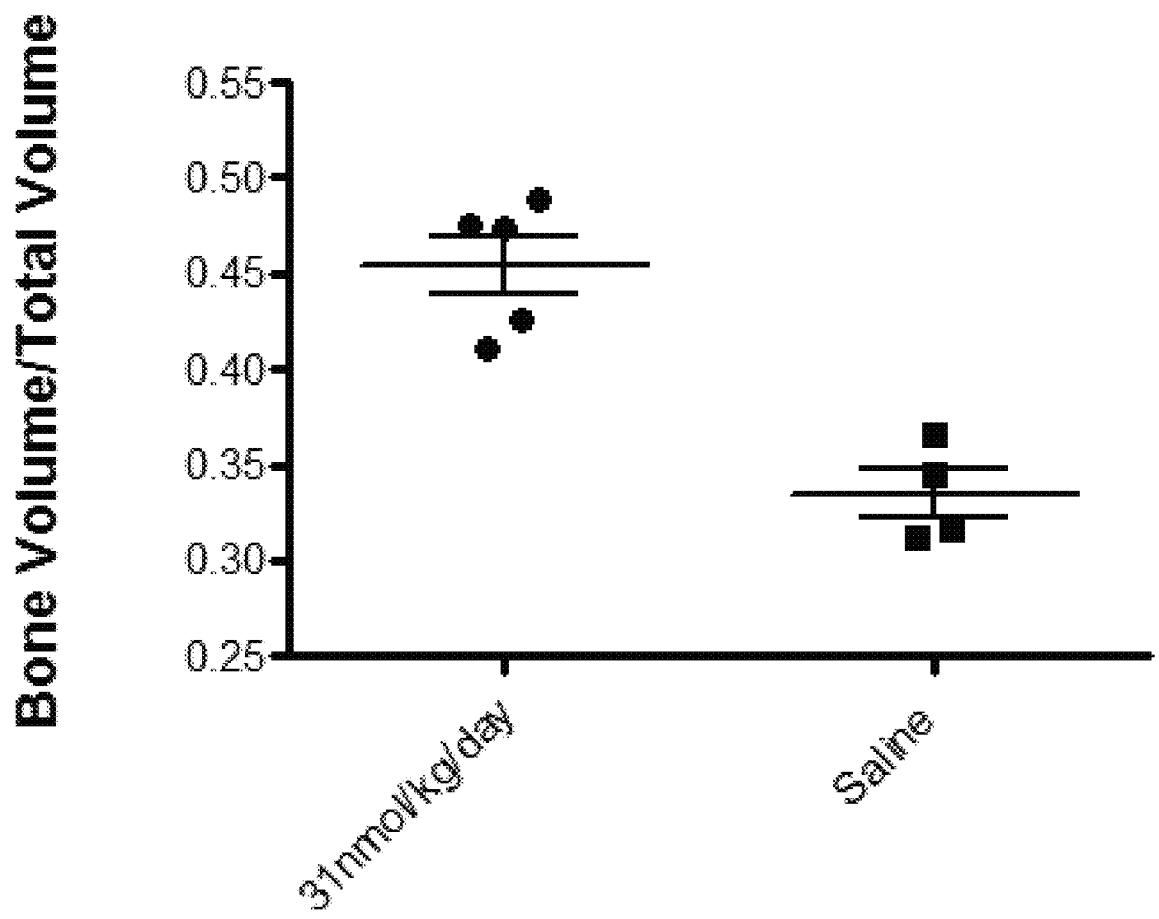
FIG. 3. Graph illustrating bone density data collected from microCT. A selection of 100 CT frames (slices) from each fracture callus were analyzed. The stack of frames were chosen from the area of the fracture where the callus was the largest.

Example 2. Various Different Combinations of Anabolic Drug with Linker Choices and Targeting Ligands to Make Targeted Delivery of the Drug to Bone Fracture for Healing In this Example, the first 34 amino acid of PTH is synthesized with a suitable linker described herein and a suitable targeting ligand. Like in Example 1, the linker may be any segment of the extension of the active PTH, including residues 35-84, or other linkers described in Example 1. The targeting ligand may be any of those described in Example 1. As shown in FIG. 3, the linker is the amino acid residues 36-46 and the targeting ligand is 10 aspartic acid. The synthesized drug-linker-targeting ligand (PTH 1-46D10, SEQ ID NO:11) may be compared to the PTH variant itself and saline for their effect on bone densities around fractures. The targeted version of PTH variants is expected to increase bone densities around fracture significantly higher than that of free PTH variant and Saline. FIG. 3 has shown targeted PTH 1-46D10 is statistically denser than saline controls.

It is conceivable some other effective anabolic drugs can be used to replace PTH (1-34) in this Example and achieve the bone fracture healing.

Example 3. Abaloparatide 1-34 as a Free Standing Bone Fracture Healing Agent

In this Example, Abaloparatide 1-34 with modified residues on 29 as Methyl Ala and on 34 as aminated Ala (SEQ ID NO:3) were tested. Abaloparatide has been tested treating osteoporosis to prevent fractures. Its ability to heal actual fractures is being tested, which is a different process. Of course, having Abaloparatide 1-34 linked to the linkers and targeting ligands described in previous Examples will likely increase the bone density at the fracture site, due to the targeted delivery.

Referring now to FIG. 1, a selection of 100 CT frames (slices) from each fracture callus were analyzed. CT frames were taken at 4 weeks. The stack of frames was chosen from the area of the fracture where the callus was the largest. From left to right the targeted PTHrP (PTHrP 1-46 followed by 10 aspartic acids), free unconjugated PTHrP (PTHrP1-34), and saline control. The targeted version of PTHrP increased bone densities around fractures significantly higher than that of free PTHrP and Saline.

Referring now to FIG. 2, narrower spacing is associated higher density bone and can be indicative of progressed healing. CT frames were taken at 4 weeks. A selection of 100 CT frames (slices) from each fracture callus was analyzed. The stack of frames was chosen from the area of the fracture where the callus was the largest. From left to right the targeted PTHrP (PTHrP 1-46 followed by 10 aspartic acids)

and saline control. Targeted PTHrP has statistically tighter spacing than does the saline control.

Referring now to FIG. 3, a selection of 100 CT frames (slices) from each fracture callus were analyzed. CT frames were taken at 2 weeks. The stack of frames was chosen from the area of the fracture where the callus was the largest. From left to right the targeted PTH (PTH 1-46 followed by 10 aspartic acids) and saline control. Targeted PTH is statistically denser than saline controls.

Figure 4:
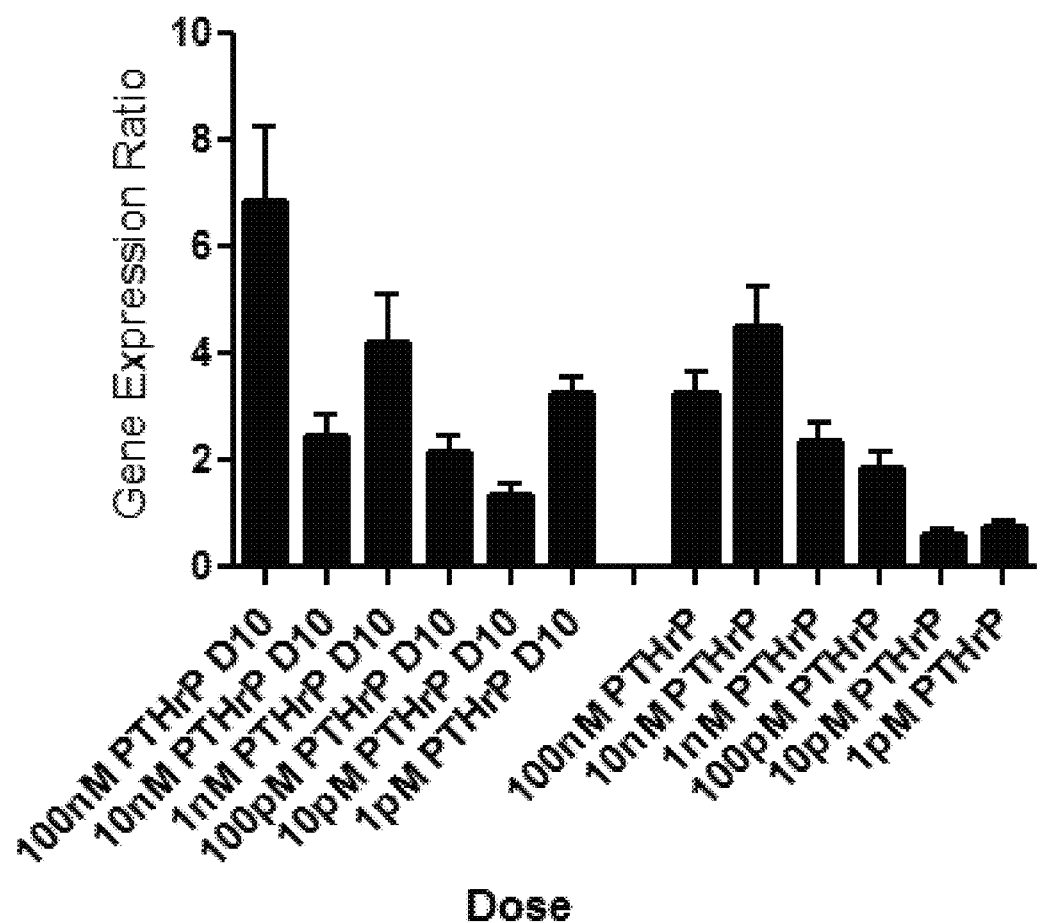
FIG. 4. Graph illustrating alkaline phosphatase (ALP) expression ratio for both targeted and non-targeted PTHrP in MC3T3E1 cells. The ALP ratio is calculated by (Treated ALP expression/Vehicle control ALP expression). The expression was standardized to GAPDH.

Referring now to FIG. 4, alkaline phosphatase (ALP) expression ratio for both targeted and non-targeted PTHrP were analyzed in MC3T3E1 cells. The ALP ratio is calculated by (Treated ALP expression/Vehicle control ALP expression). Higher expression levels are associated with greater osteoblast activity and is a key protein involved in bone mineralization. The addition of targeting ligand does not reduce the efficacy of the drug.

Figure 5:
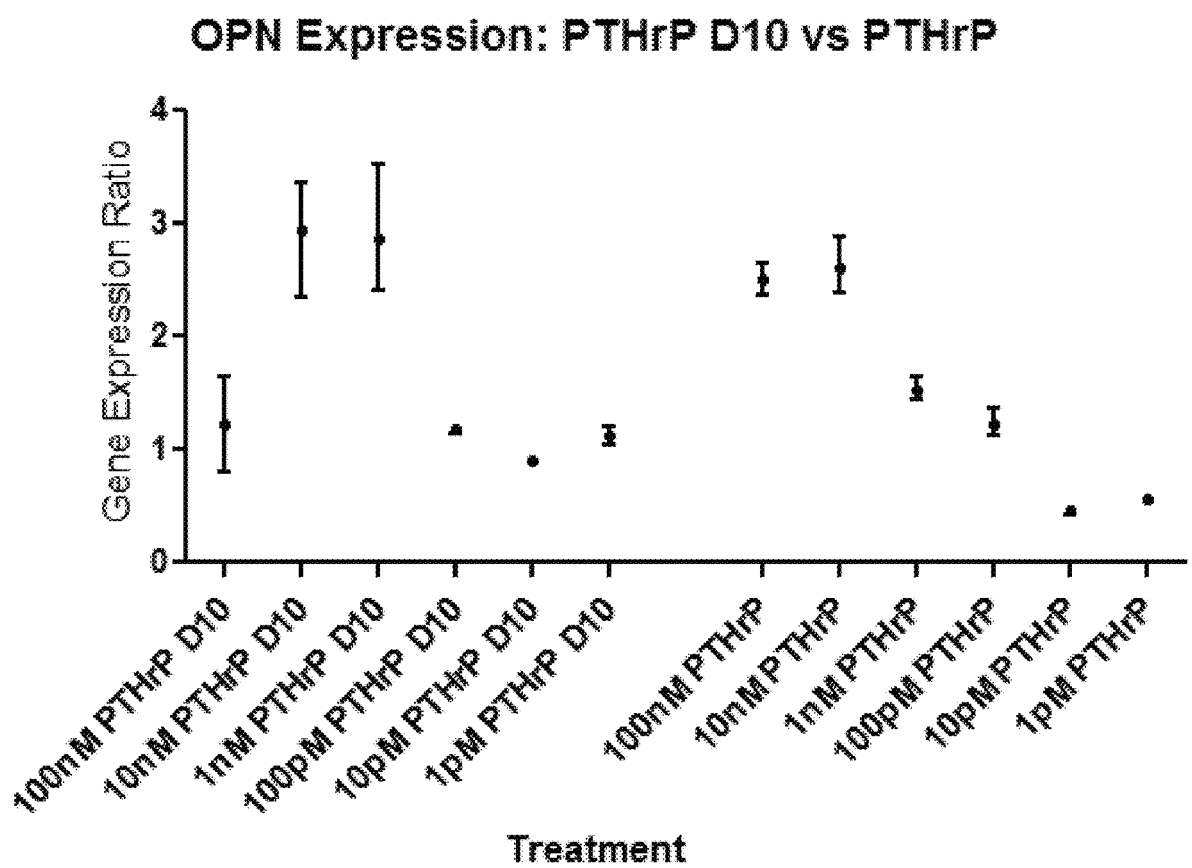
FIG. 5. Graph illustrating osteopontin (OPN) expression ratio for both targeted and non-targeted PTHrP in MC3T3E1 cells. The OPN ratio is calculated by (Treated OPN expression/Vehicle control OPN expression).

Referring now to FIG. 5, osteopontin (OPN) expression ratio for both targeted and non-targeted PTHrP were analyzed in MC3T3E1 cells. The OPN ratio is calculated by (Treated OPN expression/Vehicle control OPN expression). Higher expression levels are associated with greater osteoblast activity and is a key protein involved in bone mineralization. The addition of targeting ligand does not reduce the efficacy of the drug.

Figures 6A, 6B, 6C, 6D:
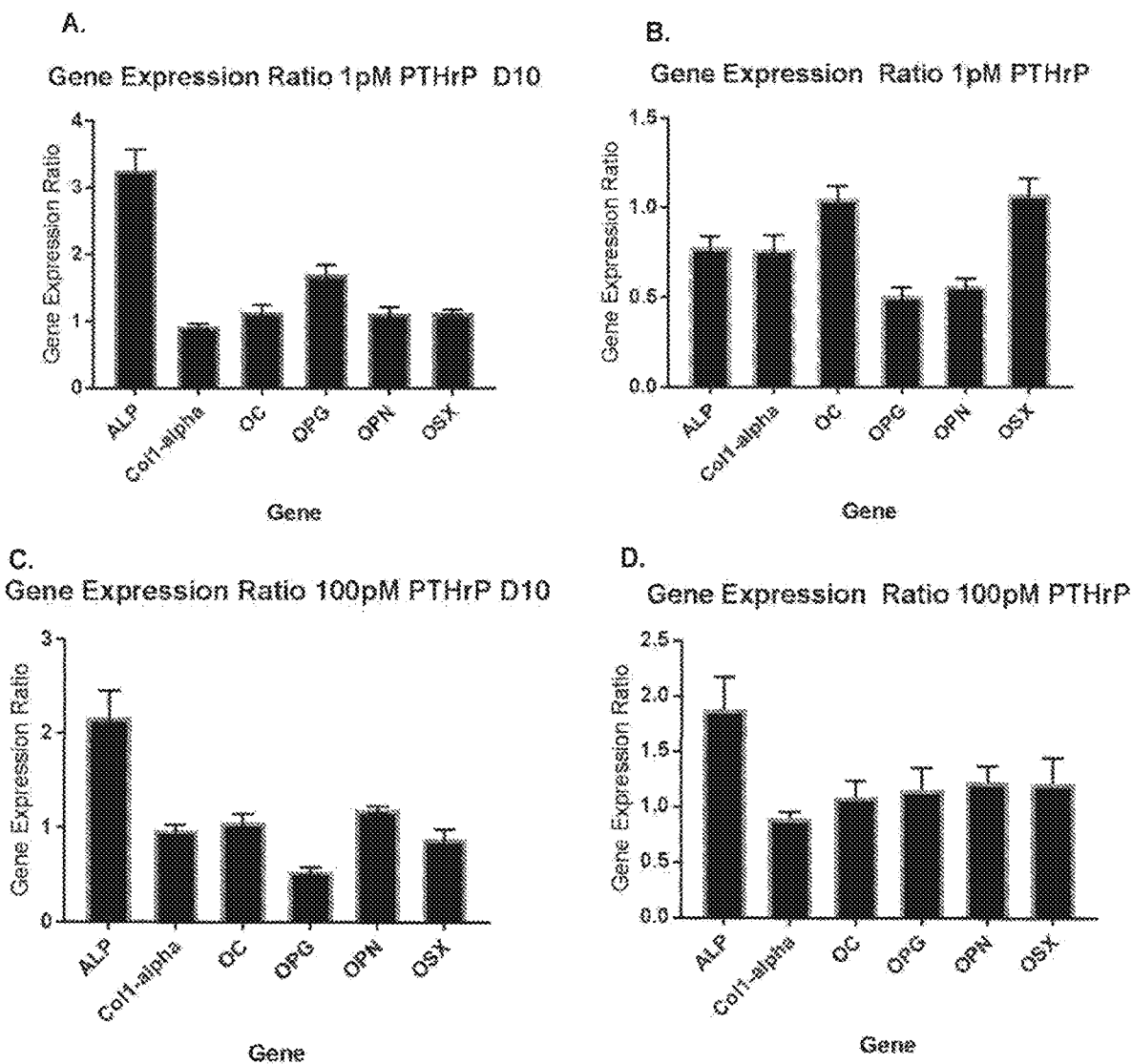
FIGS. 6A-6D. Graphs illustrating gene expression ratio of several key bone markers for both targeted and non-targeted PTHrP in MC3T3E1 cells.

Referring now to FIG. 6, gene expression ratio of several key bone markers for both targeted and non-targeted PTHrP were analyzed in MC3T3E1 cells. Activity markers include alkaline phosphatase (ALP), Collagen I-alpha (Col1-alpha), osteocalcin (OC), osteoprotegerin (OPG), osteopontin (OPN, and Osterix (OSX). The gene expression ratio is calculated by (Treated gene expression/Vehicle control gene expression). The targeted PTHrP has activity as low as 1 pM.

TABLE 1

Effects of the tested compounds on various organs in mice

| Mouse ID | Liver | Kidney |
| --- | --- | --- |
| Targeted Drug | No significant lesions | No significant lesions |
| Targeted Drug | Rare, microscopic mononuclear aggregates (random) | |
| Targeted Drug | No significant lesions | No significant lesions |
| Targeted Drug | Mild to moderate multifocal lymphplasmcytic centrilobular inflammation | No significant lesions |
| Targeted Drug | No significant lesions | Mild lymphoplasmacytic pyelitis |
| Control | No significant lesions | No significant lesions |
| Control | No significant lesions | No significant lesions |
| Control | No significant lesions | Mild lymphoplasmacytic pyelitis |
| Control | No significant lesions | Mild neutrophilic pyelitis |
| Control | Rare, microscopic mononculear aggregates (random) | No significant lesions |

Referring now to Table 1, mice were treated with 31 nmol/kg/day subcutaneous injections of PTHrPD10 ("Targeted Drug") or saline. Swiss ND4 mice were treated for 28 days. Mice were sacrificed at the end of the study and liver and kidneys were excised. Organs were fixed in formalin and paraffin sections were made from each. A veterinary pathologist performed a randomized blind analysis on the organs. No detectable toxicity was observed. the lesion noted are minimal in significance and unassociated with obvious tissue damage (necrosis). It appears unlikely that the type of lesion would cause clinical signs or illness. They are more likely within the normal limits for these animals.

Figure 7:
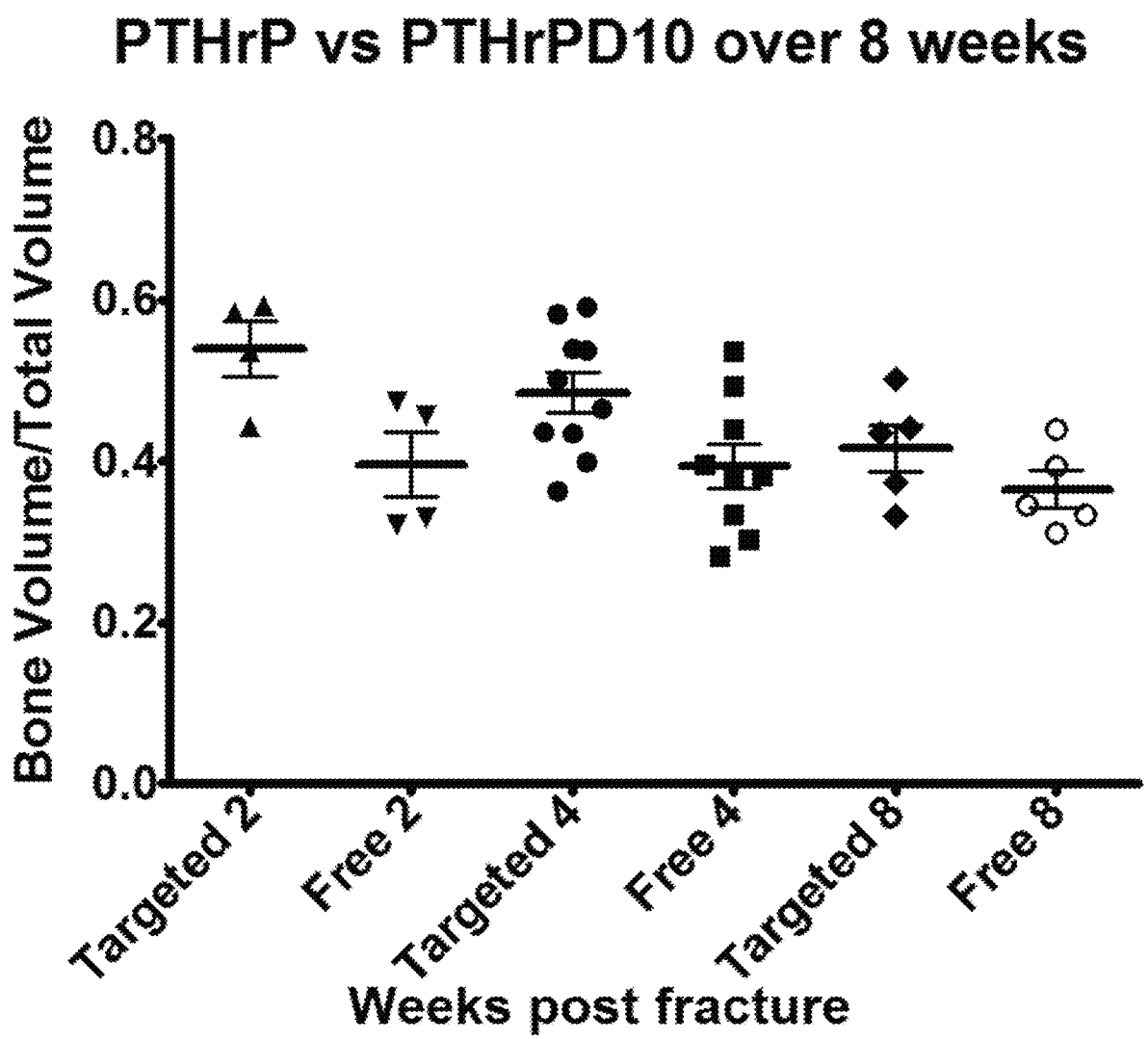
FIG. 7. Graph illustrating the effects of PTHrPD10 (targeted) or PTHrP (free) on bone volume after treatment.

Referring now to FIG. 7, mice were treated with 3 nmol/kg/day subcutaneous injections of PTHrPD10 (targeted) or PTHrP (free). The Swiss ND4 mice were treated for 14, 28, or 56 days. Mice were sacrificed at the end of the dosing period for each study and femurs were excised. Fracture callus densities were measured using a scanco microCT. 100 slice section at the thickest diameter each fracture callus were selected for the measurement. 'Targeted 2' represents mice dosed by targeted PTHrP for 2 weeks (14 days). 'Free 2' represents mice dosed by unmodified PTHrP for 2 weeks (14 days). 'Targeted 4' represents mice dosed by targeted PTHrP for 4 weeks (28 days). 'Free 4' represents mice dosed by unmodified PTHrP for 4 weeks (28 days). 'Targeted 8' represents mice dosed by targeted PTHrP for 8 weeks (56 days). 'Free 8' represents mice dosed by unmodified PTHrP for 8 weeks (56 days). Greater densities can be observed in the targeted PTHrP over the free PTHrp at every time point. The greatest differences between targeted and free PTHrP is at 2 weeks. Those results indicate that the targeted drug not only improves fracture healing but that it also accelerates fracture healing.

Figure 8:
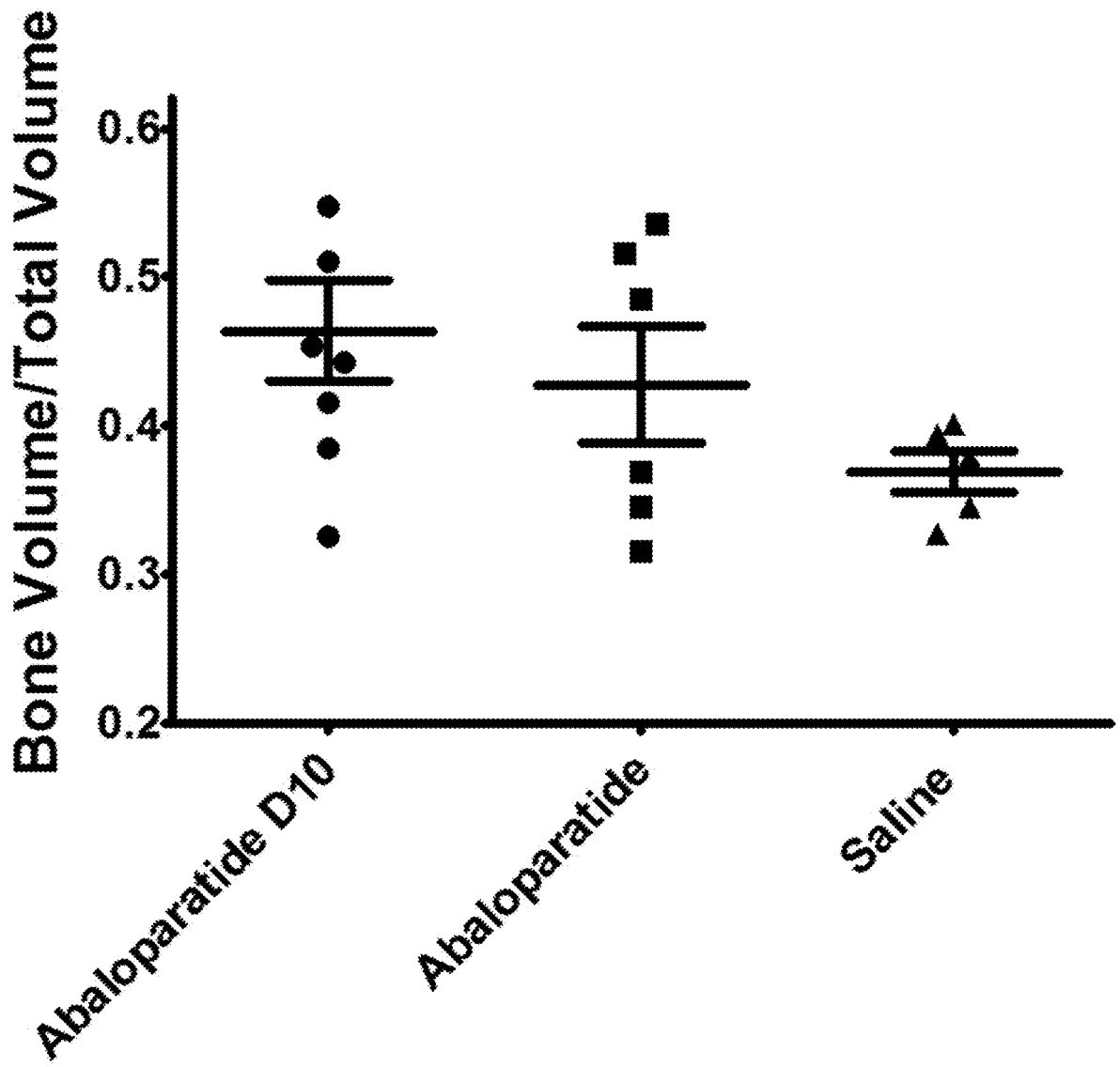
FIG. 8. Graph illustrating the effects of abaloparatide D10 (targeted), abaloparatide (not targeted) and saline on bone volume after treatment.

Referring now to FIG. 8, mice were treated with 31 nmol/kg/day subcutaneous injections of abaloparatide D10 (targeted), abaloparatide (not targeted) and saline. Swiss ND4 mice were treated for 28 days. Mice were sacrificed at the end of the study and femurs were excised. Fracture callus densities were measured using a scanco microCT. 100 slice section at the thickest diameter each fracture callus were selected for the measurement. Abaloparatide has been used previously for the treatment of osteoporosis. These results indicate that Abaloparatide can also be used for treating bone fractures. These results indicate that targeted abaloparatide performs better than free abaloparatide.

Figure 9:
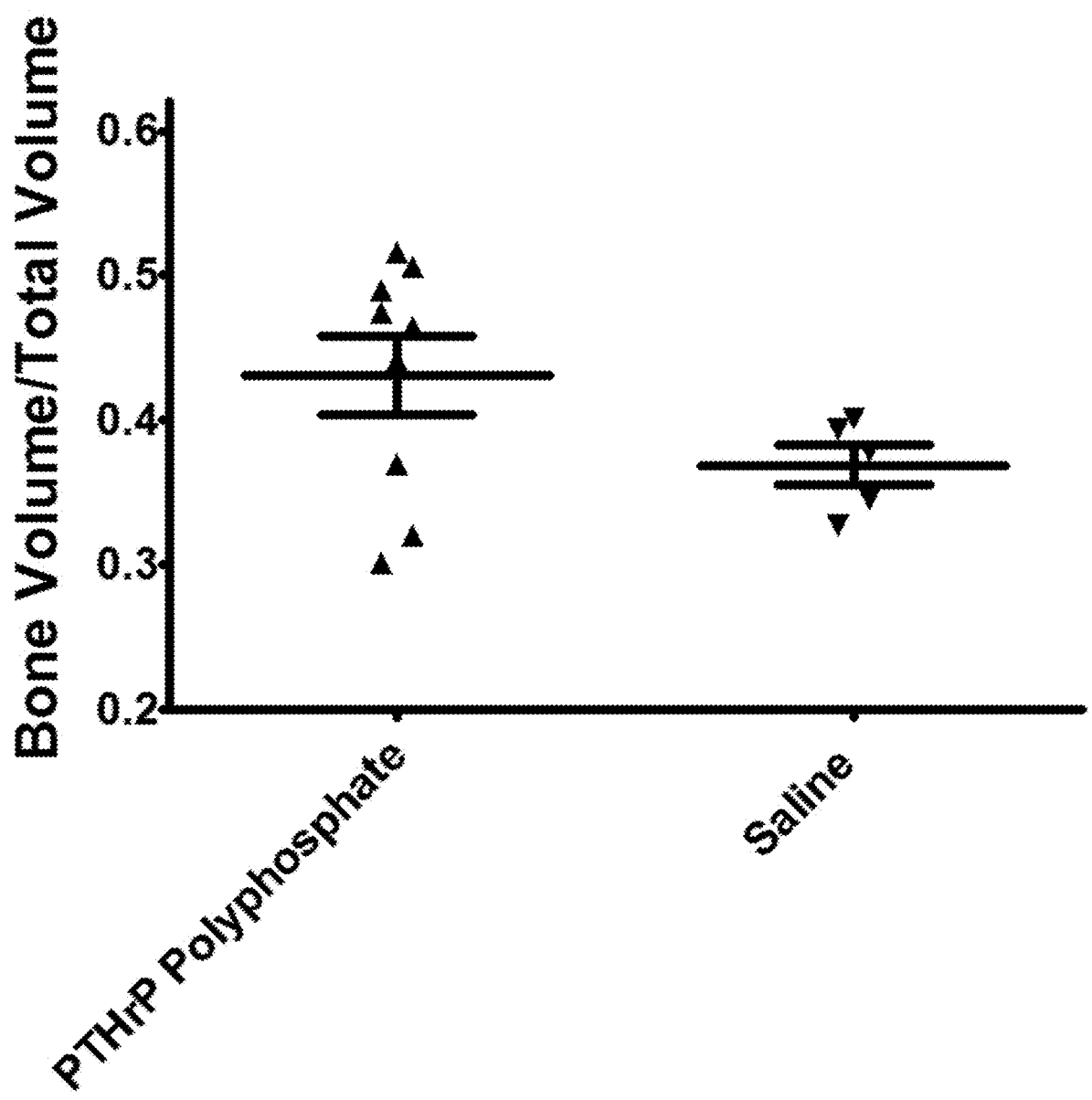
FIG. 9. Graph illustrating the effects of PTHrP targeted with polyphosphate or saline on bone volume after treatment.

Referring now to FIG. 9, mice were treated with 31 nmol/kg/day subcutaneous injections of PTHrP targeted with polyphosphate or saline. Swiss ND4 mice were treated for 28 days. Mice were sacrificed at the end of the study and femurs were excised. Fracture callus densities were measured using a scanco microCT. 100 slice section at the thickest diameter each fracture callus were selected for the measurement. PTHrP targeted with polyphosphate increases fracture healing compared to Saline.

Figure 10:
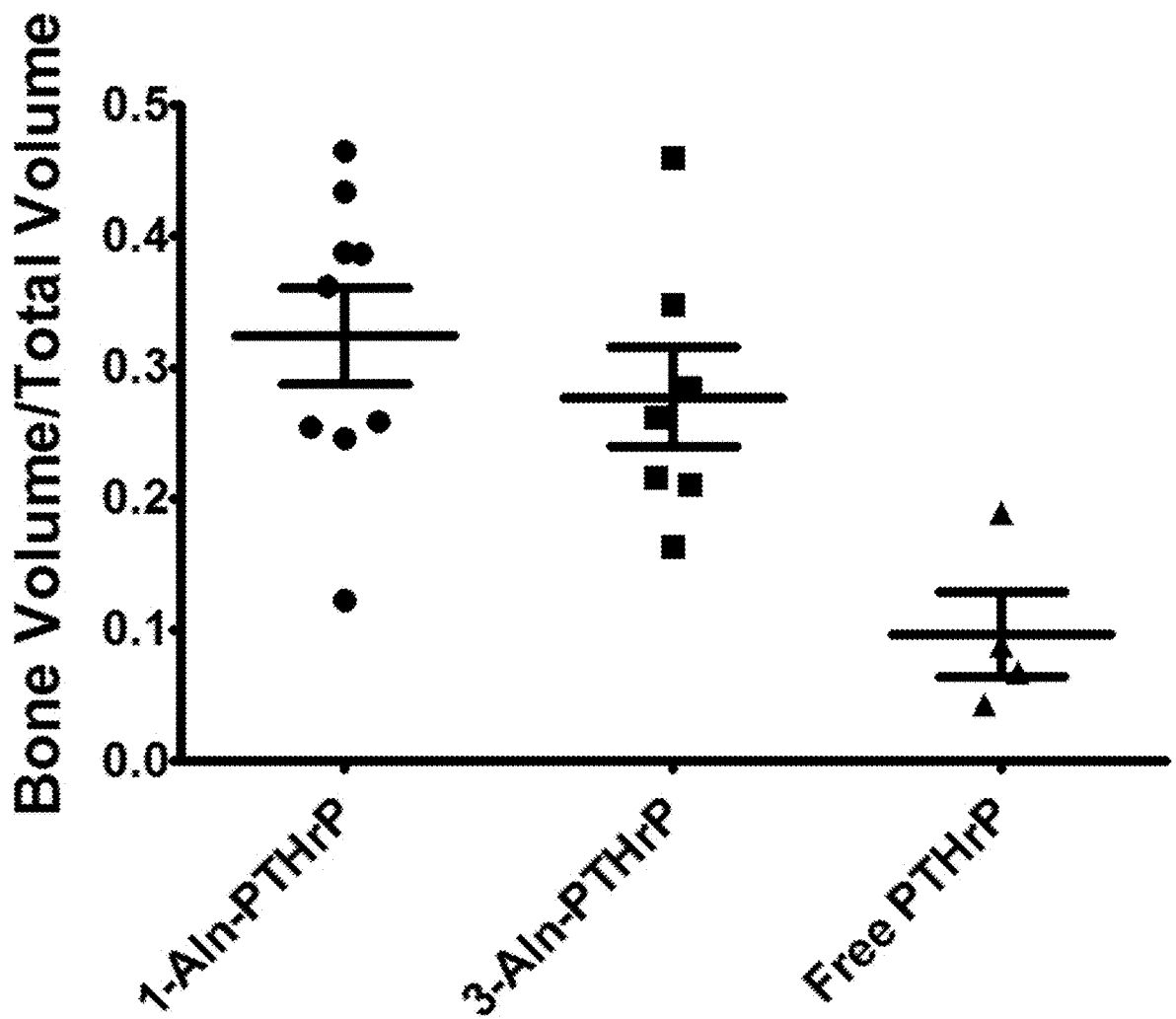
FIG. 10. Graph illustrating the effects of PTHrP targeted with a single alendronate, tri-branched alendronate or free PTHrP on bone volume after treatment.

Referring now to FIG. 10, mice were treated with 31 nmol/kg/day subcutaneous injections of PTHrP targeted with a single alendronate, tri-branched alendronate or free PTHrP. Swiss ND4 mice were treated for 28 days. Mice were sacrificed at the end of the study and femurs were excised. Fracture callus densities were measured using a scanco microCT. 100 slice section at the thickest diameter each fracture callus were selected for the measurement. PTHrP targeted either a single alendronate or tri-branched alendronate increases fracture healing compared to free PTHrP.

Example 4

Figure 11:
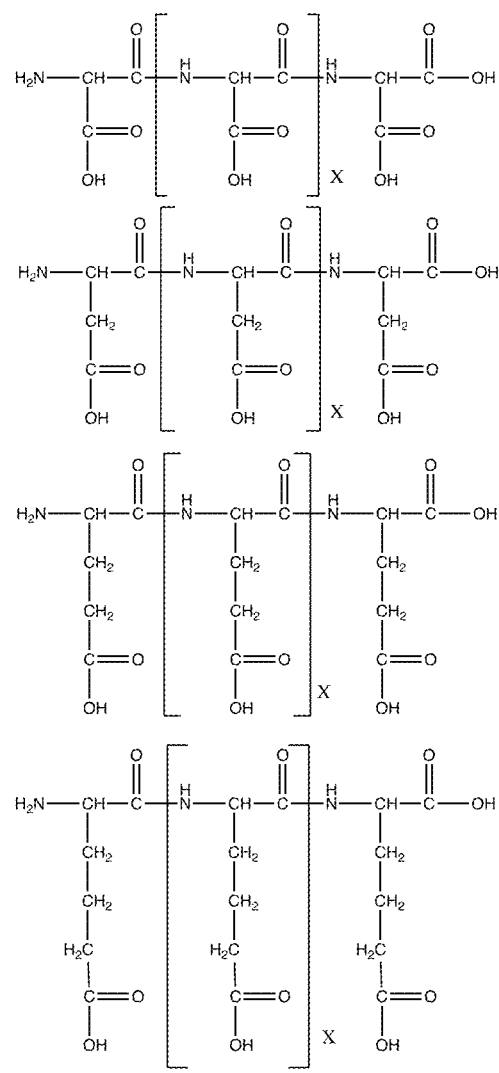
FIG. 11. Chemical formula illustrating linear polymers of acidic amino acids of varying carbon chain length.
Figure 12:
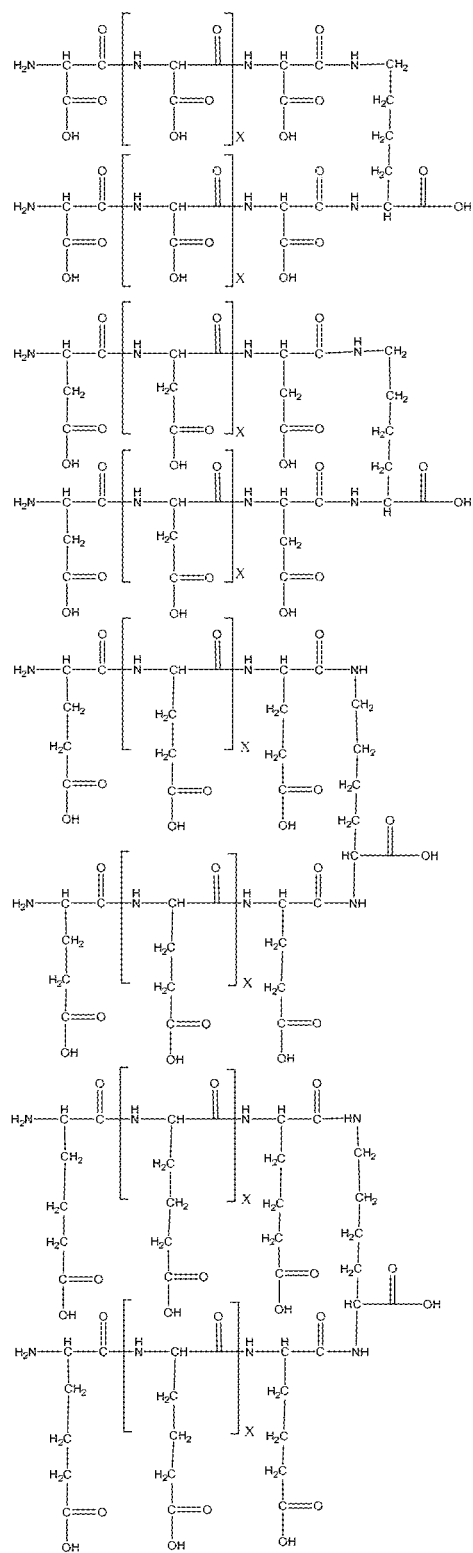
FIG. 12. Chemical formula illustrating branched polymers of acidic amino acids of varying carbon chain length.
Figure 13A:
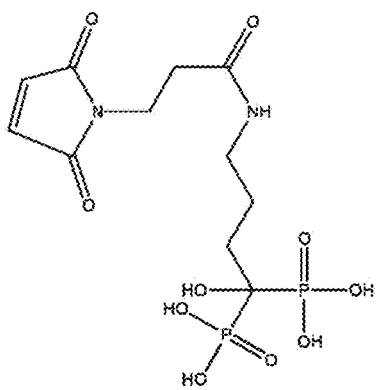
FIGS. 13A-13C. Chemical formulas illustrating non-amino-acid-based bone targeting ligands.
Figure 13B:
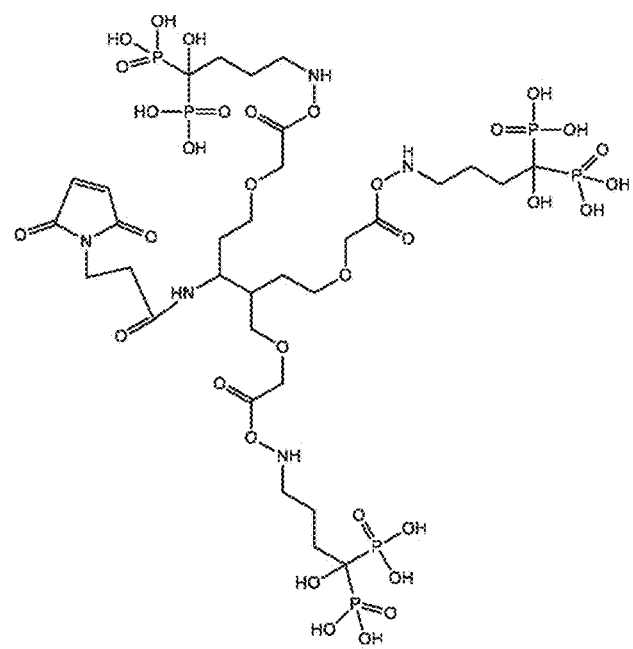
Figure 13C:
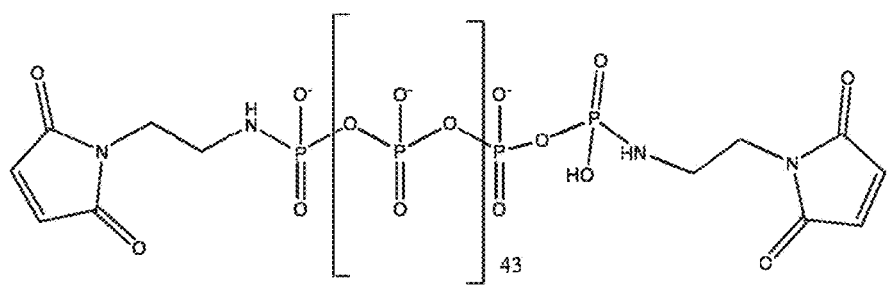

Targeting ligands can include, but are not limited to, oligo acidic amino acids. Exemplary oligo acidic amino acids include, but are not limited to, a linear polymer of 8, 9, 10, 11, 12, 13, 14, 15, 16, 17, 18, 19, 20, 21, 22, 23, 24, 25, 26, 27, 28, 29, and/or 30 aspartic acids comprising L and/or D amino acids, a linear polymer of 8, 9, 10, 11, 12, 13, 14, 15, 16, 17, 18, 19, 20, 21, 22, 23, 24, 25, 26, 27, 28, 29, and/or 30 glutamic acids comprising L and/or D amino acids, a linear polymer of 10 acidic amino acids comprising L and/or D acidic amino acids, a branched polymer of aspartic acids with 4, 5, 6, 7, 8, 9, 10, 11, 12, 13, 14, 15, 16, 17, 18, 19, and/or 20 residues on each branch comprising L and/or D amino acids, a branched polymer of glutamic acids with 4, 5, 6, 7, 8, 9, 10, 11, 12, 13, 14, 15, 16, 17, 18, 19, and/or 20 residues on each branch comprising L and/or D amino acids and/or a branched polymer of acidic amino acids with 4, 5, 6, 7, 8, 9, 10, 11, 12, 13, 14, 15, 16, 17, 18, 19, and/or 20 residues on each branch comprising L and/or D acidic amino acids. Referring now to FIGS. 11-12, exemplary linear and branched polymers of acidic amino acids are shown. FIG. 13 provides exemplary targeting ligands that are not derived from amino acids.

Targeting ligands are coupled with a maleimide-containing linker. The targeting ligands having a maleimide-containing linker are further conjugated with various peptides having distinct chemical properties via a cysteine maleimide coupling process. These peptides can comprise, but are not limited to, a sequence representing a heparin-binding domain of FGF2 (SEQ ID NO: 14), a sequence representing a pituitary adenylate cyclase-activating polypeptide (SEQ ID NO: 15), a sequence representing a chemotactic cryptic peptide derived from the CTX region of collagen type III (SEQ ID NO: 16), a sequence representing a casein kinase 2 beta chain (SEQ ID NO: 17), a sequence representing a osteopontin-derived peptide (SEQ ID NO: 18), and/or a sequence representing a P4-BMP2 (SEQ ID NO: 19). The conjugated peptides are iodinated via Pierce iodination reagent, where $^1$I is covalently bound to the histidine, tyrosine and/or tryptophan residues of the conjugated peptides.

The F109C conjugated with branched D10 has the formula, (see also SEQ ID NO: 70)
YKRSRYTCMalK[DDDDDDDDDD]$_2$.

The PACAPC conjugated with branched D10 has the formula, (see also SEQ ID NO: 71)
HSDGIFTDSYSRYRKQMAVKKYLAAVLGKRYKQRVKNKCMalK.

[DDDDDDDDDD]$_2$.

The CTCC conjugated with branched D10 has the formula, (see also SEQ ID NO: 72)
YIAGVGGEKSGGFYCMalK[DDDDDDDDDD]$_2$.

The Ck2.3C conjugated with branched D10 has the formula, (see also SEQ ID NO: 3)
RQIKIWFQNRRMKWKKIPVGESLKDLIDQCMalK[DDDDDDDDDD]$_2$.

The ODPC conjugated with branched D10 has the formula, (see also SEQ ID NO: 74)
DVDVPDGRGDSLAYGCMalK[DDDDDDDDDD]$_2$.

The P4C conjugated with branched D10 has the formula, (see also SEQ ID NO: 75)
KIPKASSVPTELSAISTLYLCMalK[DDDDDDDDDD]$_2$.

The F109C conjugated with branched E10 has the formula, (see also SEQ ID NO: 76)
YKRSRYTCMalK[EEEEEEEEEE]$_2$.

The PACAPC conjugated with branched E10 has the formula, (see also SEQ ID NO: 77)
HSDGIFTDSYSRYRKQMAVKKYLAAVLGKRYKQRVKNKCMalK

[EEEEEEEEEE]$_2$.

The CTCC conjugated with branched E10 has the formula, (see also SEQ ID NO: 78)
YIAGVGGEKSGGFYCMalK[EEEEEEEEEE]$_2$.

The Ck2.3C conjugated with branched E10 has the formula, (see also SEQ ID NO: 79)
RQIKIWFQNRRMKWKKIPVGESLKDLIDQCMalK[EEEEEEEEEE]$_2$.

The ODPC conjugated with branched E10 has the formula, (see also SEQ ID NO: 80)
DVDVPDGRGDSLAYGCMalK[EEEEEEEEEE]$_2$.

The P4C conjugated with branched E10 has the formula, (see also SEQ ID NO: 81)
KIPKASSVPTELSAISTLYLCMalK[EEEEEEEEEE]$_2$.

Figure 14A:
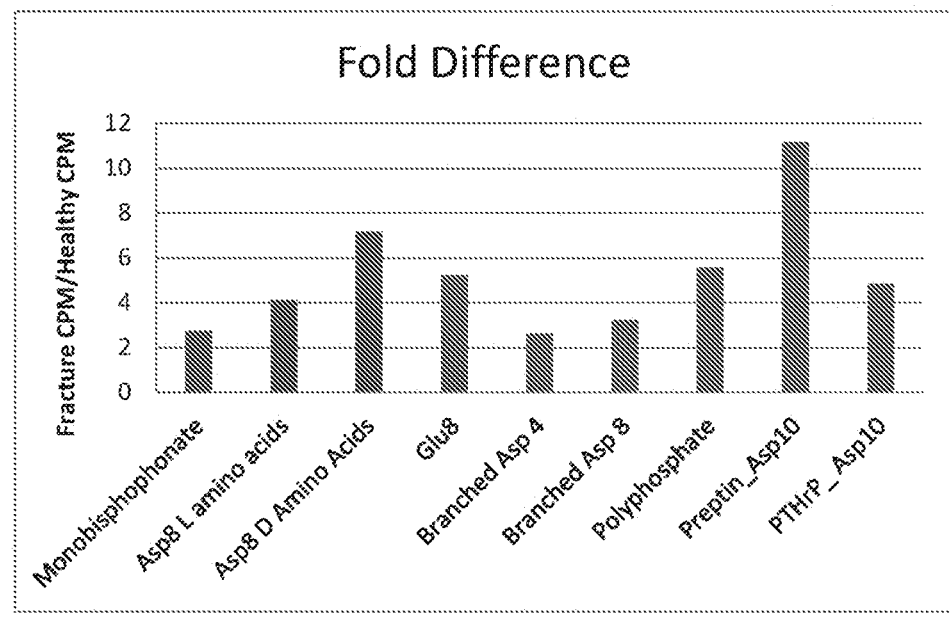
FIG. 14A. Bar graph illustrating the fold difference of relative counts between fractured femur and healthy femur using various targeting ligands radiolabeled with $^{125}$I.
Figure 14B:
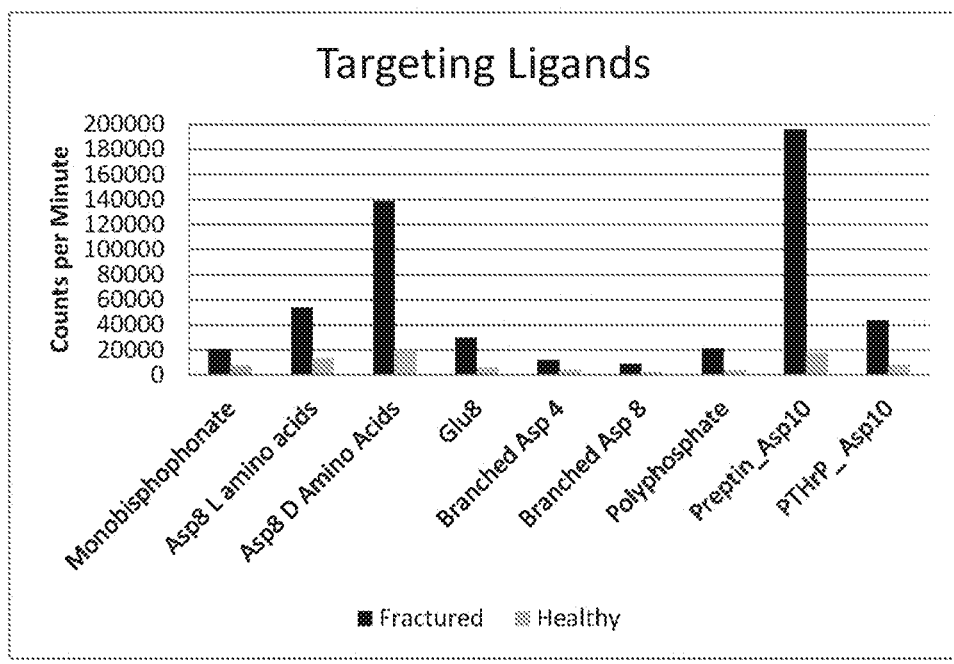
FIG. 14B. Bar graph illustrating the counts per minute of the fractured femur compared to the healthy femur using various targeting ligands radiolabeled with $^{125}$I.

Referring now to FIGS. 14A and 14B, adult female Swiss Weber mice were injected with 1 mCi of $^{125}$I labeled conjugates 10 days post osteotomy. A cysteine tyrosine dipeptide is coupled to a maleimide linker. The cysteine tyrosine dipeptide having a maleimide linker is conjugated to each of the indicated targeting ligands. PTHrP_ASP10 represents a conjugated peptide having 1-46 of PTHrP with a linear polymer of 10 aspartic acids. Preptin_Asp10 represents a conjugated peptide having 1-16 of preptin with a linear polymer of 10 aspartic acids. A necropsy 24 hours post injections was performed and tissues were excised. The tissues were then counted via a gamma counter. The relative counts of the fractured femur over the healthy femur are displayed here as a ratio.

Figure 15:
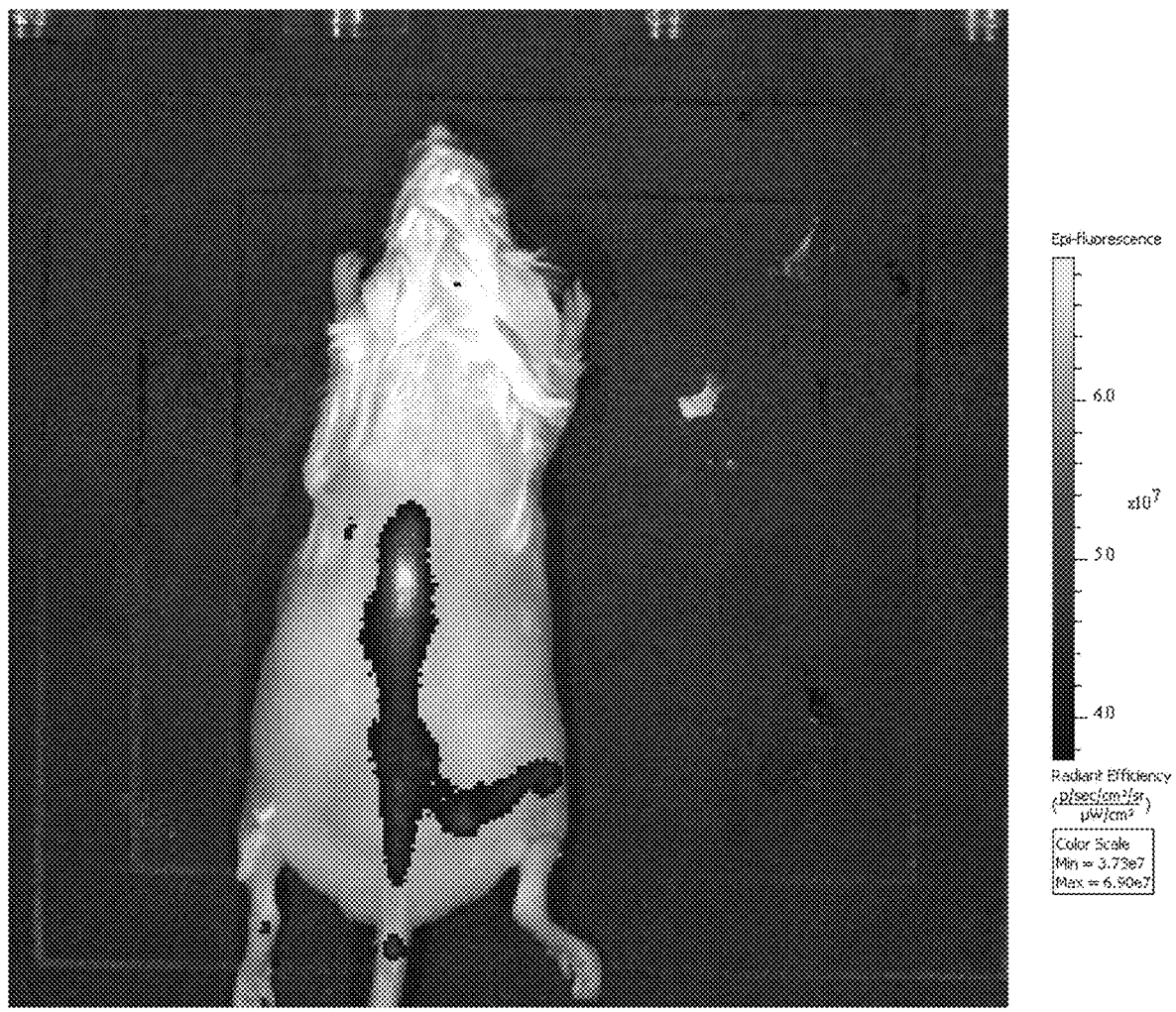
FIG. 15. Near infrared image illustrating the targeting of LS288 conjugated to a linear polymer of 10 L-aspartic acids 10 days post osteotomy on the right femur. Some off target signal is visible along the back due to the injection site.

Referring now to FIG. 15, adult female Swiss Weber mice were injected subcutaneously with LS288 conjugated to a linear polymer of 10 L-aspartic acids 10 days post osteotomy on the right femur. The mouse was imaged via a 1 sec 780 nm excitation beam. Emission fluorescence was collected at 810 nm for 1 second. The injection site was near the back of the mouse, and therefore, the mouse exhibits high fluorescence in the back.

Figure 16:
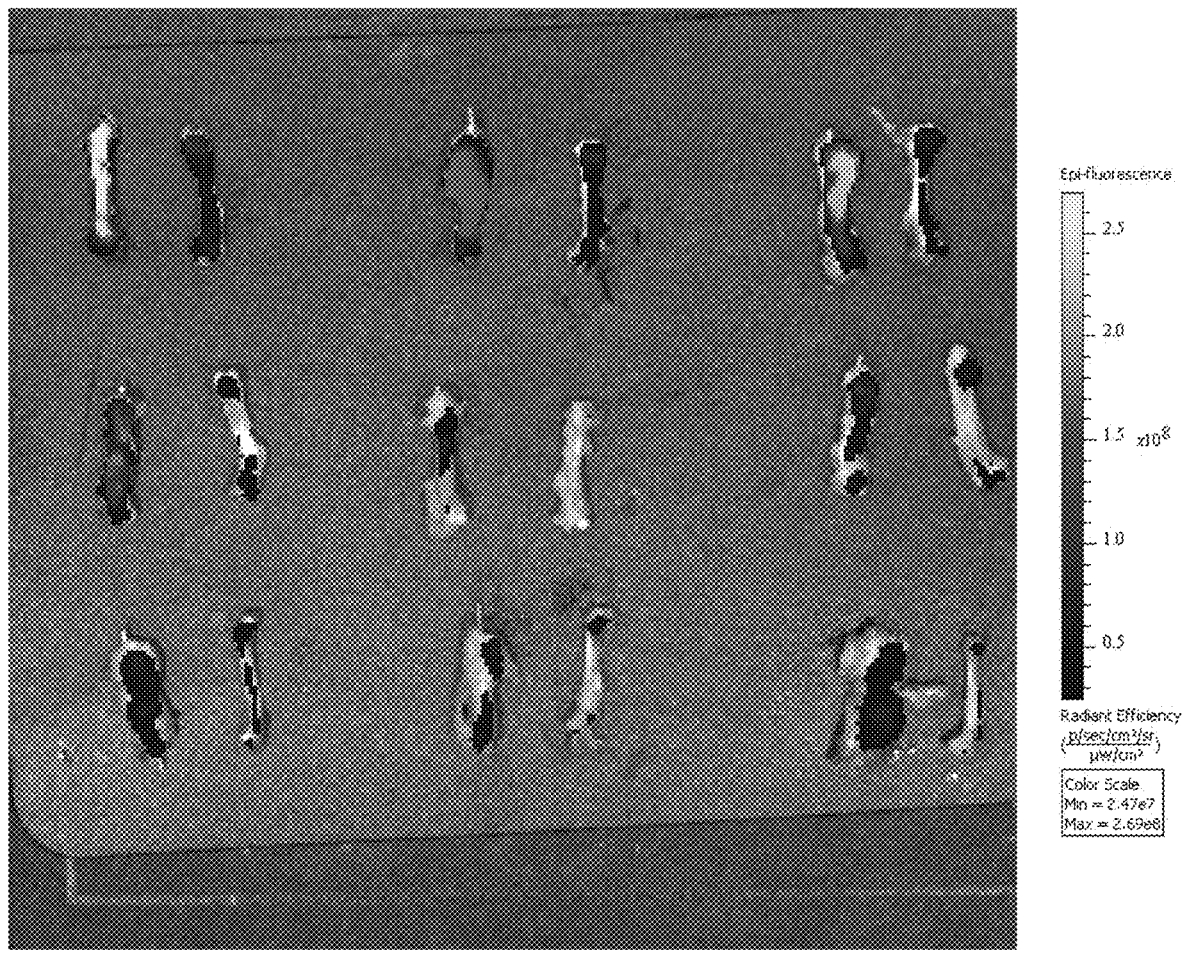
FIG. 16. Near infrared image illustrating the targeting of LS288 conjugated to a linear polymer of 10 L-aspartic acids at 3 (bottom row), 6 (middle row), and 10 days (top row) post osteotomy on the right femur. In each pair of femurs, a femur on the left represents the fractured femur while a femur on the right represents the healthy femur.

Referring now to FIG. 16, adult female Swiss Weber mice were injected subcutaneously with LS288 conjugated to a linear polymer of 10 L-aspartic acids at 3, 6, and 10 days post osteotomy on the right femur. The mouse was imaged via a 1-second 780 nm excitation beam. Emission fluorescence was collected at 810 nm for 1 second. The top row represents 10 days post fracture, the middle row represents 6 days post fracture, and the bottom row represents 3 days post fracture. The femur on the left in every group is the fractured femur compared to the healthy femur on the right. This demonstrates that fracture targeting improves during the healing process.

Figure 17A:
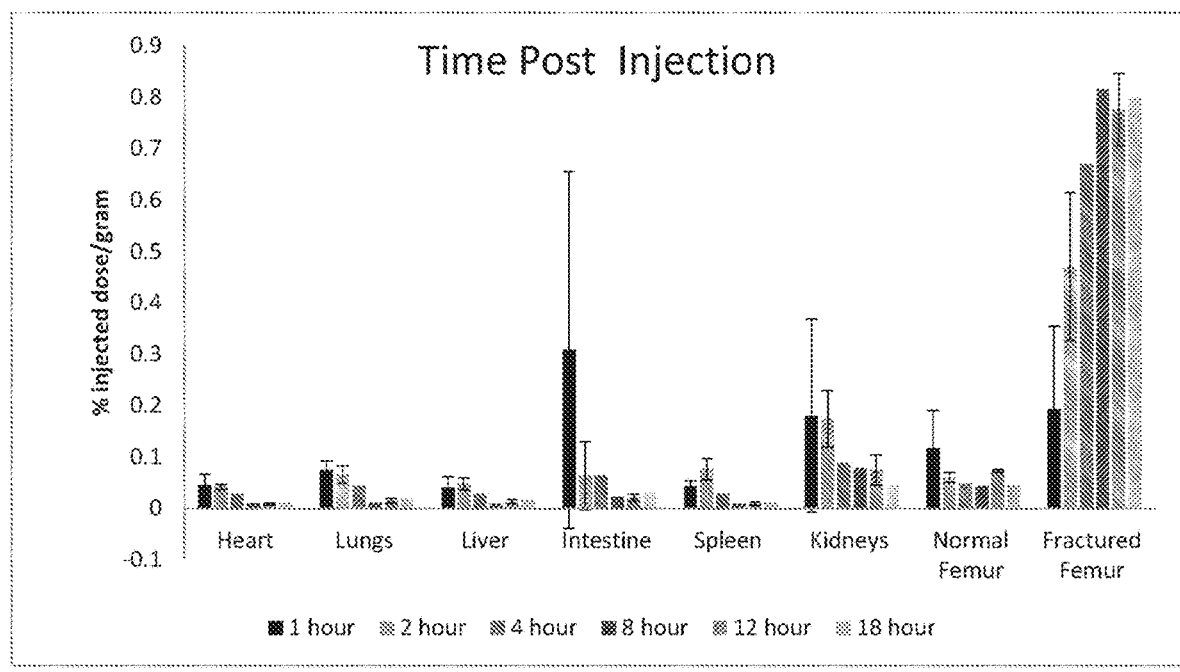
FIG. 17A. Bar graph illustrating the relative distribution of the radiolabeled conjugated peptide, PreptinD10, as a percent of the total counts that was found in each of the individual organs. The counts are standardized per gram of tissue weight.
Figure 17B:
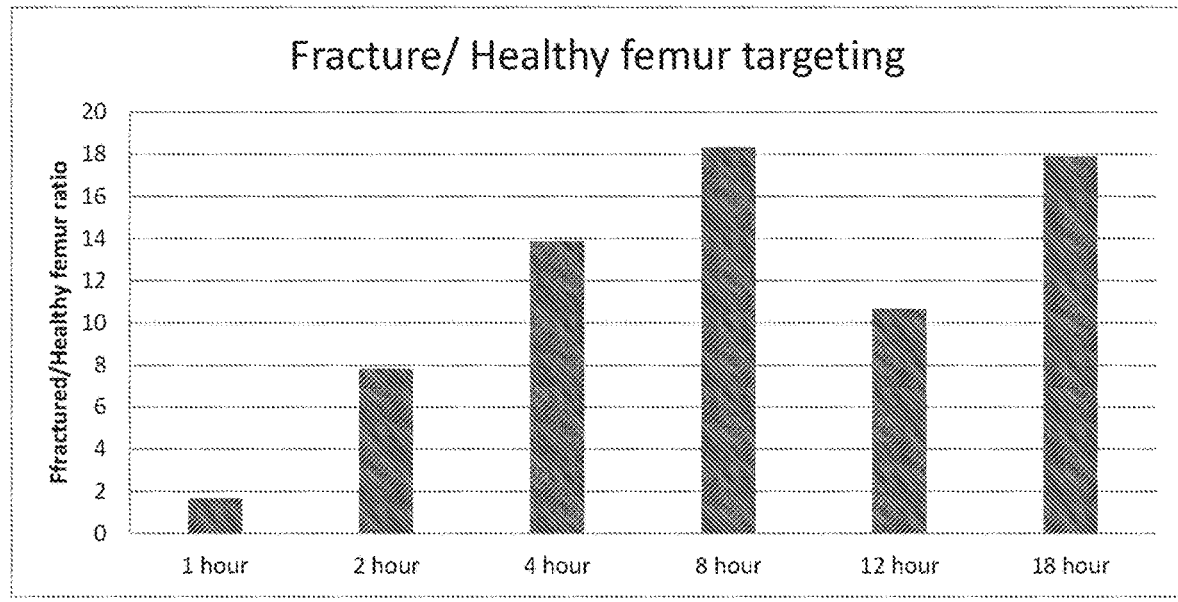
FIG. 17B. Bar graph illustrating the fold difference of relative counts between fractured femur and healthy femur using radiolabeled $^{125}$I PreptinD10.

Referring now to FIG. 17, adult Swiss Weber mice were injected with 0.25 mCi of radiolabeled $^{125}$I PreptinD10 conjugate 10 days post osteotomy and sacrificed at the different time points. Each tissue was collected and then quantified with a gamma counter (FIG. 17A). Fold difference of relative counts between fractured femur and healthy femur using radiolabeled $^{125}$I PreptinD10 were calculated at different time points (FIG. 17B).

Figures 18A, 18B, 18C:
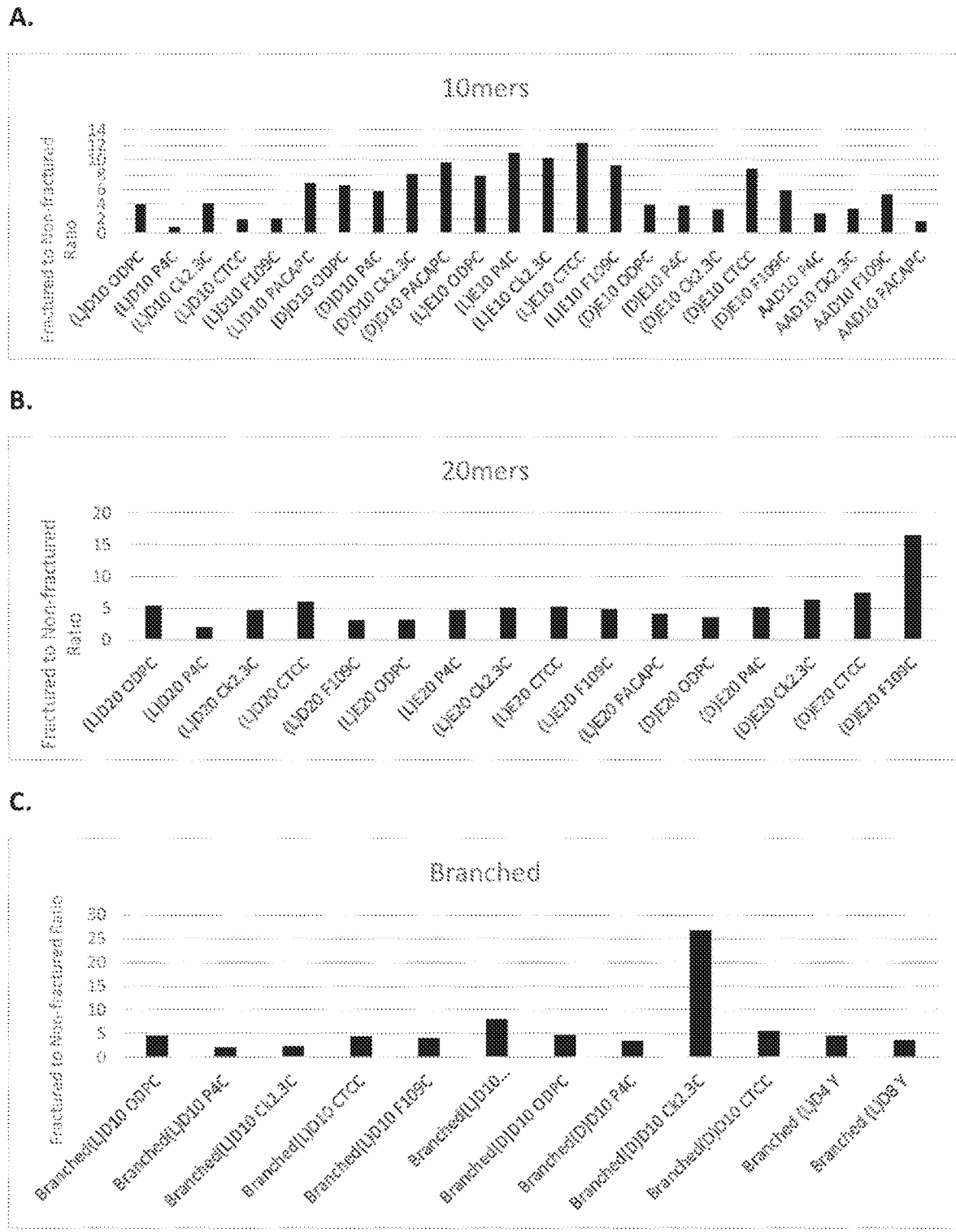
FIG. 18A. Bar graph illustrating the fold difference of relative counts between fractured femur and healthy (non-fractured) femur using various radiolabeled $^{125}$I peptides conjugated with L-Asp10, D-Asp10, L-Glu10, or D-Glu10.
FIG. 18B. Bar graph illustrating the fold difference of relative counts between fractured femur and healthy (non-fractured) femur using various radiolabeled $^{125}$I peptides conjugated with L-Asp20, L-Glu20, or D-Glu20.
FIG. 18C. Bar graph illustrating the fold difference of relative counts between fractured femur and healthy (non-fractured) femur using various radiolabeled $^{125}$I peptides conjugated with branched L-Asp10, branched D-Asp10, branched L-Asp4, or branched L-Asp8.
Figure 19A:
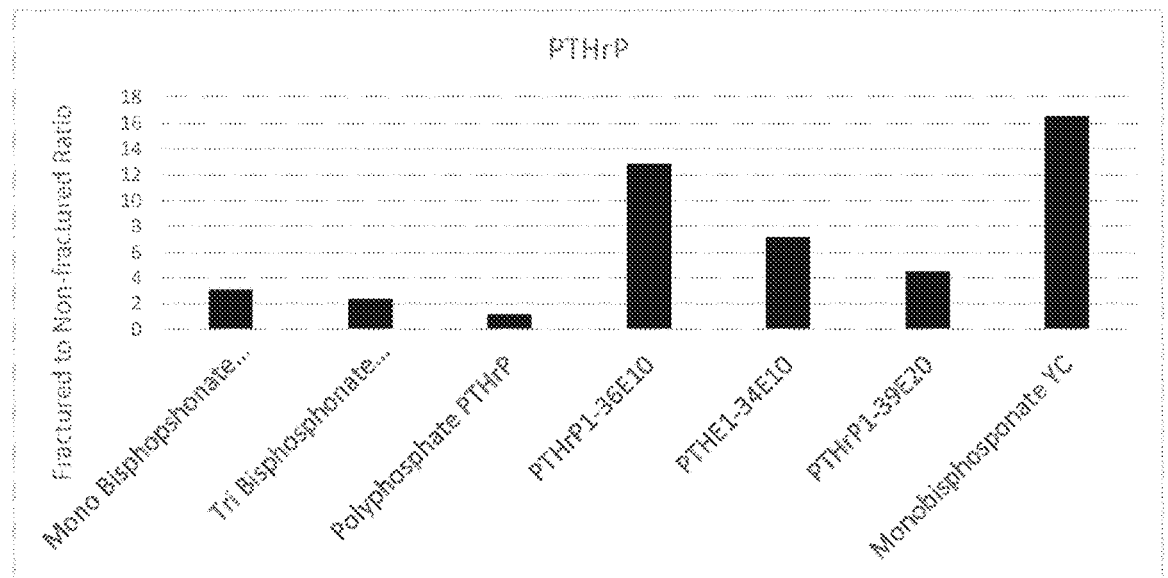
FIG. 19A. Bar graph illustrating the fold difference of relative counts between fractured femur and healthy (non-fractured) femur using various conjugated peptides radiolabeled with $^{125}$I.
Figure 19B:
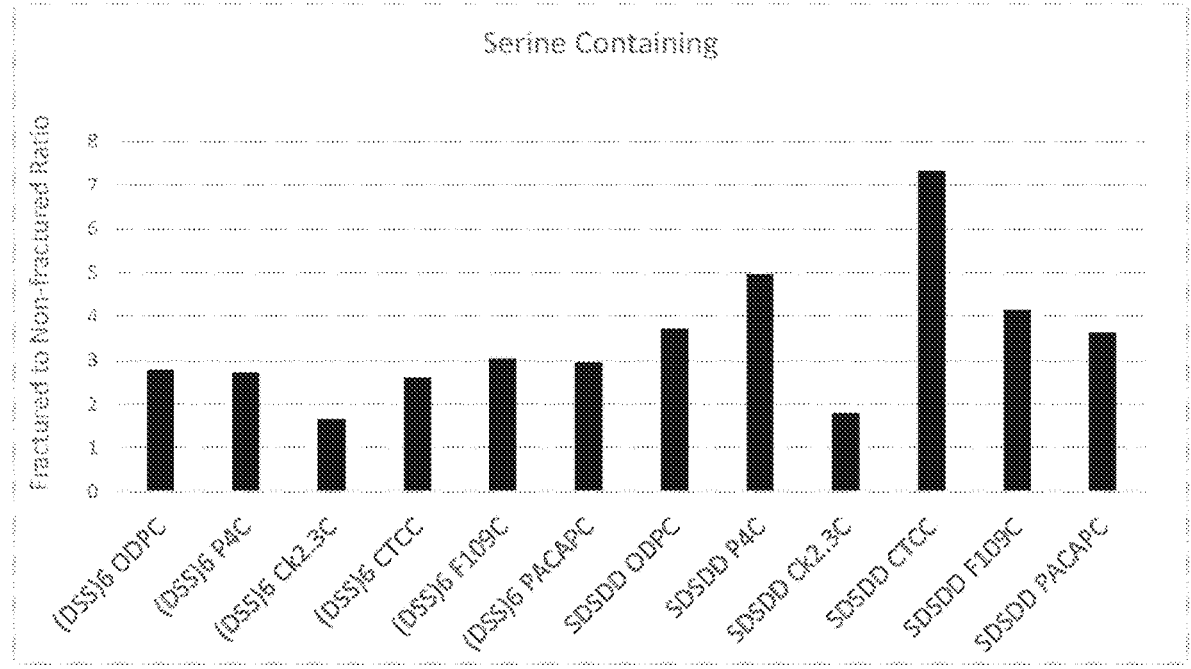
FIG. 19B. Bar graph illustrating the fold difference of relative counts between fractured femur and healthy (non-fractured) femur using various conjugated peptides radiolabeled with $^{125}$I.

Referring now to FIGS. 18 and 19, adult female Swiss Weber mice (12 weeks old) were injected with 0.22 mCi of radiolabeled $^{125}$I conjugated peptides 10 days post osteotomy. 14 hours post injection each mouse was sacrificed and each of the listed organs were collected and quantified. The counts were standardized to the weight of the samples. Fold difference of relative counts between fractured femur and healthy (non-fractured) femur for each conjugated peptides were calculated.

Figure 20A:
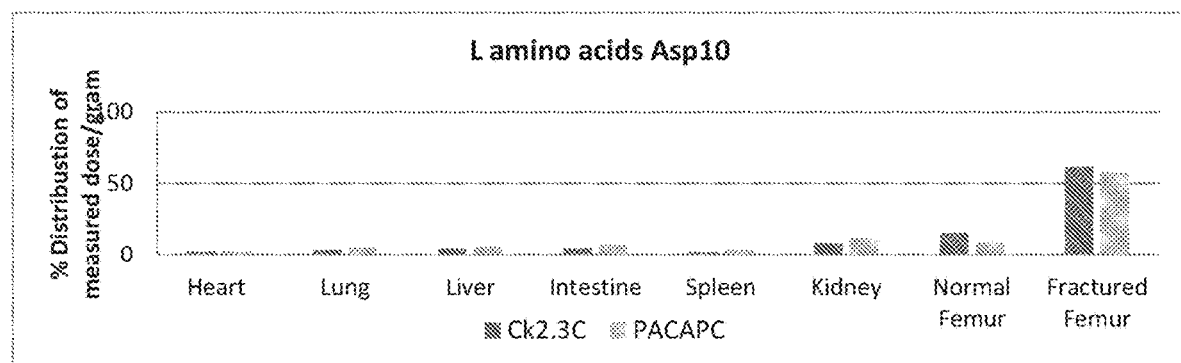
FIG. 20A. Bar graph illustrating the relative distribution of the radiolabeled $^{125}$I peptides (e.g., Ck2.3C and PACAPC) conjugated with L-Asp10 (i.e., a liner polymer of 10 L-aspartic acids) as a percent of the total counts that was found in each of the individual organs.
Figure 20B:
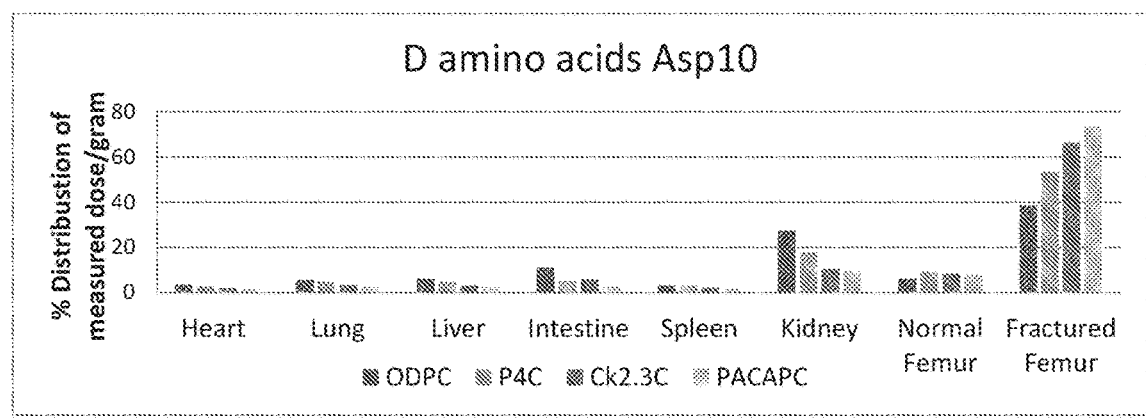
FIG. 20B. Bar graph illustrating the relative distribution of the radiolabeled $^{125}$I peptides (e.g., ODPC, P4C, Ck2.3C, and PACAPC) conjugated with D-Asp10 (i.e., a liner polymer of 10 D-aspartic acids) as a percent of the total counts that was found in each of the individual organs.
Figure 20C:
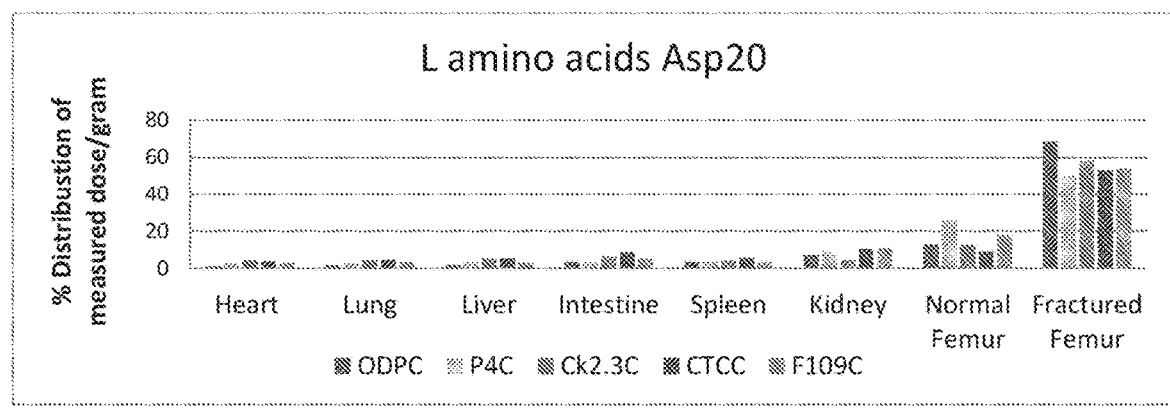
FIG. 20C. Bar graph illustrating the relative distribution of the radiolabeled $^{125}$I peptides (e.g., ODPC, P4C, Ck2.3C, CTCC, and F109C) conjugated with L-Asp20 (i.e., a liner polymer of 20 L-aspartic acids) as a percent of the total counts that was found in each of the individual organs. The counts are standardized per gram of tissue weight.

Referring now to FIG. 20, adult female Swiss Weber mice (12 weeks old) were injected with 0.22 mCi of radiolabeled $^{125}$I peptides (e.g., ODPC, P4C, Ck2.3C, CTCC, F109C, and PACAPC) conjugated with L-Asp10 (FIG. 20A), D-Asp10 (FIG. 20B), or L-Asp20 (FIG. 20C) 10 days post osteotomy. 14 hours post injection each mouse was sacrificed and each of the listed organs were collected and quantified. The counts were standardized to the weight of the samples. All of the conjugated peptides tested exhibited preferential and/or selective targeting towards to fractured bone over other organs.

Figure 21A:
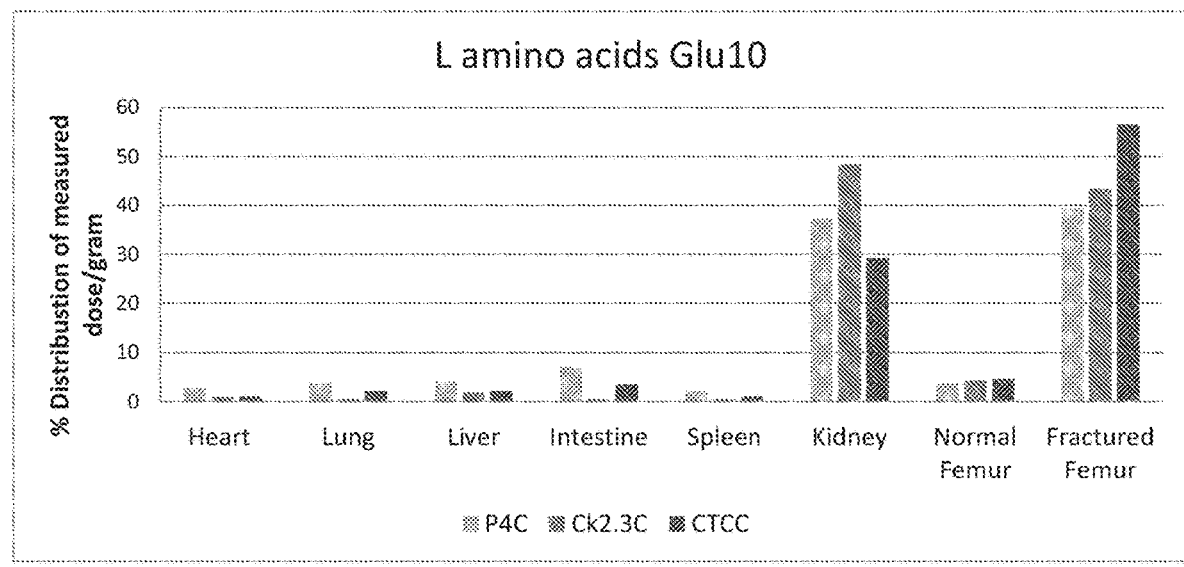
FIG. 21A. Bar graph illustrating the relative distribution of the radiolabeled uI peptides (e.g., P4C, Ck2.3C, and CTCC) conjugated with L-Glu10 (i.e., a liner polymer of 10 L-glutamic acids) as a percent of the total counts that was found in each of the individual organs. The counts are standardized per gram of tissue weight.
Figure 21B:
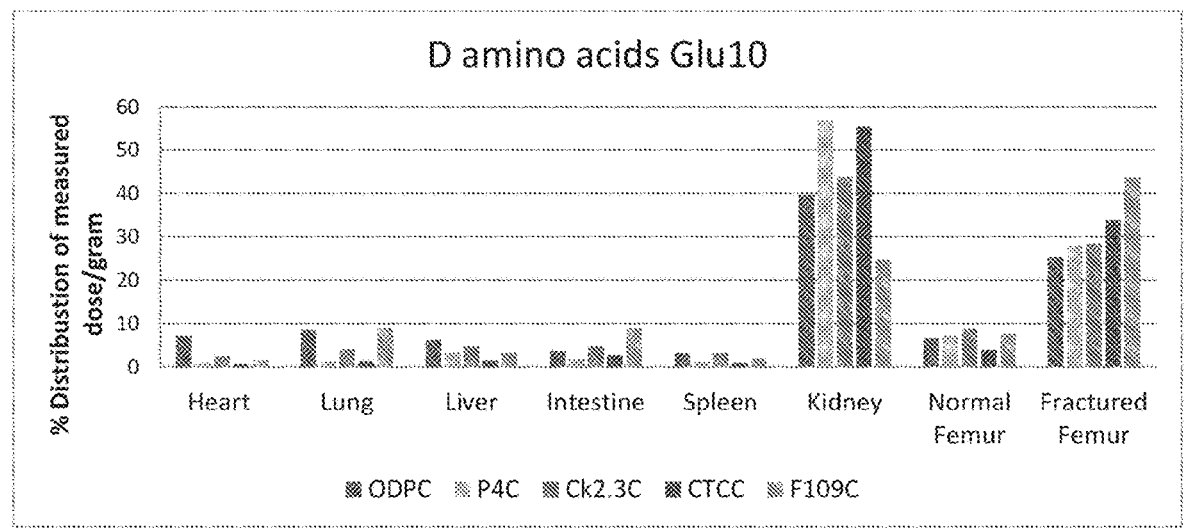
FIG. 21B. Bar graph illustrating the relative distribution of the radiolabeled uI peptides (e.g., ODPC, P4C, Ck2.3C, CTCC, and F109C) conjugated with D-Glu10 (i.e., a liner polymer of 10 D-glutamic acids) as a percent of the total counts that was found in each of the individual organs. The counts are standardized per gram of tissue weight.

Referring now to FIG. 21, adult female Swiss Weber mice (12 weeks old) were injected with 0.22 mCi of radiolabeled $^{125}$I peptides (e.g., ODPC, P4C, Ck2.3C, CTCC, and F109C) conjugated with L-Glu0 (FIG. 21A) or D-Glu10 (FIG. 21B) 10 days post osteotomy. 14 hours post injection each mouse was sacrificed and each of the listed organs were collected and quantified. The counts were standardized to the weight of the samples. All of the conjugated peptides tested exhibited preferential and/or selective targeting towards to fractured bone over other organs. Higher signal observed in kidney may be due to the high abundance of glutamate transporters on the kidneys. These transporters are responsible for reabsorption of glutamic acid back into circulation, rather than actual uptake in the cell. This means that the signal will likely degrade over time as opposed to the uptake observed in the fractured femur, where the negatively charged molecules will adhere strongly to the bone (see e.g., FIG. 17). See for more details regarding absorption of glutamic acids, Hediger, M. A. Glutamate transporters in kidney and brain. *Am. J. Physiol.—Ren. Physiol.* 277, F487-F492 (1999); Kanai, Y. & Hediger, M. A. Primary structure and functional characterization of a high-affinity glutamate transporter. *Nature* 360, 467-471 (1992); and Kanai, Y. & Hediger, M. A. The glutamate and neutral amino acid transporter family: physiological and pharmacological implications. *Eur. J. Pharmacol.* 479, 237-247 (2003).

Figure 22A:
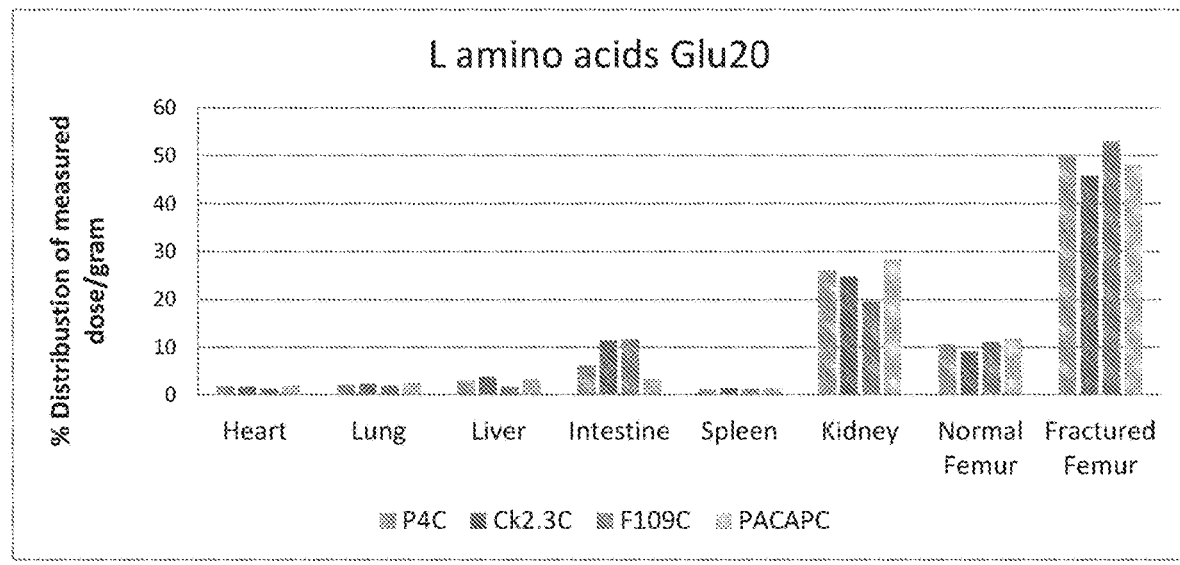
FIG. 22A. Bar graph illustrating the relative distribution of the radiolabeled uI peptides (e.g., P4C, Ck2.3C, F109C, and PACAPC) conjugated with L-Glu20 (i.e., a liner polymer of 20 L-glutamic acids) as a percent of the total counts that was found in each of the individual organs. The counts are standardized per gram of tissue weight.
Figure 22B:
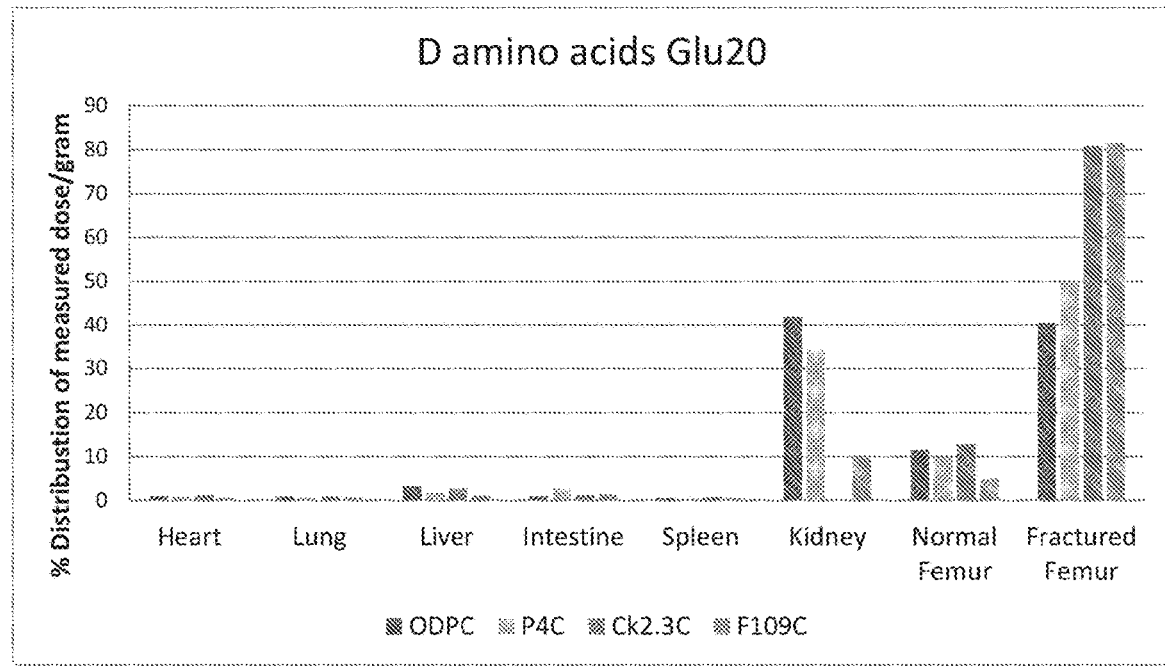
FIG. 22B. Bar graph illustrating the relative distribution of the radiolabeled $^{125}$I peptides (e.g., ODPC, P4C, Ck2.3C, and F109C) conjugated with D-Glu20 (i.e., a liner polymer of 20 D-glutamic acids) as a percent of the total counts that was found in each of the individual organs. The counts are standardized per gram of tissue weight.

Referring now to FIG. 22, adult female Swiss Weber mice (12 weeks old) were injected with 0.22 mCi of radiolabeled $^{125}$I peptides (e.g., ODPC, P4C, Ck2.3C, CTCC, F109C, and PACAPC) conjugated with L-Glu20 (FIG. 22A) or D-Glu20 (FIG. 22B) 10 days post osteotomy. 14 hours post injection each mouse was sacrificed and each of the listed organs were collected and quantified. The counts were standardized to the weight of the samples. Most of the conjugated peptides tested exhibited preferential and/or selective targeting towards to fractured bone or kidney over other organs. Extending the glutamic polymers to 20 appeared to improve the selectivity towards fractured bone slightly but the kidney uptake is still maintained.

Figure 23A:
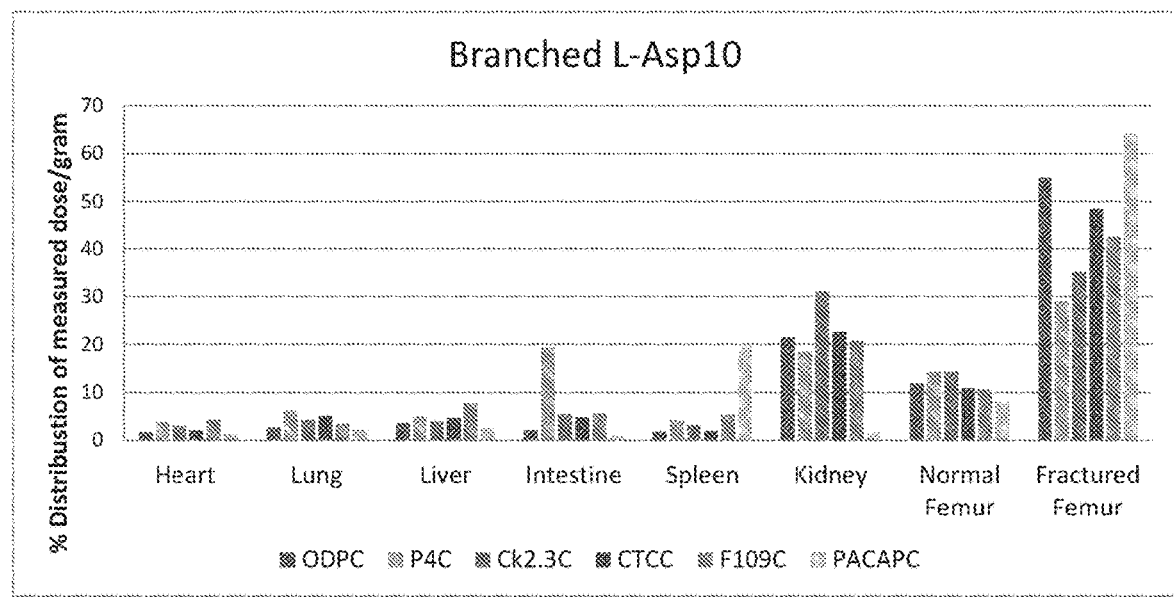
FIG. 23A. Bar graph illustrating the relative distribution of the radiolabeled $^{125}$I peptides (e.g., ODPC, P4C, Ck2.3C, CTCC, F109C, and PACAPC) conjugated with branched L-Asp10 (i.e., a branched polymer of 10 L-aspartic acids) as a percent of the total counts that was found in each of the individual organs. The counts are standardized per gram of tissue weight.
Figure 23B:
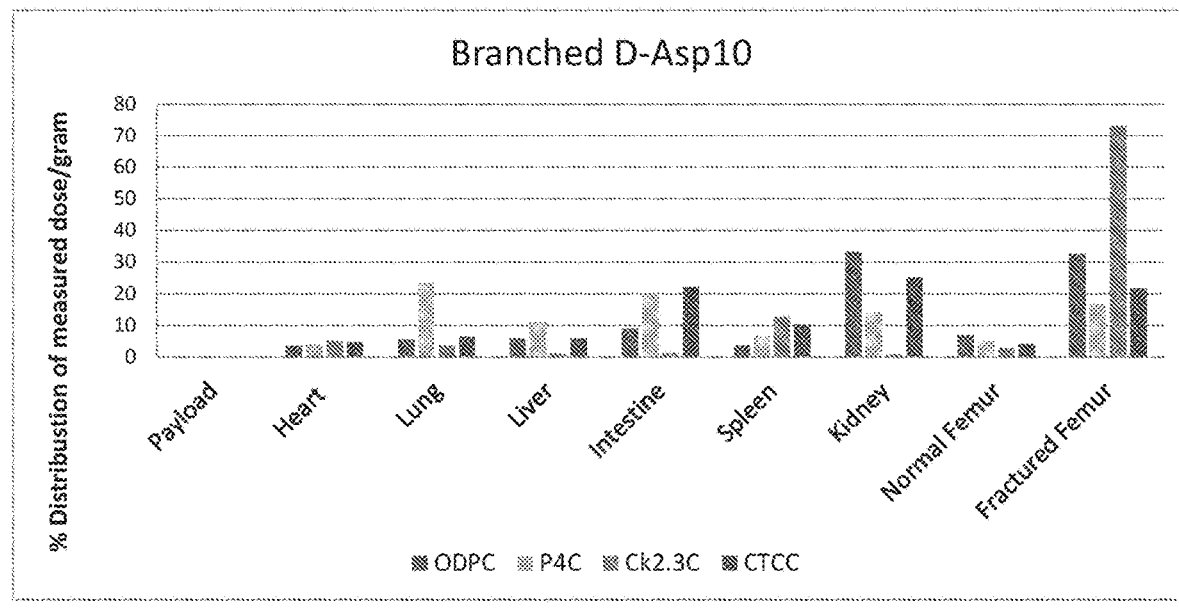
FIG. 23B. Bar graph illustrating the relative distribution of the radiolabeled $^{125}$I peptides (e.g., ODPC, P4C, Ck2.3C, and CTCC) conjugated with branched D-Asp10 (i.e., a branched polymer of 10 D-aspartic acids) as a percent of the total counts that was found in each of the individual organs. The counts are standardized per gram of tissue weight.

Referring now to FIG. 23, adult female Swiss Weber mice (12 weeks old) were injected with 0.22 mCi of radiolabeled $^{125}$I peptides (e.g., ODPC, P4C, Ck2.3C, CTCC, F109C, and PACAPC) conjugated with branched L-Asp10 (FIG. 23A) or branched D-Asp10 (FIG. 23B) 10 days post osteotomy. 14 hours post injection each mouse was sacrificed and each of the listed organs were collected and quantified. The counts were standardized to the weight of the samples. All of the conjugated peptides tested exhibited preferential and/or selective targeting towards to fractured bone over other organs. Some appeared to have higher uptake in the kidneys.

Figure 24A:
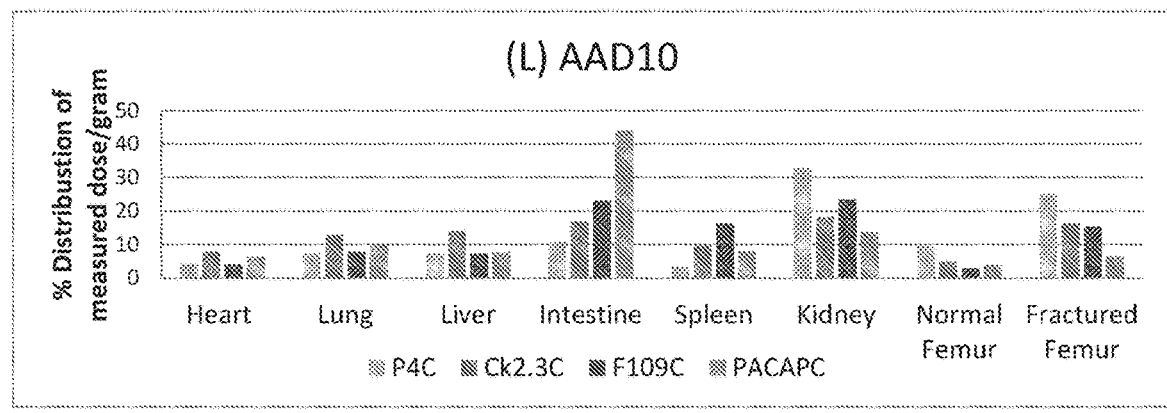
FIG. 24A. Bar graph illustrating the relative distribution of the radiolabeled $^{125}$I peptides (e.g., P4C, Ck2.3C, F109C, and PACAPC) conjugated with L-AAD10 (i.e., 10 L-amino adipic acid liner polymer) as a percent of the total counts that was found in each of the individual organs. The counts are standardized per gram of tissue weight.
Figure 24B:
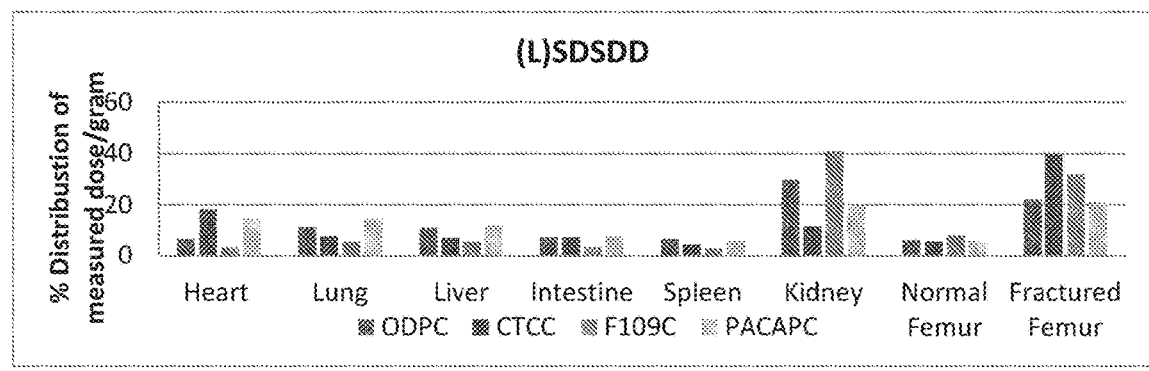
FIG. 24B. Bar graph illustrating the relative distribution of the radiolabeled $^{125}$I peptides (e.g., ODPC, CTCC, F109C, and PACAPC) conjugated with L-SDSDD (i.e., a linear polymer having L-Ser-Asp-Ser-Asp-Asp; SEQ ID NO: 21) as a percent of the total counts that was found in each of the individual organs. The counts are standardized per gram of tissue weight.
Figure 24C:
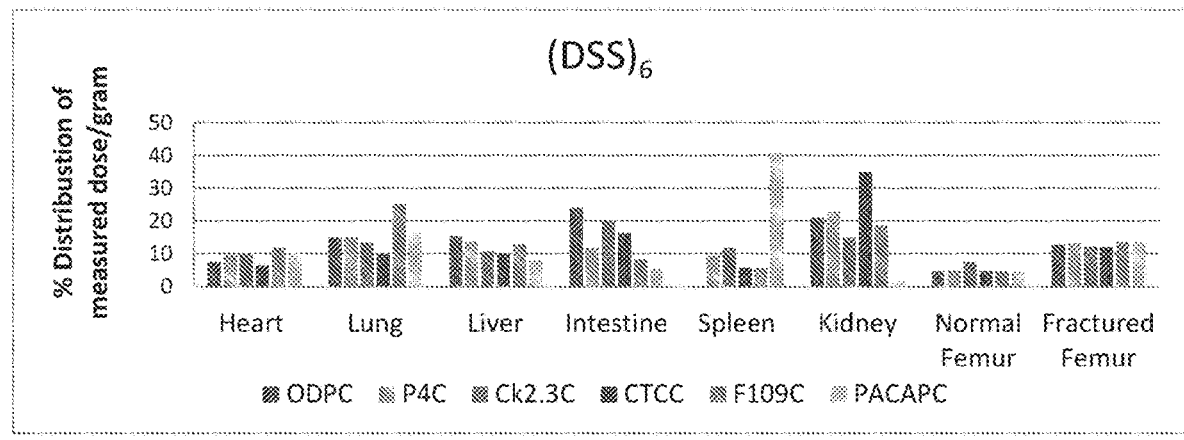
FIG. 24C. Bar graph illustrating the relative distribution of the radiolabeled $^{125}$I peptides (e.g., ODPC, P4C, Ck2.3C, CTCC, F109C, and PACAPC) conjugated with $(DSS)_6$ (i.e., DSSDSSDSSDSSDSSDSS; SEQ ID NO: 22) as a percent of the total counts that was found in each of the individual organs. The counts are standardized per gram of tissue weight.

Referring now to FIG. 24, adult female Swiss Weber mice (12 weeks old) were injected with 0.22 mCi of radiolabeled $^{125}$I peptides (e.g., ODPC, P4C, Ck2.3C, CTCC, F109C, and PACAPC) conjugated with L-AAD10 (FIG. 24A), L-SDSDD (FIG. 24B), or (DSS)$_6$ (FIG. 24C) 10 days post osteotomy. 14 hours post injection each mouse was sacrificed and each of the listed organs were collected and quantified. The counts were standardized to the weight of the samples. Peptides conjugated with L-AAD10 appear to have some targeting ability towards to fractured bone. Peptides conjugated with L-SDSDD exhibited moderate targeting ability towards to fractured bone, and increased uptake in kidney was also observed. Peptides conjugated with (DSS)$_6$ do not appear to have any targeting ability towards to fractured bone.

Figure 25A:
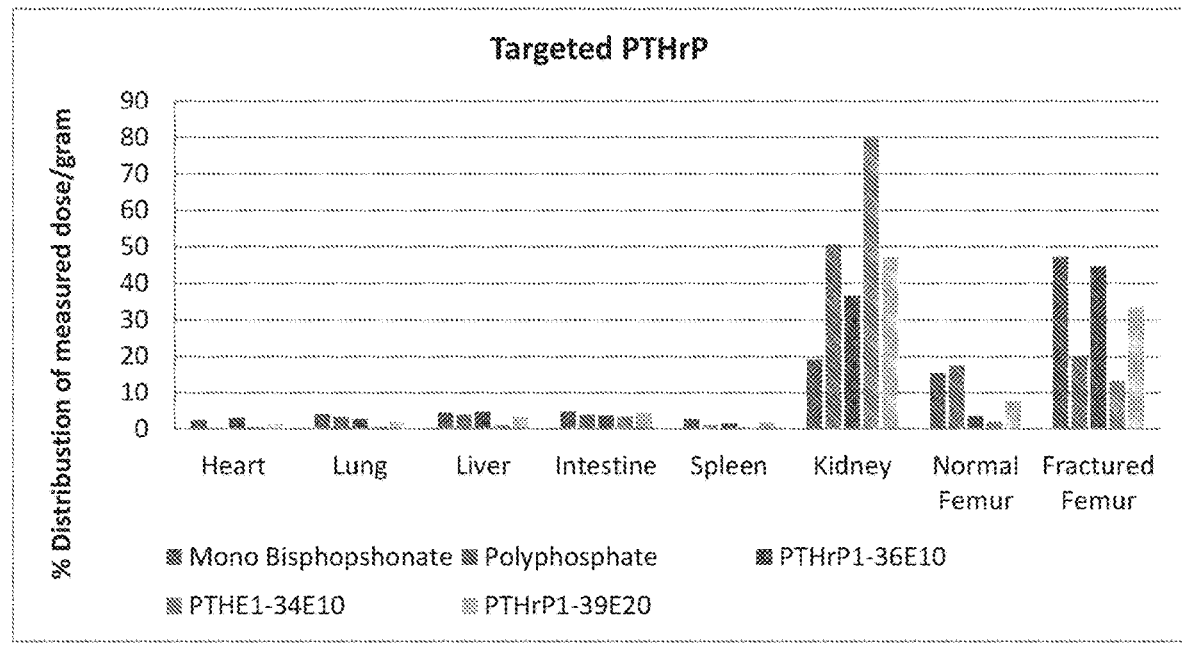
FIG. 25A. Bar graph illustrating the relative distribution of the radiolabeled $^{125}$I PTHrP1-39C conjugated with a mono-bisphosphonate, a tri-bisphosphonate, or a polyphosphate, radiolabeled $^{125}$I PTH1-34 conjugated with E10, and radiolabeled $^{25}$I PTHrP-39 conjugated with E20. PTHrP-39C is PTHrP-39 with a cysteine (C) at the 40 position, to which the different targeting ligands were conjugated. The counts are standardized per gram of tissue weight.
Figure 25B:
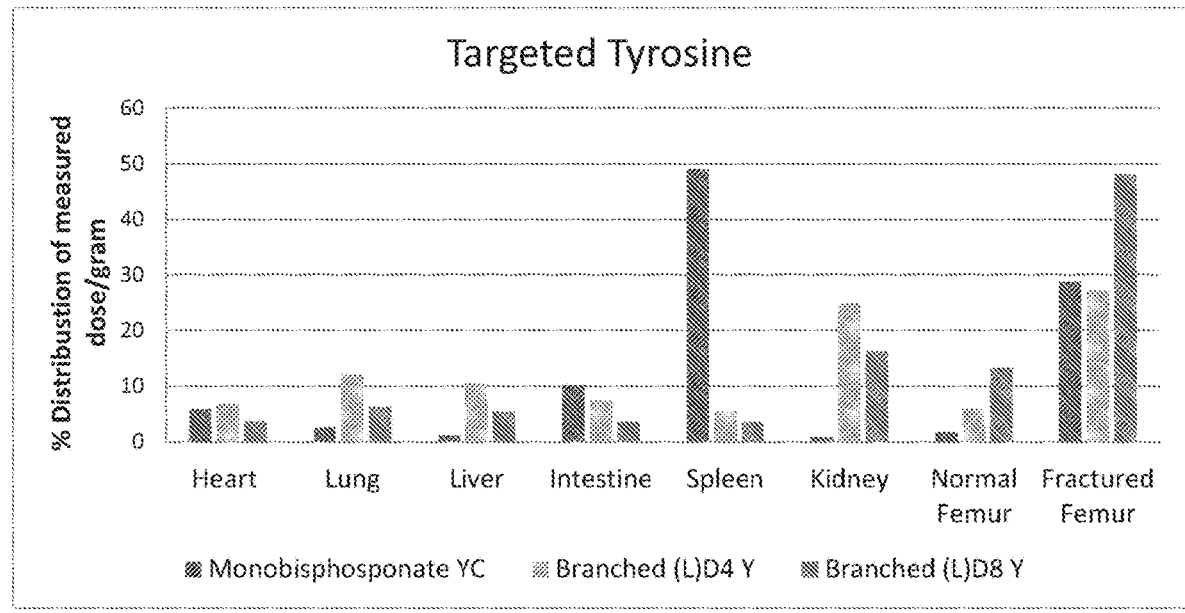
FIG. 25B. Bar graph illustrating the relative distribution of the radiolabeled $^{125}$I Tyrosine conjugated with a mono-bisphosphonate, a branched L-Asp4 (i.e., YPegK[DDDD]$_2$; see also SEQ ID NO:68), or a branched L-Asp8 (i.e., YPegK[DDDDDDDD]$_2$; see also SEQ ID NO:69). "Mono-bisphosphonate YC" is a peptide having tyrosine and cysteine that is conjugated with a mono-bisphosphonate. The counts are standardized per gram of tissue weight.

Referring now to FIG. 25A, adult female Swiss Weber mice (12 weeks old) were injected with 0.22 mCi of radiolabeled $^{125}$I peptides (e.g., PTHrP1-36, and PTH1-34, and PTHrP1-39) conjugated with mono-bisphosphonate, tri-bisphosphonate, polyphosphate, E10, or E20, 10 days post osteotomy. Referring now to FIG. 25B, adult female Swiss Weber mice (12 weeks old) were injected with 0.22 mCi of radiolabeled $^{125}$I tyrosine conjugated with mono-bisphosphonate ("Monobisphosphonate YC"), branched L-Asp4 ("Branched (L)D4 Y"), or branched L-Asp8 ("Branched (L)D8 Y"), 10 days post osteotomy.

Figure 26:
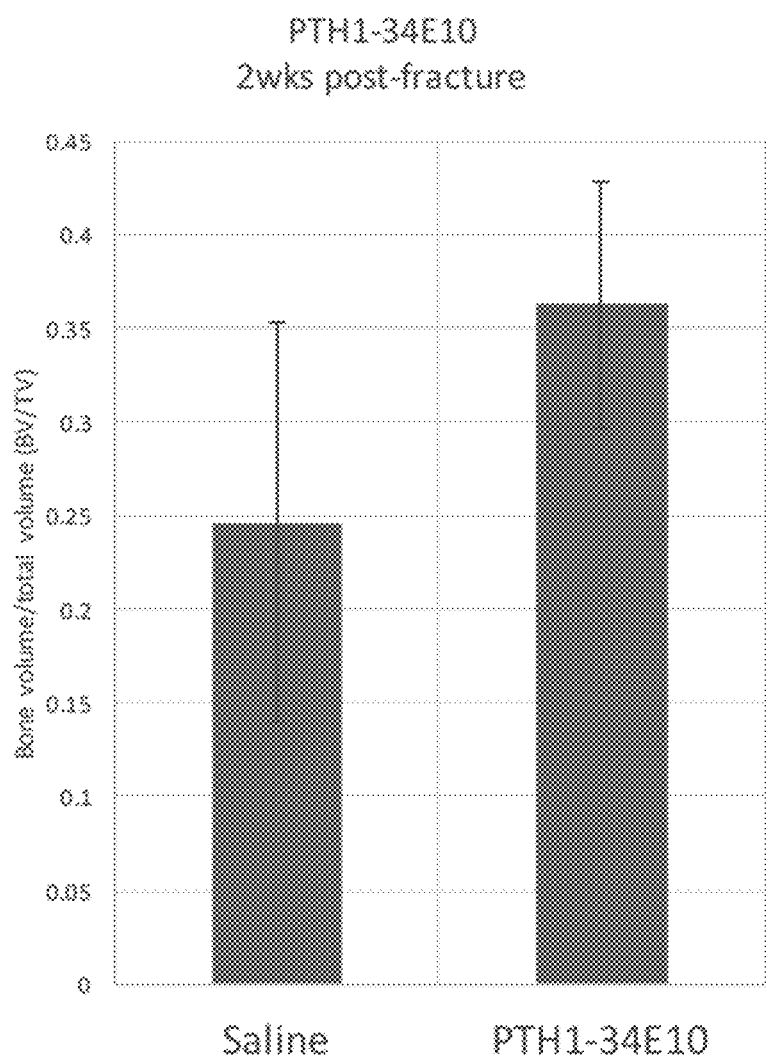
FIG. 26. Graph illustrating the effects of PTH1-34E10 and saline on bone volume after treatment.

Referring now to FIG. 26, the effects of PTH1-34E10 and saline on bone volume after treatment. Mice were treated daily with PTH1-34E10 for 2 weeks. At two week mice were sacrificed and femurs were excised for microCT analysis.

Figure 27:
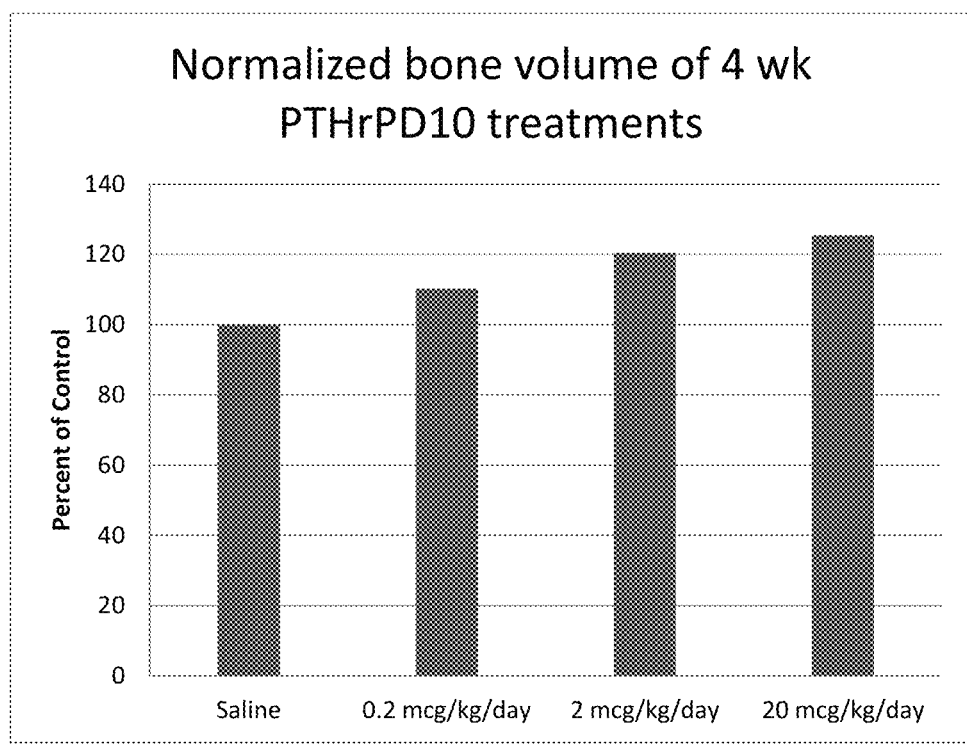
FIG. 27. Graph illustrating the effect of PTHrPD10 on bone volume after treatment.

Referring now to FIG. 27, the effects of PTHrPD10 and saline on normalized bone volume after treatment using the indicated doses. Mice were treated daily with PTHrPD10 for 4 weeks. At four week mice were sacrificed and femurs were excised for microCT analysis.

The Glutamic acid containing targeting ligands have higher up take in the kidneys than the other targeting ligands tested with uptakes ranging from 20-50% of measured dose per gram. This uptake is likely due glutamic reuptake receptors that are expressed in the kidneys. They are more selective for fractured bone over other bone than other targeting ligands as is indicated by the ratio of fractured to non-fracture delivery ranging from 7-12 in glutamic acid targeting ligands. Extending the glutamic polymers to 20 generated a modest improvement of delivery from the 20-50% of measured dose per gram for the 10mers up to 40-70% of measured dose per gram for the 20mers. This improvement was likely due to the increased affinity the additional glutamic acids brought for the exposed hydroxyapatite at the fracture site. The extended 20mer glutamic acid targeting ligands still suffered from similar kidney uptake issues as the shorter 10mers. Changing from L to D enantiomers appears to have no consistent effect on glutamic acid targeting ligands.

The aspartic acid targeting ligands appear to have the highest delivery of the targeting ligands with delivery accumulation ranging from 40-70% of measured dose per gram. However, the aspartic acids targeting ligands appear to be slightly less selective between fractured and non-fractured bone with ratios of fractured bone to non-fractured bone accumulation around 4-6 for L amino acid aspartic acid targeting and 6-9 for D amino acid aspartic acid targeting ligands. However, they don't suffer from as high of accumulation in kidneys as glutamic acid targeting ligands with accumulation of measured dose per gram typically remaining below 15%. Branched does not appear to perform any better than linear versions in its ability to deliver more to the fracture site.

Extending the length to 20 from 10 improved the consistency of the targeting ligand across the different types of peptides conjugated with L-Glu20 (labelled, "(L)D20"), all of the peptides were delivered at 50-70% of measured dose per gram. Changing from L to D enantiomers appears to improve its stability of the aspartic acid targeting ligands and increases targeting as was evident by the higher delivery rates and better selectivity ratios.

Peptides conjugated with AAD10 appear to have only moderate targeting abilities. It still maintains a more systemic distribution. But it was still able to maintain an improvement in its ability to deliver 2-5 times as much of the labeled compound to the fractured bone over non-fractured bone. Peptides conjugated with SDSDD appear to have only moderate targeting ability's with deliveries ranging from 20-40%. It still maintains a more systemic distribution. But it was still able to maintain an improvement in its ability to deliver 3-5 times as much of the labeled compound to the fractured bone over non-fractured bone. Peptides conjugated with $(DSS)_6$ appear to have only moderate targeting abilities towards fractured bone. It still maintains a more systemic distribution. But it was still able to maintain an improvement in its ability to deliver 2-3 times as much of the labeled compound to the fractured bone over non-fractured bone.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

The invention claimed is:

1. A compound having a structure of:

X-Y-Z wherein:
X is a polypeptide having an amino acid sequence of SEQ ID NO: 3;
Y is a linker; and
Z is a bone-targeting molecule;
or a pharmaceutically acceptable salt thereof.

2. The compound of claim 1, wherein Y is a non-releasable linker.

3. The compound of claim 1, wherein Y comprises a polypeptide.

4. The compound of claim 3, wherein Y is a polypeptide comprising at least 80% sequence identity to amino acid residues 35-84 of a full-length parathyroid hormone related peptide or parathyroid hormone.

5. The compound of claim 4, wherein Y is a polypeptide comprising at least 80% sequence identity to amino acid residues 35-46 of a full-length parathyroid hormone related peptide.

6. The compound of claim 1, wherein Z comprises not less than 4 and not more than 70 amino acids.

7. The compound of claim 6, wherein Z comprises not less than 4 and not more than 40 amino acids.

8. The compound of claim 1, wherein Z comprises not less than 6 and not more than 35 amino acids.

9. The compound of claim 1, wherein Z is charged.

10. The compound of claim 6, wherein at least one amino acid is aspartic acid or glutamic acid.

11. The compound of claim 1, wherein Z comprises not less than 6 and not more than 35 glutamic acid residues.

12. The compound of claim 1, wherein Z comprises not less than 6 and not more than 35 aspartic acid residues.

13. A compound having a structure of:

X-Y-Z wherein:
   X is a polypeptide having an amino acid sequence of SEQ ID NO: 3;
   Y is a non-releasable polypeptide linker; and
   Z comprises not less than 6 and not more than 40 glutamic acid residues or not less than 6 and not more than 40 aspartic acid residues;
or a pharmaceutically acceptable salt thereof.

14. The compound of claim 13, wherein Z comprises not less than 6 and not more than 35 glutamic acid residues.

15. The compound of claim 13, wherein Y is a polypeptide comprising at least 80% sequence identity to amino acid residues 35-46 of a full-length parathyroid hormone related peptide.

16. A method of treating a bone fracture, the method comprising administering to a patient in need thereof a therapeutically effective amount of a compound having a structure of:

X-Y-Z wherein:
   X is a polypeptide having an amino acid sequence of SEQ ID NO: 3;
   Y is a linker; and
   Z is a bone-targeting molecule;
or a pharmaceutically acceptable salt thereof.

17. The method of claim 16, wherein the compound, or a pharmaceutically acceptable salt thereof, is administered to the patient in need thereof orally, parenterally, rectally, or transdermally.

18. The method of claim 17, wherein the compound, or a pharmaceutically acceptable salt thereof, is subcutaneously administered to the patient in need thereof.

19. The method of claim 16, wherein the therapeutically effective amount of the compound, or a pharmaceutically acceptable salt thereof, provides a therapeutically effective amount of the compound, or a pharmaceutically acceptable salt thereof, to the bone fracture of the patient in need thereof.

20. The method of claim 19, wherein the therapeutically effective amount of the compound, or a pharmaceutically acceptable salt thereof, is from about 0.01 nmol/kg/day to about 100 nmol/kg/day.

* * * * *

SEQUENCE LISTING

```
<160> NUMBER OF SEQ ID NOS: 81

<210> SEQ ID NO 1
<211> LENGTH: 34
<212> TYPE: PRT
<213> ORGANISM: homo sapiens

<400> SEQUENCE: 1

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 2
<211> LENGTH: 34
<212> TYPE: PRT
<213> ORGANISM: homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 3
<211> LENGTH: 34
<212> TYPE: PRT
<213> ORGANISM: artificial
<220> FEATURE:
```

```
<223> OTHER INFORMATION: Abaloparatide 1-34 with 2-methylalanyl at
      residue 29 and aminated at residue 34
<220> FEATURE:
<221> NAME/KEY: MOD_RES
<222> LOCATION: (29)..(29)
<223> OTHER INFORMATION: 2-methyananyl
<220> FEATURE:
<221> NAME/KEY: MOD_RES
<222> LOCATION: (34)..(34)
<223> OTHER INFORMATION: amidation at C-terminus

<400> SEQUENCE: 3

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Ala Lys Leu His
            20                  25                  30

Thr Ala

<210> SEQ ID NO 4
<211> LENGTH: 35
<212> TYPE: PRT
<213> ORGANISM: homo sapiens

<400> SEQUENCE: 4

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Gly
        35

<210> SEQ ID NO 5
<211> LENGTH: 36
<212> TYPE: PRT
<213> ORGANISM: homo sapiens

<400> SEQUENCE: 5

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Gly Ile
        35

<210> SEQ ID NO 6
<211> LENGTH: 37
<212> TYPE: PRT
<213> ORGANISM: homo sapiens

<400> SEQUENCE: 6

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Gly Ile Arg
        35

<210> SEQ ID NO 7
<211> LENGTH: 38
<212> TYPE: PRT
<213> ORGANISM: homo sapiens

<400> SEQUENCE: 7
```

-continued

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Gly Ile Arg Ala
            35
```

<210> SEQ ID NO 8
<211> LENGTH: 39
<212> TYPE: PRT
<213> ORGANISM: Homo sapiens

<400> SEQUENCE: 8

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Gly Ile Arg Ala Thr
            35
```

<210> SEQ ID NO 9
<211> LENGTH: 40
<212> TYPE: PRT
<213> ORGANISM: homo sapiens

<400> SEQUENCE: 9

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Gly Ile Arg Ala Thr Ser
            35                  40
```

<210> SEQ ID NO 10
<211> LENGTH: 56
<212> TYPE: PRT
<213> ORGANISM: artificial
<220> FEATURE:
<223> OTHER INFORMATION: PTHrP1-46D10

<400> SEQUENCE: 10

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Gly Ile Arg Ala Thr Ser Glu Val Ser Pro Asn Ser Asp Asp
            35                  40                  45

Asp Asp Asp Asp Asp Asp Asp Asp
    50                  55
```

<210> SEQ ID NO 11
<211> LENGTH: 56
<212> TYPE: PRT
<213> ORGANISM: artificial
<220> FEATURE:
<223> OTHER INFORMATION: PTH1-46D10

<400> SEQUENCE: 11

```
Ser Val Ser Glu Ile Gln Leu Met His Asn Leu Gly Lys His Leu Asn
1               5                   10                  15
```

```
Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Asp Asp
        35                  40                  45

Asp Asp Asp Asp Asp Asp Asp Asp
    50                  55
```

<210> SEQ ID NO 12
<211> LENGTH: 141
<212> TYPE: PRT
<213> ORGANISM: Homo sapiens

<400> SEQUENCE: 12

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Phe Gly Ser Asp Asp Glu
    50                  55                  60

Gly Arg Tyr Leu Thr Gln Glu Thr Asn Lys Val Glu Thr Tyr Lys Glu
65                  70                  75                  80

Gln Pro Leu Lys Thr Pro Gly Lys Lys Lys Gly Lys Pro Gly Lys
                85                  90                  95

Arg Lys Glu Gln Glu Lys Lys Lys Arg Arg Thr Arg Ser Ala Trp Leu
                100                 105                 110

Asp Ser Gly Val Thr Gly Ser Gly Leu Glu Gly Asp His Leu Ser Asp
            115                 120                 125

Thr Ser Thr Thr Ser Leu Glu Leu Asp Ser Arg Arg His
        130                 135                 140
```

<210> SEQ ID NO 13
<211> LENGTH: 84
<212> TYPE: PRT
<213> ORGANISM: Homo sapiens

<400> SEQUENCE: 13

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln
```

<210> SEQ ID NO 14
<211> LENGTH: 8
<212> TYPE: PRT
<213> ORGANISM: artificial
<220> FEATURE:
<223> OTHER INFORMATION: Heparin-binding domain of FGF2 ("F109C")

<400> SEQUENCE: 14

```
Tyr Lys Arg Ser Arg Tyr Thr Cys
1               5

<210> SEQ ID NO 15
<211> LENGTH: 39
<212> TYPE: PRT
<213> ORGANISM: homo sapiens

<400> SEQUENCE: 15

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
                20                  25                  30

Gln Arg Val Lys Asn Lys Cys
            35

<210> SEQ ID NO 16
<211> LENGTH: 15
<212> TYPE: PRT
<213> ORGANISM: Homo sapiens

<400> SEQUENCE: 16

Tyr Ile Ala Gly Val Gly Gly Glu Lys Ser Gly Gly Phe Tyr Cys
1               5                   10                  15

<210> SEQ ID NO 17
<211> LENGTH: 30
<212> TYPE: PRT
<213> ORGANISM: Homo sapiens

<400> SEQUENCE: 17

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
                20                  25                  30

<210> SEQ ID NO 18
<211> LENGTH: 16
<212> TYPE: PRT
<213> ORGANISM: Homo sapiens

<400> SEQUENCE: 18

Asp Val Asp Val Pro Asp Gly Arg Gly Asp Ser Leu Ala Tyr Gly Cys
1               5                   10                  15

<210> SEQ ID NO 19
<211> LENGTH: 20
<212> TYPE: PRT
<213> ORGANISM: artificial
<220> FEATURE:
<223> OTHER INFORMATION: P4C (modified BMP-2 fragment)

<400> SEQUENCE: 19

Lys Ile Pro Lys Ala Ser Ser Val Pro Thr Glu Leu Ser Ala Ile Ser
1               5                   10                  15

Thr Leu Tyr Leu
            20

<210> SEQ ID NO 20
<211> LENGTH: 26
<212> TYPE: PRT
<213> ORGANISM: artificial
<220> FEATURE:
<223> OTHER INFORMATION: PreptinD10
```

<400> SEQUENCE: 20

Asp Val Ser Thr Ser Gln Ala Val Leu Pro Asp Asp Phe Pro Arg Tyr
1               5                   10                  15

Asp Asp Asp Asp Asp Asp Asp Asp Asp
            20                  25

<210> SEQ ID NO 21
<211> LENGTH: 5
<212> TYPE: PRT
<213> ORGANISM: artificial
<220> FEATURE:
<223> OTHER INFORMATION: SDSDD

<400> SEQUENCE: 21

Ser Asp Ser Asp Asp
1               5

<210> SEQ ID NO 22
<211> LENGTH: 18
<212> TYPE: PRT
<213> ORGANISM: artificial
<220> FEATURE:
<223> OTHER INFORMATION: (DSS)6

<400> SEQUENCE: 22

Asp Ser Ser Asp Ser Ser Asp Ser Ser Asp Ser Ser Asp Ser Ser Asp
1               5                   10                  15

Ser Ser

<210> SEQ ID NO 23
<211> LENGTH: 44
<212> TYPE: PRT
<213> ORGANISM: artificial
<220> FEATURE:
<223> OTHER INFORMATION: PTH1-34E10

<400> SEQUENCE: 23

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Glu Glu Glu Glu Glu Glu Glu Glu Glu Glu
        35                  40

<210> SEQ ID NO 24
<211> LENGTH: 46
<212> TYPE: PRT
<213> ORGANISM: artificial
<220> FEATURE:
<223> OTHER INFORMATION: PTHrP1-36E10

<400> SEQUENCE: 24

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Gly Ile Glu Glu Glu Glu Glu Glu Glu Glu Glu Glu
            35                  40                  45

<210> SEQ ID NO 25
<211> LENGTH: 40
<212> TYPE: PRT

```
<213> ORGANISM: artificial
<220> FEATURE:
<223> OTHER INFORMATION: PTHrP1-39C-MalE20
<220> FEATURE:
<221> NAME/KEY: MOD_RES
<222> LOCATION: (40)..(40)
<223> OTHER INFORMATION: Cys modified with maleimide-(Glu)20

<400> SEQUENCE: 25

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
                20                  25                  30

Thr Ala Gly Ile Arg Ala Thr Cys
        35                  40

<210> SEQ ID NO 26
<211> LENGTH: 8
<212> TYPE: PRT
<213> ORGANISM: artificial
<220> FEATURE:
<223> OTHER INFORMATION: F109C conjugated with D10
<220> FEATURE:
<221> NAME/KEY: MOD_RES
<222> LOCATION: (8)..(8)
<223> OTHER INFORMATION: Cys modified by Maleimide-(Asp)10

<400> SEQUENCE: 26

Tyr Lys Arg Ser Arg Tyr Thr Cys
1               5

<210> SEQ ID NO 27
<211> LENGTH: 8
<212> TYPE: PRT
<213> ORGANISM: artificial
<220> FEATURE:
<223> OTHER INFORMATION: F109C conjugated with D20
<220> FEATURE:
<221> NAME/KEY: MOD_RES
<222> LOCATION: (8)..(8)
<223> OTHER INFORMATION: Cys modified with Maleimide-(Asp)20

<400> SEQUENCE: 27

Tyr Lys Arg Ser Arg Tyr Thr Cys
1               5

<210> SEQ ID NO 28
<211> LENGTH: 8
<212> TYPE: PRT
<213> ORGANISM: artificial
<220> FEATURE:
<223> OTHER INFORMATION: F109C conjugated with E10
<220> FEATURE:
<221> NAME/KEY: MOD_RES
<222> LOCATION: (8)..(8)
<223> OTHER INFORMATION: Cys modified with Maleimide-(Glu)10

<400> SEQUENCE: 28

Tyr Lys Arg Ser Arg Tyr Thr Cys
1               5

<210> SEQ ID NO 29
<211> LENGTH: 8
<212> TYPE: PRT
<213> ORGANISM: artificial
<220> FEATURE:
<223> OTHER INFORMATION: F109C conjugated with E20
<220> FEATURE:
<221> NAME/KEY: MOD_RES
```

<222> LOCATION: (8)..(8)
<223> OTHER INFORMATION: Cys modified with Maleimide-(Glu)20

<400> SEQUENCE: 29

Tyr Lys Arg Ser Arg Tyr Thr Cys
1               5

<210> SEQ ID NO 30
<211> LENGTH: 8
<212> TYPE: PRT
<213> ORGANISM: artificial
<220> FEATURE:
<223> OTHER INFORMATION: F109C conjugated with AAD10
<220> FEATURE:
<221> NAME/KEY: MOD_RES
<222> LOCATION: (8)..(8)
<223> OTHER INFORMATION: Cys modified with Maleimide-(2-amino-adipic
      acid)10

<400> SEQUENCE: 30

Tyr Lys Arg Ser Arg Tyr Thr Cys
1               5

<210> SEQ ID NO 31
<211> LENGTH: 8
<212> TYPE: PRT
<213> ORGANISM: artificial
<220> FEATURE:
<223> OTHER INFORMATION: F109C conjugated with SDSDD
<220> FEATURE:
<221> NAME/KEY: MOD_RES
<222> LOCATION: (8)..(8)
<223> OTHER INFORMATION: Cys modified with Maleimide-Ser-Asp-Ser-Asp-Asp

<400> SEQUENCE: 31

Tyr Lys Arg Ser Arg Tyr Thr Cys
1               5

<210> SEQ ID NO 32
<211> LENGTH: 8
<212> TYPE: PRT
<213> ORGANISM: artificial
<220> FEATURE:
<223> OTHER INFORMATION: F109C conjugated with (DSS)6
<220> FEATURE:
<221> NAME/KEY: MOD_RES
<222> LOCATION: (8)..(8)
<223> OTHER INFORMATION: Cys modified with Maleimide-(Asp-Ser-Ser)6

<400> SEQUENCE: 32

Tyr Lys Arg Ser Arg Tyr Thr Cys
1               5

<210> SEQ ID NO 33
<211> LENGTH: 39
<212> TYPE: PRT
<213> ORGANISM: artificial
<220> FEATURE:
<223> OTHER INFORMATION: PACAPC conjugated with D10
<220> FEATURE:
<221> NAME/KEY: MOD_RES
<222> LOCATION: (39)..(39)
<223> OTHER INFORMATION: Cys modified with Maleimide-(Asp)10

<400> SEQUENCE: 33

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 34
<211> LENGTH: 39
<212> TYPE: PRT
<213> ORGANISM: artificial
<220> FEATURE:
<223> OTHER INFORMATION: PACAPC conjugated with D20
<220> FEATURE:
<221> NAME/KEY: MOD_RES
<222> LOCATION: (39)..(39)
<223> OTHER INFORMATION: Cys modified with Maleimide-(Asp)20

<400> SEQUENCE: 34

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 35
<211> LENGTH: 39
<212> TYPE: PRT
<213> ORGANISM: artificial
<220> FEATURE:
<223> OTHER INFORMATION: PACAPC conjugated with E10
<220> FEATURE:
<221> NAME/KEY: MOD_RES
<222> LOCATION: (39)..(39)
<223> OTHER INFORMATION: Cys modified with Maleimide-(Glu)10

<400> SEQUENCE: 35

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 36
<211> LENGTH: 39
<212> TYPE: PRT
<213> ORGANISM: artificial
<220> FEATURE:
<223> OTHER INFORMATION: PACAPC conjugated with E20
<220> FEATURE:
<221> NAME/KEY: MOD_RES
<222> LOCATION: (39)..(39)
<223> OTHER INFORMATION: Cys modified with Maleimide-(Glu)20

<400> SEQUENCE: 36

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 37
<211> LENGTH: 39
<212> TYPE: PRT
<213> ORGANISM: artificial
<220> FEATURE:

```
<223> OTHER INFORMATION: PACAPC conjugated with AAD10
<220> FEATURE:
<221> NAME/KEY: MOD_RES
<222> LOCATION: (39)..(39)
<223> OTHER INFORMATION: Cys modified with Maleimide-(2-amino-adipic
      acid)10

<400> SEQUENCE: 37

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 38
<211> LENGTH: 39
<212> TYPE: PRT
<213> ORGANISM: artificial
<220> FEATURE:
<223> OTHER INFORMATION: PACAPC conjugated with SDSDD
<220> FEATURE:
<221> NAME/KEY: MOD_RES
<222> LOCATION: (39)..(39)
<223> OTHER INFORMATION: Cys modified with Maleimide-Ser-Asp-Ser-Asp-Asp

<400> SEQUENCE: 38

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 39
<211> LENGTH: 39
<212> TYPE: PRT
<213> ORGANISM: artificial
<220> FEATURE:
<223> OTHER INFORMATION: PACAPC conjugated with (DSS)6
<220> FEATURE:
<221> NAME/KEY: MOD_RES
<222> LOCATION: (39)..(39)
<223> OTHER INFORMATION: Cys modified with Maleimide-(Asp-Ser-Ser)6

<400> SEQUENCE: 39

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 40
<211> LENGTH: 15
<212> TYPE: PRT
<213> ORGANISM: artificial
<220> FEATURE:
<223> OTHER INFORMATION: CTCC conjugated with D10
<220> FEATURE:
<221> NAME/KEY: MOD_RES
<222> LOCATION: (15)..(15)
<223> OTHER INFORMATION: Cys modified with Maleimide-(Asp)10

<400> SEQUENCE: 40

Tyr Ile Ala Gly Val Gly Gly Glu Lys Ser Gly Gly Phe Tyr Cys
```

<210> SEQ ID NO 41
<211> LENGTH: 15
<212> TYPE: PRT
<213> ORGANISM: artificial
<220> FEATURE:
<223> OTHER INFORMATION: CTCC conjugated with D20
<220> FEATURE:
<221> NAME/KEY: MOD_RES
<222> LOCATION: (15)..(15)
<223> OTHER INFORMATION: Cys modified with Maleimide-(Asp)20

<400> SEQUENCE: 41

Tyr Ile Ala Gly Val Gly Gly Glu Lys Ser Gly Gly Phe Tyr Cys
1               5                   10                  15

<210> SEQ ID NO 42
<211> LENGTH: 15
<212> TYPE: PRT
<213> ORGANISM: artificial
<220> FEATURE:
<223> OTHER INFORMATION: CTCC conjugated with E10
<220> FEATURE:
<221> NAME/KEY: MOD_RES
<222> LOCATION: (15)..(15)
<223> OTHER INFORMATION: Cys modified with Maleimide-(Glu)10

<400> SEQUENCE: 42

Tyr Ile Ala Gly Val Gly Gly Glu Lys Ser Gly Gly Phe Tyr Cys
1               5                   10                  15

<210> SEQ ID NO 43
<211> LENGTH: 15
<212> TYPE: PRT
<213> ORGANISM: artificial
<220> FEATURE:
<223> OTHER INFORMATION: CTCC conjugated with E20
<220> FEATURE:
<221> NAME/KEY: MOD_RES
<222> LOCATION: (15)..(15)
<223> OTHER INFORMATION: Cys modified with Maleimide-(Glu)20

<400> SEQUENCE: 43

Tyr Ile Ala Gly Val Gly Gly Glu Lys Ser Gly Gly Phe Tyr Cys
1               5                   10                  15

<210> SEQ ID NO 44
<211> LENGTH: 15
<212> TYPE: PRT
<213> ORGANISM: artificial
<220> FEATURE:
<223> OTHER INFORMATION: CTCC conjugated with AAD10
<220> FEATURE:
<221> NAME/KEY: MOD_RES
<222> LOCATION: (15)..(15)
<223> OTHER INFORMATION: Cys modified with Maleimide-(2-amino-adipic
      acid)10

<400> SEQUENCE: 44

Tyr Ile Ala Gly Val Gly Gly Glu Lys Ser Gly Gly Phe Tyr Cys
1               5                   10                  15

<210> SEQ ID NO 45
<211> LENGTH: 15
<212> TYPE: PRT
<213> ORGANISM: artificial
<220> FEATURE:
<223> OTHER INFORMATION: CTCC conjugated with SDSDD
<220> FEATURE:

```
<221> NAME/KEY: MOD_RES
<222> LOCATION: (15)..(15)
<223> OTHER INFORMATION: Cys modified with
      Maleimide-(Ser-Asp-Ser-Asp-Asp)

<400> SEQUENCE: 45

Tyr Ile Ala Gly Val Gly Gly Glu Lys Ser Gly Gly Phe Tyr Cys
1               5                  10                  15

<210> SEQ ID NO 46
<211> LENGTH: 15
<212> TYPE: PRT
<213> ORGANISM: artificial
<220> FEATURE:
<223> OTHER INFORMATION: CTCC conjugated with (DSS)6
<220> FEATURE:
<221> NAME/KEY: MOD_RES
<222> LOCATION: (15)..(15)
<223> OTHER INFORMATION: Cys modified with Maleimide-(Asp-Ser-Ser)6

<400> SEQUENCE: 46

Tyr Ile Ala Gly Val Gly Gly Glu Lys Ser Gly Gly Phe Tyr Cys
1               5                  10                  15

<210> SEQ ID NO 47
<211> LENGTH: 30
<212> TYPE: PRT
<213> ORGANISM: artificial
<220> FEATURE:
<223> OTHER INFORMATION: Ck2.3C conjugated with D10
<220> FEATURE:
<221> NAME/KEY: MOD_RES
<222> LOCATION: (30)..(30)
<223> OTHER INFORMATION: Cys modified with Maleimide-(Asp)10

<400> SEQUENCE: 47

Arg Gln Ile Lys Ile Trp Phe Gln Asn Arg Arg Met Lys Trp Lys Lys
1               5                  10                  15

Ile Pro Val Gly Glu Ser Leu Lys Asp Leu Ile Asp Gln Cys
            20                  25                  30

<210> SEQ ID NO 48
<211> LENGTH: 30
<212> TYPE: PRT
<213> ORGANISM: artificial
<220> FEATURE:
<223> OTHER INFORMATION: Ck2.3C conjugated with D20
<220> FEATURE:
<221> NAME/KEY: MOD_RES
<222> LOCATION: (30)..(30)
<223> OTHER INFORMATION: Cys modified with Maleimide-(Asp)20

<400> SEQUENCE: 48

Arg Gln Ile Lys Ile Trp Phe Gln Asn Arg Arg Met Lys Trp Lys Lys
1               5                  10                  15

Ile Pro Val Gly Glu Ser Leu Lys Asp Leu Ile Asp Gln Cys
            20                  25                  30

<210> SEQ ID NO 49
<211> LENGTH: 30
<212> TYPE: PRT
<213> ORGANISM: artificial
<220> FEATURE:
<223> OTHER INFORMATION: Ck2.3C conjugated with E10
<220> FEATURE:
<221> NAME/KEY: MOD_RES
<222> LOCATION: (30)..(30)
<223> OTHER INFORMATION: Cys modified with Maleimide-(Glu)10
```

```
<400> SEQUENCE: 49

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 50
<211> LENGTH: 30
<212> TYPE: PRT
<213> ORGANISM: artificial
<220> FEATURE:
<223> OTHER INFORMATION: Ck2.3C conjugated with E20
<220> FEATURE:
<221> NAME/KEY: MOD_RES
<222> LOCATION: (30)..(30)
<223> OTHER INFORMATION: Cys modified with Maleimide-(Glu)20

<400> SEQUENCE: 50

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 51
<211> LENGTH: 30
<212> TYPE: PRT
<213> ORGANISM: artificial
<220> FEATURE:
<223> OTHER INFORMATION: Ck2.3C conjugated with AAD10
<220> FEATURE:
<221> NAME/KEY: MOD_RES
<222> LOCATION: (30)..(30)
<223> OTHER INFORMATION: Cys modified by maleimide--(2-amino-adipic
      acid)10

<400> SEQUENCE: 51

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 52
<211> LENGTH: 30
<212> TYPE: PRT
<213> ORGANISM: artificial
<220> FEATURE:
<223> OTHER INFORMATION: Ck2.3C conjugated with SDSDD
<220> FEATURE:
<221> NAME/KEY: MOD_RES
<222> LOCATION: (30)..(30)
<223> OTHER INFORMATION: Cys modified with
      Maleimide-(Ser-Asp-Ser-Asp-Asp)

<400> SEQUENCE: 52

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 53
<211> LENGTH: 30
<212> TYPE: PRT
<213> ORGANISM: artificial
<220> FEATURE:
<223> OTHER INFORMATION: Ck2.3C conjugated with (DSS)6
<220> FEATURE:
<221> NAME/KEY: MOD_RES
```

```
<222> LOCATION: (30)..(30)
<223> OTHER INFORMATION: Cys modified with Maleimide-(Asp-Ser-Ser)6

<400> SEQUENCE: 53

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 54
<211> LENGTH: 16
<212> TYPE: PRT
<213> ORGANISM: artificial
<220> FEATURE:
<223> OTHER INFORMATION: ODPC conjugated with D10
<220> FEATURE:
<221> NAME/KEY: MOD_RES
<222> LOCATION: (16)..(16)
<223> OTHER INFORMATION: Cys modified with Maleimide-(Asp)10

<400> SEQUENCE: 54

Asp Val Asp Val Pro Asp Gly Arg Gly Asp Ser Leu Ala Tyr Gly Cys
1               5                   10                  15

<210> SEQ ID NO 55
<211> LENGTH: 16
<212> TYPE: PRT
<213> ORGANISM: artificial
<220> FEATURE:
<223> OTHER INFORMATION: ODPC conjugated with D20
<220> FEATURE:
<221> NAME/KEY: MOD_RES
<222> LOCATION: (16)..(16)
<223> OTHER INFORMATION: Cys modified with Maleimide-(Asp)20

<400> SEQUENCE: 55

Asp Val Asp Val Pro Asp Gly Arg Gly Asp Ser Leu Ala Tyr Gly Cys
1               5                   10                  15

<210> SEQ ID NO 56
<211> LENGTH: 16
<212> TYPE: PRT
<213> ORGANISM: artificial
<220> FEATURE:
<223> OTHER INFORMATION: ODPC conjugated with E10
<220> FEATURE:
<221> NAME/KEY: MOD_RES
<222> LOCATION: (16)..(16)
<223> OTHER INFORMATION: Cys modified with Maleimide-(Glu)10

<400> SEQUENCE: 56

Asp Val Asp Val Pro Asp Gly Arg Gly Asp Ser Leu Ala Tyr Gly Cys
1               5                   10                  15

<210> SEQ ID NO 57
<211> LENGTH: 16
<212> TYPE: PRT
<213> ORGANISM: artificial
<220> FEATURE:
<223> OTHER INFORMATION: ODPC conjugated with E20
<220> FEATURE:
<221> NAME/KEY: MOD_RES
<222> LOCATION: (16)..(16)
<223> OTHER INFORMATION: Cys modified with Maleimide-(Glu)20

<400> SEQUENCE: 57

Asp Val Asp Val Pro Asp Gly Arg Gly Asp Ser Leu Ala Tyr Gly Cys
1               5                   10                  15
```

```
<210> SEQ ID NO 58
<211> LENGTH: 16
<212> TYPE: PRT
<213> ORGANISM: artificial
<220> FEATURE:
<223> OTHER INFORMATION: ODPC conjugated with AAD10
<220> FEATURE:
<221> NAME/KEY: MOD_RES
<222> LOCATION: (16)..(16)
<223> OTHER INFORMATION: Cys modified with Maleimide-(2-amino-adipic
      acid)10

<400> SEQUENCE: 58

Asp Val Asp Val Pro Asp Gly Arg Gly Asp Ser Leu Ala Tyr Gly Cys
1               5                   10                  15

<210> SEQ ID NO 59
<211> LENGTH: 16
<212> TYPE: PRT
<213> ORGANISM: artificial
<220> FEATURE:
<223> OTHER INFORMATION: ODPC conjugated with SDSDD
<220> FEATURE:
<221> NAME/KEY: MOD_RES
<222> LOCATION: (16)..(16)
<223> OTHER INFORMATION: Cys modified with
      Maleimide-(Ser-Asp-Ser-Asp-Asp)

<400> SEQUENCE: 59

Asp Val Asp Val Pro Asp Gly Arg Gly Asp Ser Leu Ala Tyr Gly Cys
1               5                   10                  15

<210> SEQ ID NO 60
<211> LENGTH: 16
<212> TYPE: PRT
<213> ORGANISM: artificial
<220> FEATURE:
<223> OTHER INFORMATION: ODPC conjugated with (DSS)6
<220> FEATURE:
<221> NAME/KEY: MOD_RES
<222> LOCATION: (16)..(16)
<223> OTHER INFORMATION: Cys modified with Maleimide-(Asp-Ser-Ser)6

<400> SEQUENCE: 60

Asp Val Asp Val Pro Asp Gly Arg Gly Asp Ser Leu Ala Tyr Gly Cys
1               5                   10                  15

<210> SEQ ID NO 61
<211> LENGTH: 21
<212> TYPE: PRT
<213> ORGANISM: artificial
<220> FEATURE:
<223> OTHER INFORMATION: P4C conjugated with D10
<220> FEATURE:
<221> NAME/KEY: MOD_RES
<222> LOCATION: (21)..(21)
<223> OTHER INFORMATION: Cys modified with Maleimide-(Asp)10

<400> SEQUENCE: 61

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 62
<211> LENGTH: 21
<212> TYPE: PRT
<213> ORGANISM: artificial
<220> FEATURE:
```

-continued

```
<223> OTHER INFORMATION: P4C conjugated with D20
<220> FEATURE:
<221> NAME/KEY: MOD_RES
<222> LOCATION: (21)..(21)
<223> OTHER INFORMATION: Cys modified with Maleimide-(Asp)20

<400> SEQUENCE: 62

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 63
<211> LENGTH: 21
<212> TYPE: PRT
<213> ORGANISM: artificial
<220> FEATURE:
<223> OTHER INFORMATION: P4C conjugated with E10
<220> FEATURE:
<221> NAME/KEY: MOD_RES
<222> LOCATION: (21)..(21)
<223> OTHER INFORMATION: Cys modified with Maleimide-(Glu)10

<400> SEQUENCE: 63

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 64
<211> LENGTH: 21
<212> TYPE: PRT
<213> ORGANISM: artificial
<220> FEATURE:
<223> OTHER INFORMATION: P4C conjugated with E20
<220> FEATURE:
<221> NAME/KEY: MOD_RES
<222> LOCATION: (21)..(21)
<223> OTHER INFORMATION: Cys modified with Maleimide-(Glu)20

<400> SEQUENCE: 64

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 65
<211> LENGTH: 21
<212> TYPE: PRT
<213> ORGANISM: artificial
<220> FEATURE:
<223> OTHER INFORMATION: P4C conjugated with AAD10
<220> FEATURE:
<221> NAME/KEY: MOD_RES
<222> LOCATION: (21)..(21)
<223> OTHER INFORMATION: Cys modified with Maleimide-(2-amino-adipic
      acid)10

<400> SEQUENCE: 65

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 66
<211> LENGTH: 21
<212> TYPE: PRT
```

```
<213> ORGANISM: artificial
<220> FEATURE:
<223> OTHER INFORMATION: P4C conjugated with SDSDD
<220> FEATURE:
<221> NAME/KEY: MOD_RES
<222> LOCATION: (21)..(21)
<223> OTHER INFORMATION: Cys modified with
      Maleimide-(Ser-Asp-Ser-Asp-Asp)

<400> SEQUENCE: 66

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 67
<211> LENGTH: 21
<212> TYPE: PRT
<213> ORGANISM: artificial
<220> FEATURE:
<223> OTHER INFORMATION: P4C conjugated with (DSS)6
<220> FEATURE:
<221> NAME/KEY: MOD_RES
<222> LOCATION: (21)..(21)
<223> OTHER INFORMATION: Cys modified with Maleimide-(Asp-Ser-Ser)6

<400> SEQUENCE: 67

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 68
<211> LENGTH: 10
<212> TYPE: PRT
<213> ORGANISM: artificial
<220> FEATURE:
<223> OTHER INFORMATION: Branched D4 Y
<220> FEATURE:
<221> NAME/KEY: MOD_RES
<222> LOCATION: (1)..(1)
<223> OTHER INFORMATION: PEG (polyethylene glycol) modified Tyrosine

<400> SEQUENCE: 68

Tyr Lys Asp Asp Asp Asp Asp Asp Asp Asp
1               5                   10

<210> SEQ ID NO 69
<211> LENGTH: 18
<212> TYPE: PRT
<213> ORGANISM: artificial
<220> FEATURE:
<223> OTHER INFORMATION: Branched D8 Y
<220> FEATURE:
<221> NAME/KEY: MOD_RES
<222> LOCATION: (1)..(1)
<223> OTHER INFORMATION: PEG (polyethylene glycol) modified Tyrosine

<400> SEQUENCE: 69

Tyr Lys Asp Asp Asp Asp Asp Asp Asp Asp Asp Asp Asp Asp Asp Asp
1               5                   10                  15

Asp Asp

<210> SEQ ID NO 70
<211> LENGTH: 8
<212> TYPE: PRT
<213> ORGANISM: artificial
<220> FEATURE:
```

-continued

```
<223> OTHER INFORMATION: F109C conjugated with branched D10
<220> FEATURE:
<221> NAME/KEY: MOD_RES
<222> LOCATION: (8)..(8)
<223> OTHER INFORMATION: Cys modified with Maleimide-Lys((Asp)10)2

<400> SEQUENCE: 70

Tyr Lys Arg Ser Arg Tyr Thr Cys
1               5

<210> SEQ ID NO 71
<211> LENGTH: 39
<212> TYPE: PRT
<213> ORGANISM: artificial
<220> FEATURE:
<223> OTHER INFORMATION: PACAPC conjugated with branched D10
<220> FEATURE:
<221> NAME/KEY: MOD_RES
<222> LOCATION: (39)..(39)
<223> OTHER INFORMATION: Cys modified with Maleimide-Lys((Asp)10)2

<400> SEQUENCE: 71

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 72
<211> LENGTH: 15
<212> TYPE: PRT
<213> ORGANISM: artificial
<220> FEATURE:
<223> OTHER INFORMATION: CTCC conjugated with branched D10
<220> FEATURE:
<221> NAME/KEY: MOD_RES
<222> LOCATION: (15)..(15)
<223> OTHER INFORMATION: Cys modified with Maleimide-Lys((Asp)10)2

<400> SEQUENCE: 72

Tyr Ile Ala Gly Val Gly Gly Glu Lys Ser Gly Gly Phe Tyr Cys
1               5                   10                  15

<210> SEQ ID NO 73
<211> LENGTH: 30
<212> TYPE: PRT
<213> ORGANISM: artificial
<220> FEATURE:
<223> OTHER INFORMATION: Ck2.3C conjugated with branched D10
<220> FEATURE:
<221> NAME/KEY: MOD_RES
<222> LOCATION: (30)..(30)
<223> OTHER INFORMATION: Cys modified with Maleimide-Lys((Asp)10)2

<400> SEQUENCE: 73

Arg Gln Ile Lys Ile Trp Phe Gln Asn Arg Arg Met Lys Trp Lys Lys
1               5                   10                  15

Ile Pro Val Gly Glu Ser Leu Lys Asp Leu Ile Asp Gln Cys
            20                  25                  30

<210> SEQ ID NO 74
<211> LENGTH: 16
<212> TYPE: PRT
<213> ORGANISM: artificial
<220> FEATURE:
<223> OTHER INFORMATION: ODPC conjugated with branched D10
<220> FEATURE:
```

```
<221> NAME/KEY: MOD_RES
<222> LOCATION: (16)..(16)
<223> OTHER INFORMATION: Cys modified with Maleimide-Lys((Asp)10)2

<400> SEQUENCE: 74

Asp Val Asp Val Pro Asp Gly Arg Gly Asp Ser Leu Ala Tyr Gly Cys
1               5                   10                  15

<210> SEQ ID NO 75
<211> LENGTH: 21
<212> TYPE: PRT
<213> ORGANISM: artificial
<220> FEATURE:
<223> OTHER INFORMATION: P4C conjugated with branched D10
<220> FEATURE:
<221> NAME/KEY: MOD_RES
<222> LOCATION: (21)..(21)
<223> OTHER INFORMATION: Cys modified with Maleimide-Lys((Asp)10)2

<400> SEQUENCE: 75

Lys Ile Pro Lys Ala Ser Ser Val Pro Thr Glu Leu Ser Ala Ile Ser
1               5                   10                  15

Thr Leu Tyr Leu Cys
            20

<210> SEQ ID NO 76
<211> LENGTH: 8
<212> TYPE: PRT
<213> ORGANISM: artificial
<220> FEATURE:
<223> OTHER INFORMATION: F109C conjugated with branched E10
<220> FEATURE:
<221> NAME/KEY: MOD_RES
<222> LOCATION: (8)..(8)
<223> OTHER INFORMATION: Cys modified with Maleimide

<400> SEQUENCE: 76

Tyr Lys Arg Ser Arg Tyr Thr Cys
1               5

<210> SEQ ID NO 77
<211> LENGTH: 39
<212> TYPE: PRT
<213> ORGANISM: artificial
<220> FEATURE:
<223> OTHER INFORMATION: PACAPC conjugated with branched E10
<220> FEATURE:
<221> NAME/KEY: MOD_RES
<222> LOCATION: (39)..(39)
<223> OTHER INFORMATION: Cys modified with Maleimide-Lys((Glu)10)2

<400> SEQUENCE: 77

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys Cys
        35

<210> SEQ ID NO 78
<211> LENGTH: 15
<212> TYPE: PRT
<213> ORGANISM: artificial
<220> FEATURE:
<223> OTHER INFORMATION: CTCC conjugated with branched E10
<220> FEATURE:
<221> NAME/KEY: MOD_RES
<222> LOCATION: (15)..(15)
```

```
<223> OTHER INFORMATION: Cys modified with Maleimide-Lys((Glu)10)2

<400> SEQUENCE: 78

Tyr Ile Ala Gly Val Gly Gly Glu Lys Ser Gly Gly Phe Tyr Cys
1               5                   10                  15

<210> SEQ ID NO 79
<211> LENGTH: 30
<212> TYPE: PRT
<213> ORGANISM: artificial
<220> FEATURE:
<223> OTHER INFORMATION: Ck2.3C conjugated with branched E10
<220> FEATURE:
<221> NAME/KEY: MOD_RES
<222> LOCATION: (30)..(30)
<223> OTHER INFORMATION: Cys modified with Maleimide-Lys((Glu)10)2

<400> SEQUENCE: 79

Arg Gln Ile Lys Ile Trp Phe Gln Asn Arg Arg Met Lys Trp Lys Lys
1               5                   10                  15
Ile Pro Val Gly Glu Ser Leu Lys Asp Leu Ile Asp Gln Cys
            20                  25                  30

<210> SEQ ID NO 80
<211> LENGTH: 16
<212> TYPE: PRT
<213> ORGANISM: artificial
<220> FEATURE:
<223> OTHER INFORMATION: ODPC conjugated with branched E10
<220> FEATURE:
<221> NAME/KEY: MOD_RES
<222> LOCATION: (16)..(16)
<223> OTHER INFORMATION: Cys modified with Maleimide-Lys((Glu)10)2

<400> SEQUENCE: 80

Asp Val Asp Val Pro Asp Gly Arg Gly Asp Ser Leu Ala Tyr Gly Cys
1               5                   10                  15

<210> SEQ ID NO 81
<211> LENGTH: 21
<212> TYPE: PRT
<213> ORGANISM: artificial
<220> FEATURE:
<223> OTHER INFORMATION: P4C conjugated with branched E10
<220> FEATURE:
<221> NAME/KEY: MOD_RES
<222> LOCATION: (21)..(21)
<223> OTHER INFORMATION: Cys modified with Maleimide-Lys((Glu)10)2

<400> SEQUENCE: 81

Lys Ile Pro Lys Ala Ser Ser Val Pro Thr Glu Leu Ser Ala Ile Ser
1               5                   10                  15
Thr Leu Tyr Leu Cys
            20
```